United States Patent
Zacharias

(10) Patent No.: US 10,470,926 B2
(45) Date of Patent: Nov. 12, 2019

(54) CYCLIC APERTURE FLOW REGULATOR SYSTEM

(71) Applicant: Alcon Research, Ltd., Fort Worth, TX (US)

(72) Inventor: Jaime Zacharias, Santiago (CL)

(73) Assignee: Alcon Research, Ltd., Fort Worth, TX (US)

( * ) Notice: Subject to any disclaimer, the term of this patent is extended or adjusted under 35 U.S.C. 154(b) by 750 days.

(21) Appl. No.: 14/559,878

(22) Filed: Dec. 3, 2014

(65) Prior Publication Data

US 2015/0359666 A1 Dec. 17, 2015

(30) Foreign Application Priority Data

Jun. 16, 2014 (WO) .................. PCT/IB2014/062252

(51) Int. Cl.
*A61F 9/007* (2006.01)
*A61M 1/00* (2006.01)

(52) U.S. Cl.
CPC .......... *A61F 9/00736* (2013.01); *A61F 9/007* (2013.01); *A61M 1/0035* (2014.02); *A61M 1/0037* (2013.01); *A61M 1/0066* (2013.01); *A61M 1/0082* (2014.02); *A61F 9/00745* (2013.01); *A61M 2210/0612* (2013.01)

(58) Field of Classification Search
CPC .. A61F 9/00736; A61F 9/007; A61F 9/00745; A61M 1/0035; A61M 1/0082; A61M 1/0037; A61M 1/0066; A61M 1/0025; A61M 1/0031; A61M 1/1031; A61M 2210/0612; A61M 15/025
See application file for complete search history.

(56) References Cited

U.S. PATENT DOCUMENTS

| | | | | |
|---|---|---|---|---|
| 4,508,532 A | * | 4/1985 | Drews ................ | A61F 9/00736 604/155 |
| 4,770,654 A | * | 9/1988 | Rogers ............... | A61F 9/00736 604/22 |
| 5,569,188 A | | 10/1996 | Mackool | |
| 5,989,212 A | * | 11/1999 | Sussman ............ | A61F 9/00736 604/114 |

(Continued)

FOREIGN PATENT DOCUMENTS

| CN | 1703251 A | 11/2005 |
|---|---|---|
| CN | 101426541 A | 5/2009 |

(Continued)

OTHER PUBLICATIONS

International Searching Authority, International Preliminary Report on Patentability, PCT/IB2014/062252, dated Dec. 8, 2015, 8 pages.

*Primary Examiner* — Edelmira Bosques
*Assistant Examiner* — Tezita Z Watts

(57) ABSTRACT

A cyclic aperture flow regulator system has an adjustable fluid aperture in a fluid path connecting the aspiration port of a surgical probe with a vacuum source. The cross-sectional area of the fluid aperture can be modified by an actuator. The actuator is controlled to modify the cross-sectional area of the adjustable fluid aperture in cycles. During each cycle, the fluid aperture cross-sectional area is substantially reduced or closed. The cycles occur at a rate fast enough to produce a substantially steady flow, with minimum flow ripple and pressure ripple.

14 Claims, 38 Drawing Sheets

(56) References Cited

U.S. PATENT DOCUMENTS

| | | | | |
|---|---|---|---|---|
| 2002/0166989 A1* | 11/2002 | Peterson | ............ | A61M 1/1656 |
| | | | | 251/208 |
| 2005/0043670 A1* | 2/2005 | Rosenberg | ............ | A61B 5/031 |
| | | | | 604/9 |
| 2006/0058823 A1* | 3/2006 | Dimalanta | ......... | A61F 9/00736 |
| | | | | 606/167 |
| 2006/0129092 A1* | 6/2006 | Hanlon | ................ | A61M 39/12 |
| | | | | 604/93.01 |
| 2007/0088282 A1* | 4/2007 | Ranalletta | ............ | A61M 5/204 |
| | | | | 604/184 |
| 2013/0053693 A1* | 2/2013 | Breznock | ............ | A61M 1/3627 |
| | | | | 600/433 |
| 2013/0060210 A1* | 3/2013 | Ross | .................. | A61M 1/0035 |
| | | | | 604/318 |

FOREIGN PATENT DOCUMENTS

| | | |
|---|---|---|
| CN | 102245140 A | 11/2011 |
| CN | 102361606 A | 2/2012 |
| TW | 243411 B | 3/1995 |
| WO | 2006134326 | 12/2006 |

* cited by examiner

DETAIL B

DETAIL C

DETAIL D

DETAIL E

DETAIL F

SECTION D-D

DETAIL G

SECTION C-C

SLICE DETAIL G-1

SLICE DETAIL G-2

SLICE DETAIL G-3

SECTION H-H

SECTION U-U

SECTION P-P

SECTION U-U

SECTION T-T

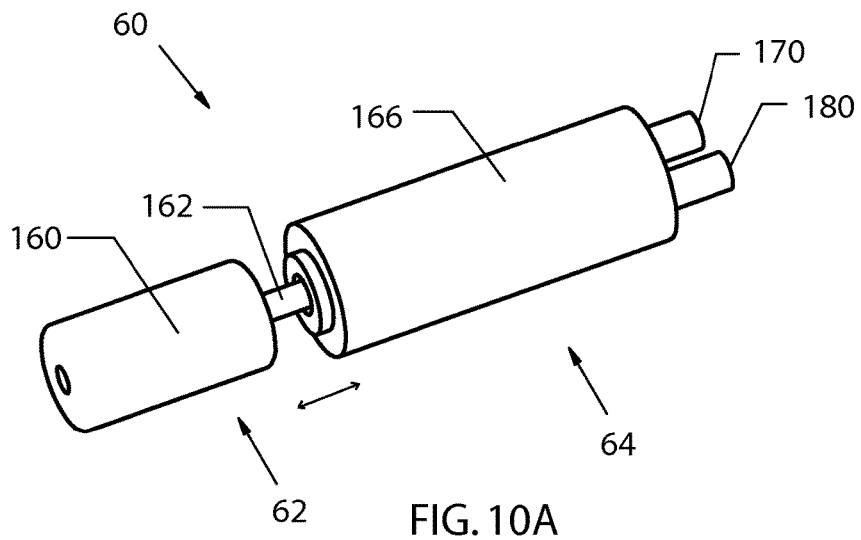
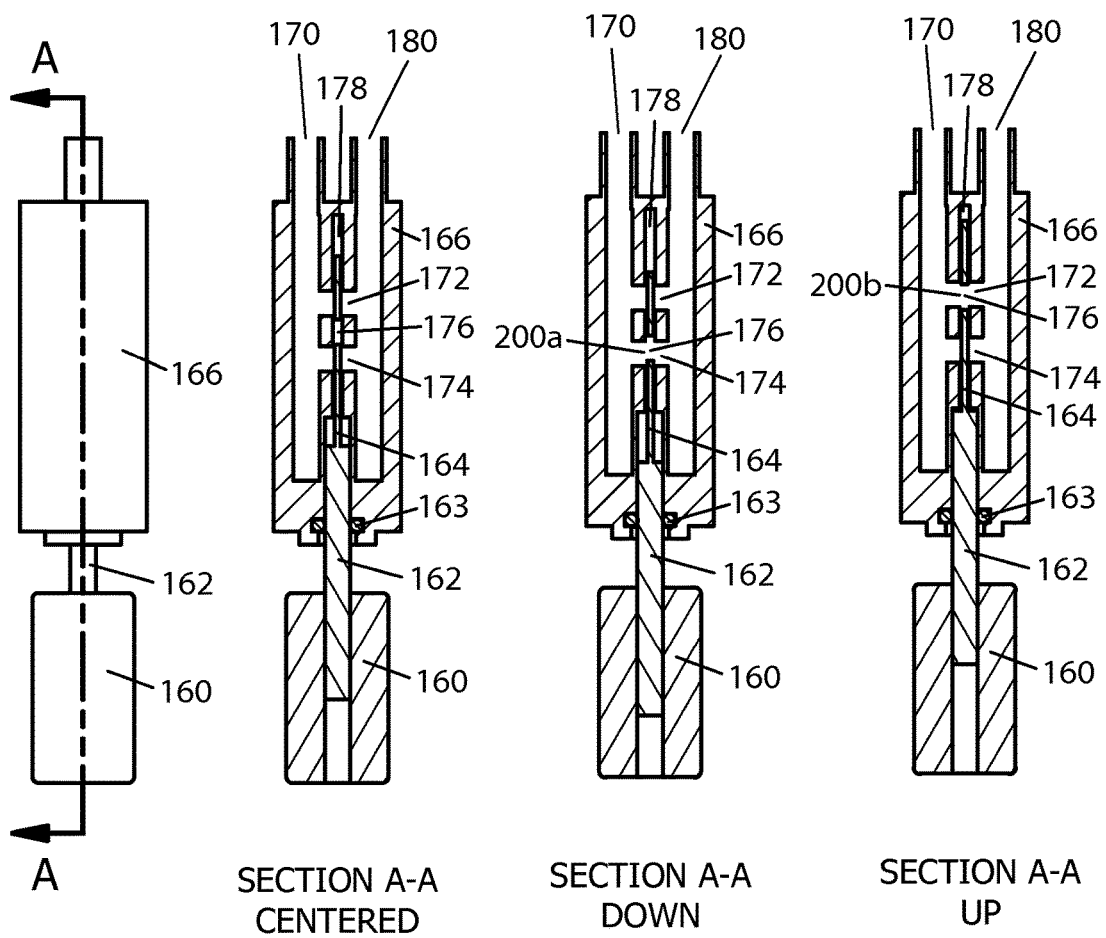
FIG. 10A
FIG. 10B — SECTION A-A CENTERED FIG. 10C — SECTION A-A DOWN FIG. 10D — SECTION A-A UP FIG. 10E

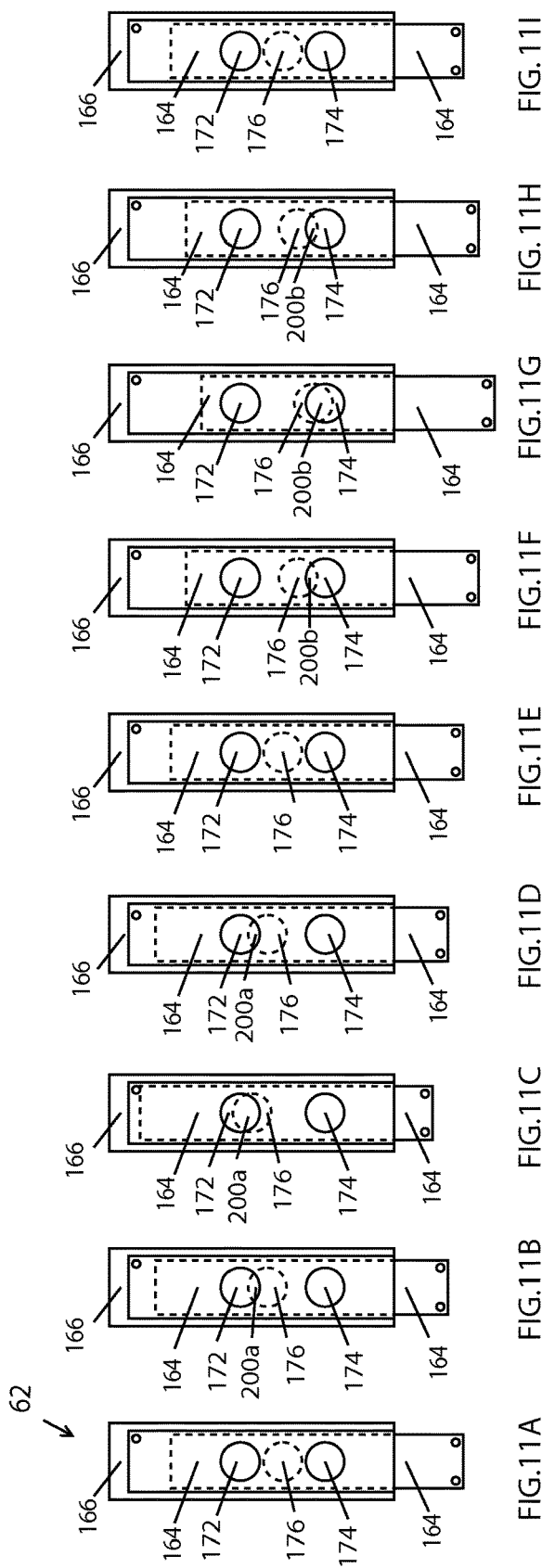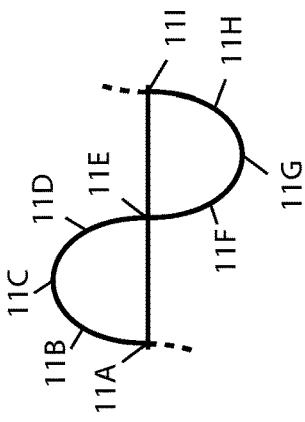

DETAIL F (SECTION)

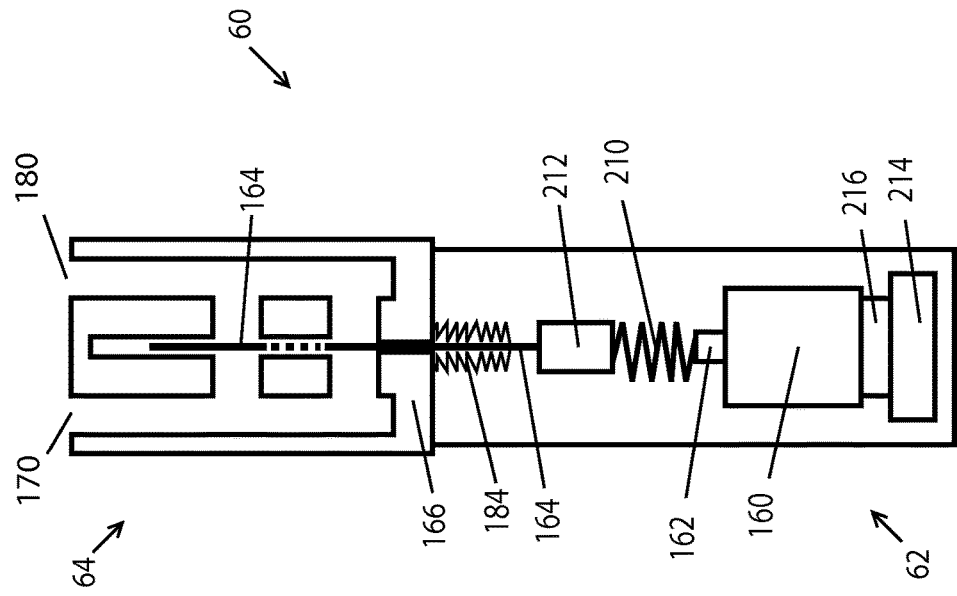
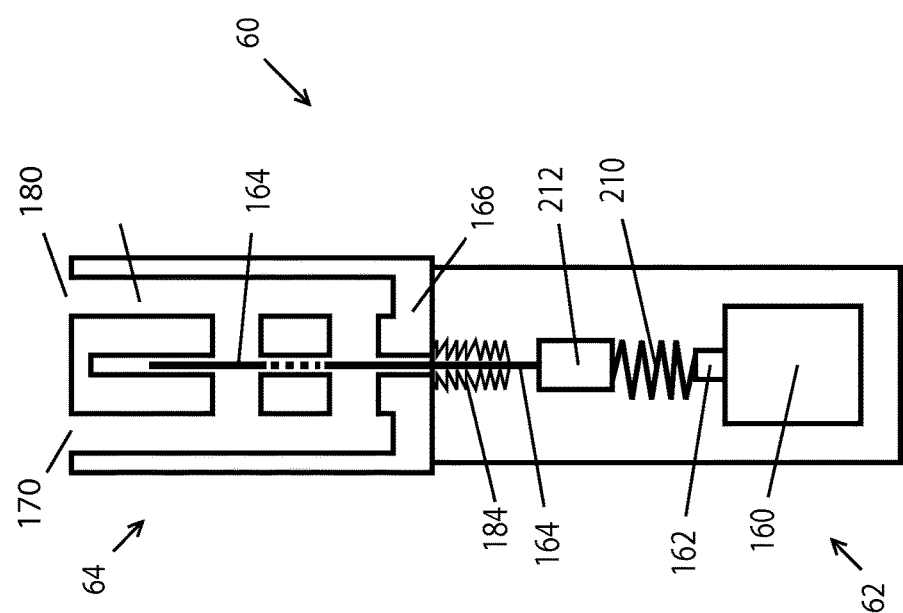

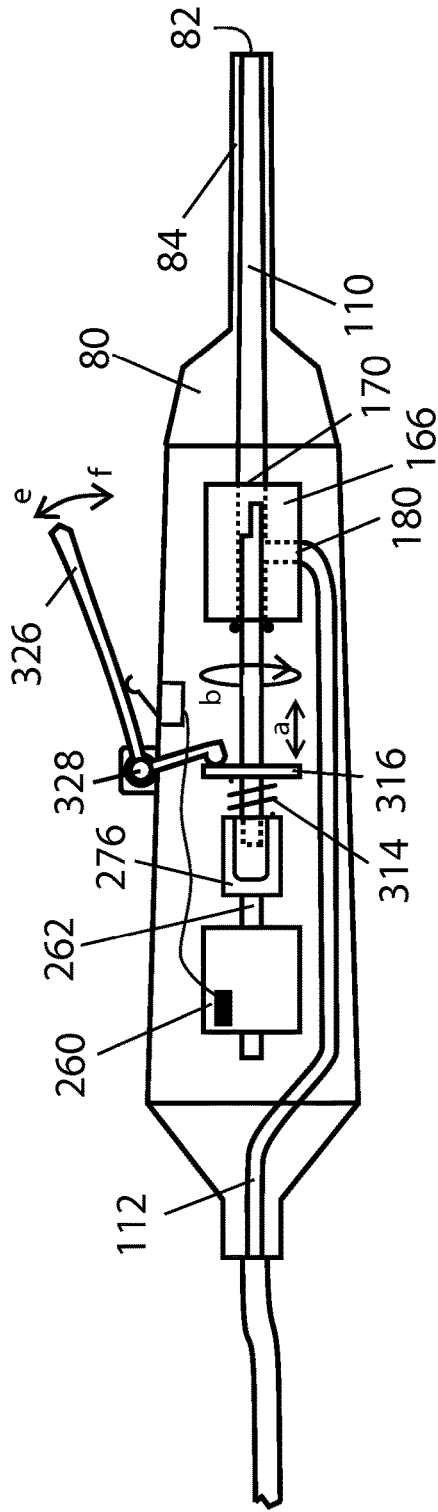
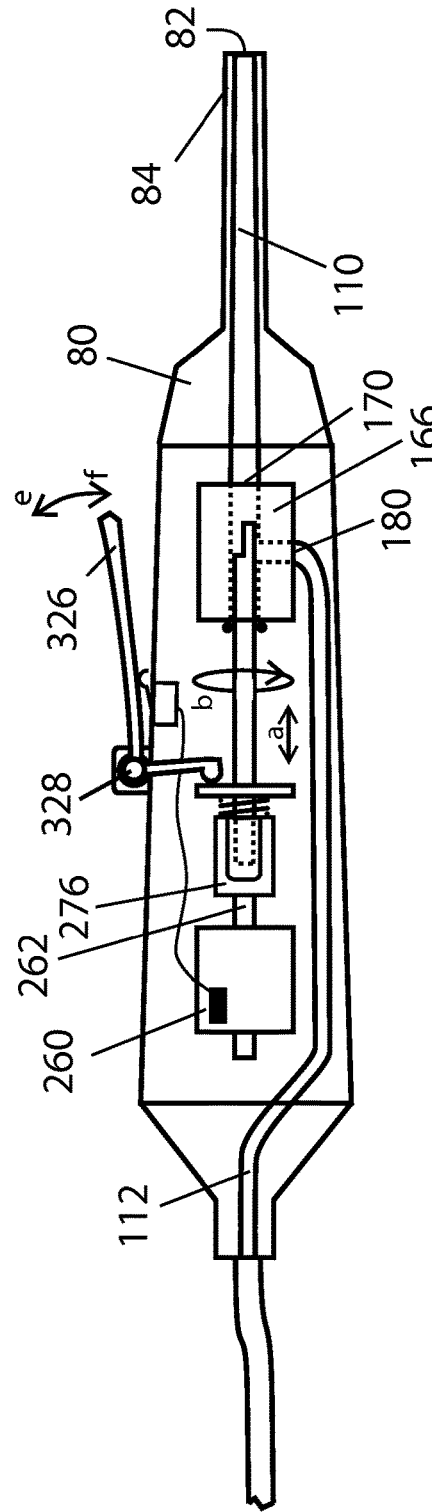
FIG.20A
FIG.20B

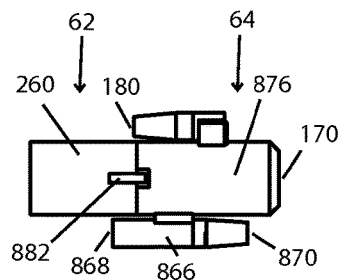
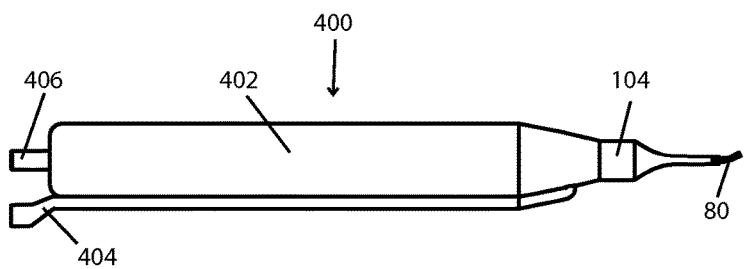
FIG. 22A  FIG. 22B
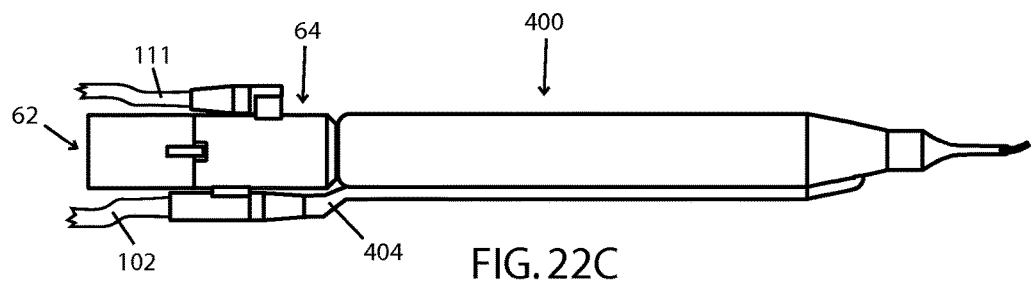
FIG. 22C
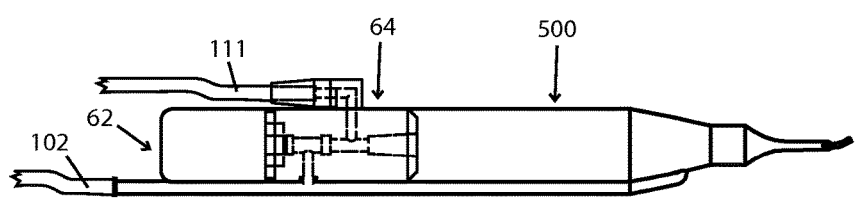
FIG. 22D

SECTION K-K

SECTION L-L

CYCLIC APERTURE FLOW REGULATOR SYSTEM

FIELD OF INVENTION

This invention relates to surgery, specifically to an improved flow regulation system that can be used with advantage in ocular surgery.

BACKGROUND

Various contemporary surgical procedures require aspiration of fluids that may contain solid or semi-solid tissue or other debris. In many cases, the fluids may need to be aspirated from a body cavity such as from within the lens capsule of the eye or a cavity in a joint such as the shoulder or the knee. It is typically desirable to maintain an ambient or a super-ambient pressure within the body cavity during such surgical procedures. For example, the lens of a human eye may develop a cataractous condition that affects a patient's vision. Cataractous lenses are sometimes removed and replaced in a procedure commonly referred to as phacoemulsification. Phacoemulsification procedures are typically performed with an ultrasonically driven surgical probe that is used to break the lens within the lens capsule of the eye. The broken lens is removed through an aspiration line that is coupled to the handpiece and protrudes into the lens capsule. The handpiece has a probe with a tip that is inserted through an incision in the cornea. The handpiece typically contains a number of ultrasonic transducers that convert electrical power into a mechanical oscillating movement of the tip. The distal end of the tip has an opening that is in fluid communication with the aspiration line. The distal end of the tip can also have a sleeve that has an opening in fluid communication with an irrigation line. The irrigation line is typically connected to a pressurized source of fluid that can provide irrigation fluid to the surgical site. The oscillating movement of the tip breaks the lens into small pieces. Lens fragments can also be aspirated without any use of ultrasonic power either using a conventional ultrasonic handpiece or a dedicated aspiration probe that can eventually incorporate an irrigation port, better known as an irrigation/aspiration and the same concerns exist about flow control and vacuum surges described later. The lens pieces and irrigation fluid are drawn into the aspiration line through as aspiration opening on the tip. Phacoemulsification is more likely to be successful if super-ambient pressure can be maintained within the lens capsule and the anterior chamber of the eye during the procedure. However, fluid surges can be created after the distal end of the aspiration line is cleared from momentary obstructions by solid or semi-solid tissue. These fluid surges, also known as post-occlusion surges, can lead to transient aspiration flow rates through opening of the distal end of the surgical probe can transitorily exceed the flow rate through the irrigation line thereby causing eye chamber instability and an eventual collapse of the surrounding tissue. This instability can compromise the safety of the procedure of the eye, with potential undesirable damage to the posterior aspect of the lens capsule of the eye, and/or endothelium cells to be undesirably drawn away from the cornea and towards the distal end the tip of the handpiece. On the other hand, too high an irrigation flow rate may undesirably move endothelium cells away from the cornea, or undesirably cause endothelium cells to be aspirated out of the eye. Conventional phacoemulsification procedures are typically performed using a vacuum pressure of about 350 mmHg. There is a desire to increase the vacuum pressure to assist in aspirating lens fragments faster and with less auxiliary energy such as ultrasound. Lowering the ultrasonic work would be desirable because ultrasound can irritate the eye. Moreover, recent introduction of femtosecond laser assisted cataract surgery (FLACS) allows a laser induced significant softening of the lens material in many cataract procedures, making the use of ultrasonic energy unnecessary, only relying in aspiration of the laser-softened lens tissue material. Consequently, there is a desire to apply vacuums above 500 mmHg to improve the efficacy of aspiration thus reducing the amount of ultrasound delivered inside the eye, or the ability to safely and efficiently aspirate ultrasonically emulsified, laser-softened lens material or primitively soft lens material. However, such higher vacuum exacerbate the surgical risks associated with post-occlusion fluid surges into the surgical probe. Also for example, some orthopedic medical procedures produce particles or other debris that must be removed from a cavity within a joint such as in the shoulder or knee. To remove such particles the surgeon may couple an aspiration tube to the surgical site. The aspiration tube, which pulls the debris from the body, is typically connected to a canister, which is connected to a suction tube connected to wall suction. To ensure that the surgical site is properly distended during surgery, relatively large quantities of irrigation fluid are typically introduced to the body to continuously irrigate the surgical site, and an infusion pump is typically required to offset the high flow created by the hospital vacuum line. The introduction of such amounts of irrigation fluid into the body can cause undesirable or excessive extravasation of irrigation fluid into the surrounding tissue. Also, post-occlusion surges can be created when the suction line is obstructed by solid or semi-solid tissue. Such post-occlusion surges can lead to transient aspiration flow rates through the hospital vacuum line that substantially exceed the flow rate of irrigation fluid and thereby cause a sub-ambient pressure to be momentarily applied to the surrounding tissue. The momentary sub-ambient pressure condition may cause partial collapse of the body cavity, damage to tissue near the distal end of the aspiration tube, and/or undesired tissue or fluid to be drawn towards the distal end of the aspiration tube. Surgical aspiration systems may be designed to allow the surgeon to temporarily reverse the direction of aspiration flow by depressing a reflux switch or bulb attached to the system. The surgeon may do this, for example, if tissue is drawn towards the distal tip of the aspiration tube or handpiece that the surgeon does not desired to be drawn (e.g. tissue that the surgeon does not want to be damaged by the distal tip). The surgeon may also initiate reflux to clear or dislodge an occlusion at the distal tip of the aspiration tube or handpiece. Contemporary post-occlusion surge limiters can limit the vacuum surges within the aspiration system, but only when the vacuum created by the vacuum pump is limited to a level that is safe in consideration of the diameter and length of that surge limiter. For example, considering the typical dimensions of needles and tubing used in ophthalmology, the flow that would be generated by a 500 mmHg vacuum is above 250 cc/min which can undesirably collapse the eye. Therefore, prior art systems that use a Venturi pump must operate modest vacuum levels, e.g. below 300 mmHg unless very small needle bores are used. Such modest vacuum levels significantly limit the available un-occluded flow in such systems. Therefore, such surge limiters are typically not used with peristaltic pumps that will significantly increase the pressure difference in response to an occlusion of the aspiration tip. The absence of pressure rise in response to occlusion in the contemporary aspiration systems limits their ability to aspirate large tissue particles. Also, an in-line surge limiter may reduce the maximum flow rate in the absence of occlusion, even when the surgeon would prefer a higher flow rate to draw certain tissue towards the distal end of the tip (rather than moving the distal end of the tip towards the tissue). Also, an in-line surge limiter can undesirably reduce the maximum reflux flow rate.

Therefore, it would be desirable to provide an aspiration line flow regulator system that maintains a stable ambient or super-ambient pressure within a body cavity during a surgical procedure by limiting vacuum surges in the system.

For example, it would be desirable to provide an aspiration line flow regulator system that is configured such that the flow rate out of the body cavity through the aspiration line does not greatly, or for a prolonged period, exceed the flow rate into the body cavity. In cataract surgery, for example, aspiration flow should be sufficient to quickly engage and aspirate lens particles from the eye, however in the event of an occlusion the high vacuum created in the aspiration line may temporarily produce too high a flow after the occlusion break which could collapse the eye and produce damage.

It would also be desirable to provide an aspiration line flow regulator system that functions safely with limited or reduced flow rate of irrigation fluid through the irrigation line even when using the highest vacuum levels available.

It would also be desirable to provide an aspiration line flow regulator system that can safely take advantage of an aspiration pump that can significantly increase the relative vacuum response to an occlusion.

It would also be desirable to provide an aspiration line flow regulator system that would allow a high aspiration flow rate in the absence of an occlusion, and a reflux feature when commanded by the operator.

It would also be desirable to provide an aspiration line flow regulator system that could allow the use with advantage of the maximum vacuum levels achievable with improved safety and efficacy.

It would also be desired to provide an aspiration line flow regulator system that allows an operator to accurately control the flow rate from a surgical site while maintaining high vacuum levels to, for example, slowly but powerfully aspirate tissue fragments, reducing the need of use of complementary tissue disrupting energies such as ultrasonic emulsification.

SUMMARY

A cyclic aperture flow regulator system is disclosed to prevent post-occlusion instability of a body cavity during surgical aspiration of fluid and tissue fragments through an aspiration opening of a surgical probe. The flow regulator system includes a flow regulator valve portion having a fluid aperture with adjustable cross-sectional area. The flow regulator valve has a valve chamber and a movable member both parts cooperating to define the dimensions of the fluid aperture by the extent of overlap between the movable member and the entrance to fluid passages disposed in the valve chamber. The flow regulator valve portion is inserted in the fluid path connecting the aspiration opening of the surgical probe with a vacuum source. An actuator portion is connected with the flow regulator valve portion and is operable to modify the cross-sectional area of the fluid aperture. A controller provides a command signal to the actuator portion to cause cycles of variation of the cross-sectional area of the fluid aperture with each cycle including at least one segment where the cross-sectional area of the fluid aperture is substantially reduced or eventually closed. The cycles of aperture dimensions fluctuation are set to occur at a frequency sufficiently high to produce a substantially steady flow through the surgical probe. Fluid and tissue fragments can be aspirated from the body cavity with the surgical probe without instability caused by fluid surges caused by occlusion breaks aspiration opening of the surgical probe. Flow can be regulated by adjusting the vacuum level in the conventional manner. Flow can also be adjusted by modifying the amplitude of the aperture modulation cycles and in this way changing the RMS (root mean square) value of the cross sectional area of the fluid aperture inside the valve portion of the flow regulator system.

BRIEF DESCRIPTION OF THE DRAWINGS

FIGS. 10A to 10E is a schematic representation of an oscillatory embodiment of the cyclic aperture flow regulator system of the present invention.

FIGS. 11A to 11J is a sequence of illustrations representing the displacement of a movable member having a window along one full cycle of oscillation with respect to a valve body having two fluid passages indicating the cross-sectional area of the resulting fluid aperture on each frame.

FIGS. 18A and 18B depict alternative embodiments of the active flow regulator from FIGS. 10A to 10B additionally including a spring-mass oscillating mechanism and a linear actuator (FIG. 18B).

FIGS. 20A and 20B are schematic illustrations of a manually controlled flow regulator system of the present invention enclosed within a handpiece.

FIGS. 22A to 22C illustrate an embodiment of the present invention that can be detachably coupled to a surgical handpiece of the prior art.

FIG. 22D illustrates an embodiment of the present invention that can be detachably coupled to a surgical handpiece carrying the actuator portion of the flow regulator system.

Figure 1A:
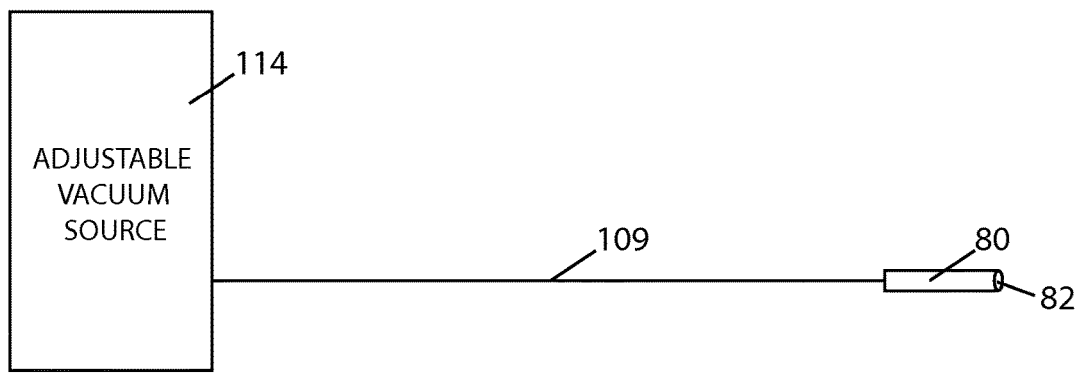
FIG. 1A is a schematic illustration of a surgical aspiration system of the prior art.

NUMBER LEGENDS 60 cyclic aperture flow regulator system
62 cyclic aperture flow regulator actuator portion
64 cyclic aperture flow regulator valve portion
68 tissue disruption actuator
70 surgical handpiece
80 surgical probe
82 aspiration port
84 probe shaft
86 probe hub
88 surgical probe attaching thread
90 irrigation valve
92 irrigation valve signal cable
100 fluid source
102 irrigation line
104 irrigation probe
106 irrigation pressure sensor
108 irrigation sensor cable
109 direct fluid path
110 first fluid path
111 aspiration tube
112 second fluid path
114 adjustable vacuum source
116 fluid waste deposit
118 vacuum control valve
120 venting valve
130 processor
132 cyclic aperture flow regulator controller
134 tissue disruptor driver
140 aspiration pressure sensor
142 actuator cable
143 flow regulator control cable
144 motion sensors cable
146 tissue disruptor driver cable
150 lensectomy console 160 oscillatory actuator
162 flow regulator oscillatory shaft
163 seal
164 oscillatory blade
166 valve portion body
170 valve input
172 first fluid passage
174 second fluid passage
176 fluid window
178 valve slit
180 valve output
184 sealing bellows
200 aperture with adjustable cross-sectional area
204 tissue fragment
206 passing tissue fragment
208 retained tissue fragment
210 Spring
212 Mass
214 linear actuator
216 actuator shaft
240 fixed aperture RMS handpiece
242 handpiece enclosure
247 male thread
248 female thread
249 actuator enclosure
258 screw
260 rotary motor
262 rotary motor shaft
264 rotary position sensor
270 linear actuator
272 linear actuator shaft
274 axial position sensor
276 coaxial rotary joint
280 driveshaft
282 bearing
284 bearing
290 valve rotor
292 valve chamber
294 rotor lid
295 Edge
296 rotor window
298 elastic membrane
299 membrane port
314 compression spring
316 Disc
326 Lever
328 pivot joint
330 secondary shaft
400 prior art handpiece
402 handpiece housing
404 irrigation tube
406 aspiration line connector
500 surgical handpiece
502 handpiece enclosure
504 irrigation tube
506 aspiration tube
508 irrigation sleeve
510 ultrasonic lensectomy probe
512 ultrasonic actuator
514 ultrasonic motion converter
516 magnet
518 hall effect rotary position sensor
520 "In-Tube" valve portion
522 handpiece axial tube
523 circulation space
524 shaft seal
525 shaft seal cover
526 shaft seal body
527 O-ring
528 bypass channel
530 fluid return port
600 surgical handpiece
610 surgical probe with partial valve portion and two fluid passages
634 fluid passage
638 outflow channel
710 surgical probe with partial valve portion and one fluid passage
770 first fluid path wave-integrator
772 second fluid path wave-integrator
773 bubble generator
774 bubble generator electrode
775 isolator plate
776 bubble generator driver
777 bubble injector tube
778 gas source
779 gas valve
780 gas bubbles
782 nozzle
784 electrode cables
786 bubble generator signal cable
788 bubble generator valve
800 oscillatory driven cyclic flow regulator handpiece
820 oscillatory "in-tube" valve portion
822 oscillatory shaft
824 in-tube piston for "in-tube" valve embodiment
826 piston window
828 piston ring
840 in-tube piston for "in-probe" valve embodiment
866 irrigation line bridge
868 irrigation bridge inflow port
870 irrigation bridge outflow port
872 irrigation fluid channel
874 irrigation fluid chamber
876 valve body
878 first O-ring
880 second O-ring
882 interlock
884 motor shaft key
886 rotor key
888 first O-ring seat
890 second O-ring seat
892 washer
894 valve tube
910 surgical probe with complete valve portion and one fluid passage
922 shaft distal feature
924 surgical probe rotor
926 rotor shaft matching feature
928 rotor window
930 spring
932 rotor retaining stricture
950 Surgical probe with valve and tissue fragmentation feature
952 Spur
954 valve rotor with internal tissue fragmentation feature
956 tissue fragmenting ribs in rotor
970 irrigation-aspiration handpiece with flow regulator system
972 aspiration probe
974 I/A handpiece distal enclosure
976 I/A handpiece proximal enclosure

DETAILED DESCRIPTION

For the purposes of promoting an understanding of the principles of the present disclosure, reference will now be made to the example embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances same reference numbers can be used throughout the drawings to refer to the same or like parts.

Shown in FIG. 1A is a schematic illustration of a surgical aspiration system of the prior art showing a fluid path 109 directly connecting an aspiration opening 82 of a surgical probe 80 with an adjustable vacuum source 114. FIG. 1C shows a surgical handpiece of the prior art 400 with a housing 402, an irrigation tube 404, an irrigation sleeve 104, an aspiration line connector 406 and surgical probe 80 attached at the distal end of handpiece 400. It can be seen in FIG. 1D showing hidden aspects of handpiece 400 that fluid path 109 traverses in direct tubular manner from the aspiration opening of surgical probe 80 to the aspiration line connector 406 traversing electro-mechanic ultrasonic actuator 512 and ultrasonic motion shifter 514. In the prior art the fluid path connecting aspiration line connector 406 with vacuum source 140 is contained within a single and direct aspiration tubing.

Figure 1B:
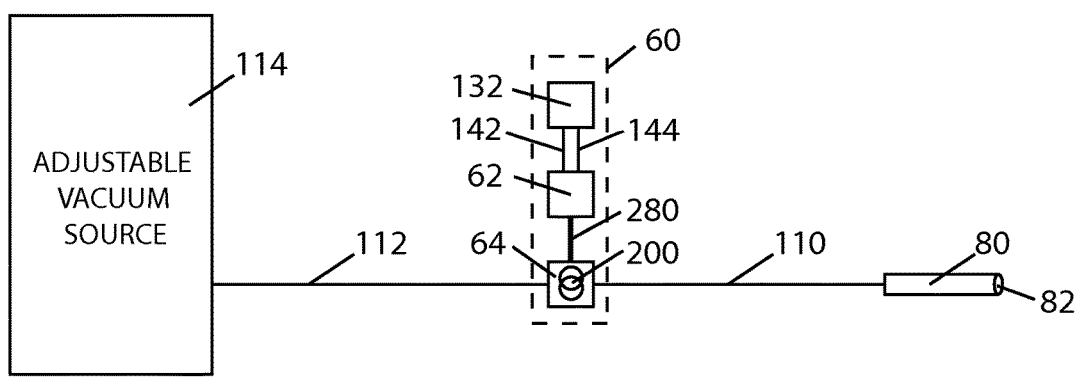
FIG. 1B is a schematic illustration of a surgical aspiration incorporating the cyclic aperture flow regulation system of the current invention.
Figure 1C:
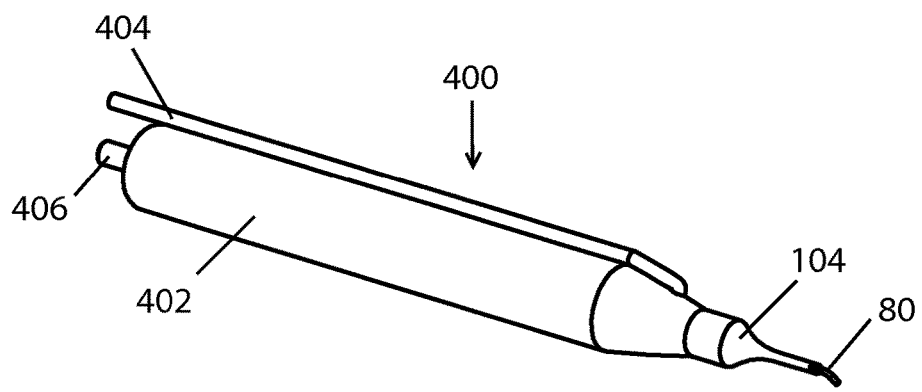
FIG. 1C is a perspective view of the exterior aspects of a surgical handpiece of the prior art.
Figure 1D:
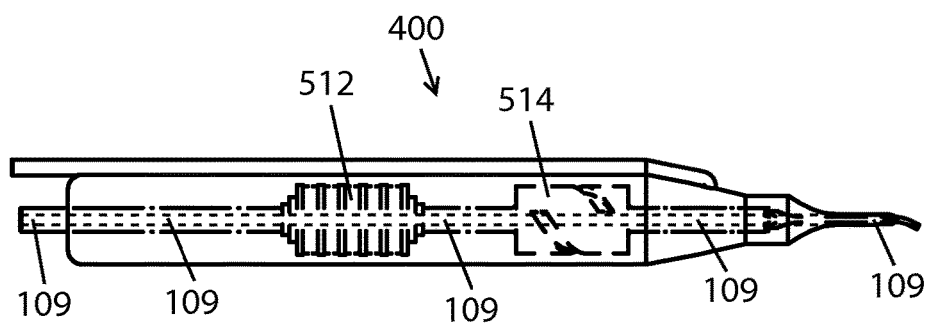
FIG. 1D is a side view of the handpiece from FIG. 1C exposing a continuous aspiration path.
Figure 1E:
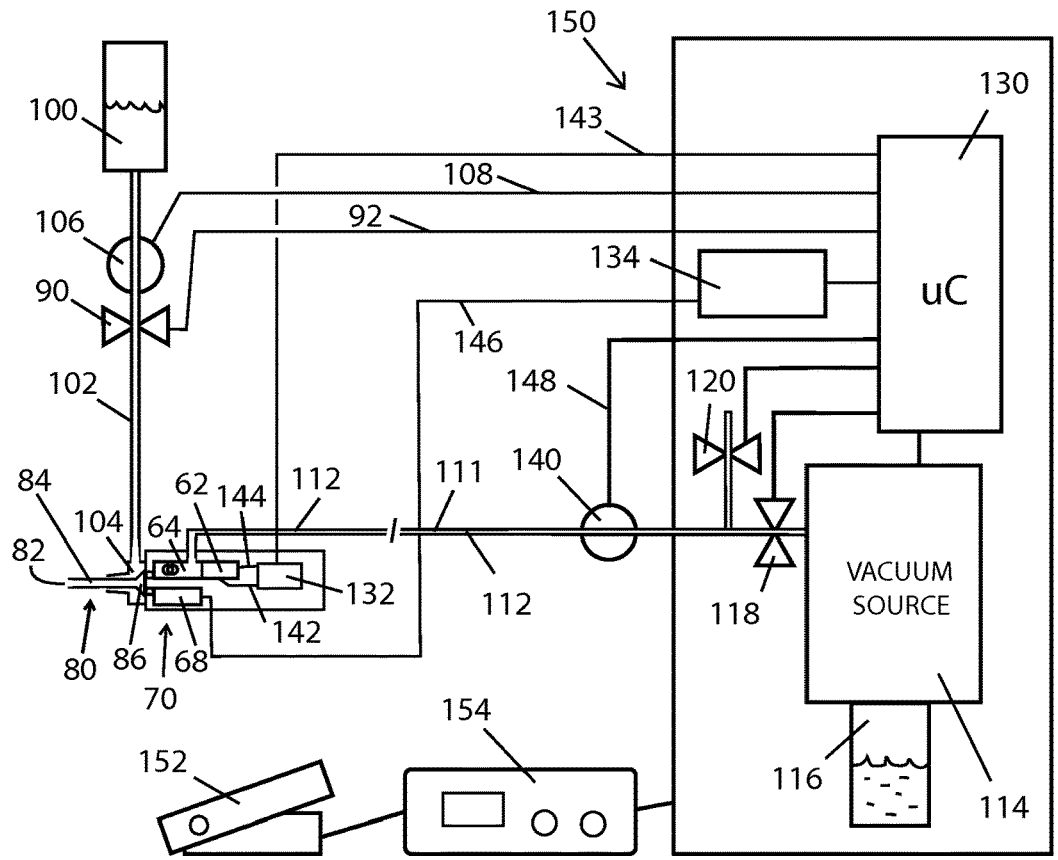
FIG. 1E is a schematic illustration of the cyclic aperture flow regulator system of the present invention incorporated into a phacoemulsification surgical console.
Figure 1F:
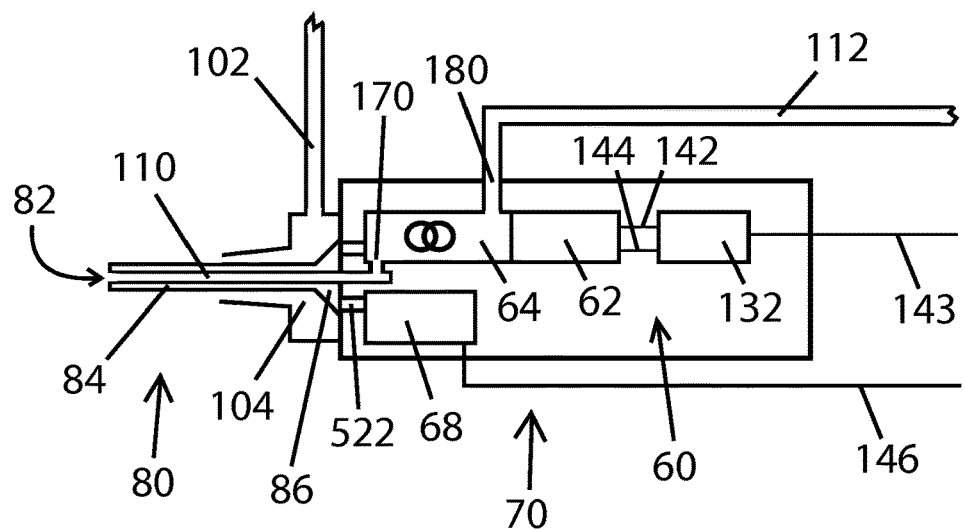
FIG. 1F is an expanded view of a handpiece portion from FIG. 1E.

FIG. 1B is a schematic illustration of a surgical aspiration system incorporating a cyclic aperture flow regulator system 60 of the present invention. A valve portion 64 of system 60 is inserted in the fluid path between aspiration opening 82 and adjustable vacuum source 114. The fluid path is divided into a first (pre-regulator) fluid path 110 and a second (post-regulator) fluid path 112, both fluid paths fluidly connected through an aperture with adjustable cross-sectional area 200 inside valve 64. An actuator portion 62 of system 60 operates a driveshaft 280 to modify the cross-sectional area of aperture 200. A controller 132 provides cyclic commands through an actuator cable 142 to actuator portion 62 to cause cycles of variation of the cross-sectional area of fluid aperture 200. Controller 132 commands actuator portion 62 to substantially reduce the cross-sectional area of fluid aperture 200 during at least one portion of each cycle, the substantial reduction of the cross-sectional area including the option of a transient complete closure of aperture 200. Motion sensors in actuator portion 62 can provide motion feedback signals to controller 132 through a motion sensors cable 144

Shown in FIG. 1C is a schematic illustration of a cyclic aperture flow regulator system 60 of the present invention incorporated into a surgical handpiece 70 of a lens removing console 150. Shown in FIG. 1D is an enlarged schematic view of the handpiece 70 region from FIG. 1C and its components. An irrigation line 102 connects a source of pressurized fluid 100 to a surgical site through an irrigation probe 104. An irrigation valve 90 can regulate flow between fluid source 100 and probe 104 into the eye. Surgical probe 80 has an aspiration port 82 that can be inserted into a surgical site such as the anterior chamber of the eye. Aspiration port 82 is in fluid connection through a hollow probe shaft 84 and a probe hub 86 with an input 170 of a valve portion 64 of cyclic aperture flow regulator system 60 located in surgical handpiece 70. Hub 86 also couples probe 80 with a tissue disruption actuator 68 inside handpiece 70 such that tissue disrupting energy can be effectively transmitted to probe 80 from tissue disruptor actuator 68 for lens disruption. First fluid path 110 is conformed between aspiration port 82 and aperture 200 including an input 170 of the valve portion 64 of flow regulator system 60. A reduced volume of first fluid path 110 is key for optimal performance of flow regulator system 60 when using high vacuum levels. Considering this observation, two preferred embodiments of flow regulator system have valve portion 64 of flow regulator system 60 located as near as practical to aspiration port 82 to reduce first fluid path 110 volume to a minimum.

First fluid path 110 is built with a cross-section preferably circular. Diameter should be equal or larger than the diameter of the fluid channel inside shaft 84 to prevent clogging this diameter typically ranging between 0.3 mm and 1.5 mm for a lensectomy probe. An output 180 of valve portion 64 of flow regulator system 60 is coupled to an aspiration tube 111 which travels a length to couple to vacuum source 114 within a surgical console 150. Second fluid path 112 is conformed between fluid aperture 200 and vacuum source 114 including output port 180 and aspiration tube 111. Vacuum source 114 has attached a fluid waste deposit 116.

A vacuum control valve 118 is inserted in second fluid path 112 to enable and disable vacuum available at output port 180. Valve 118 is commanded by processor 132. A venting valve 120 connects a lateral branch of second fluid path to an ambient or super-ambient pressure. Venting valve 120 can be activated by processor 132 to cancel vacuum inside second fluid path 112 and also to allow reflux operations requested by an operator. An irrigation line pressure sensor 106 can be installed in irrigation line 102. An aspiration line pressure sensor 140 can be installed in aspiration line 111. Cyclic aperture flow regulator system controller 132 can receive commands from processor 132 through a flow regulator control cable 143. An irrigation line pressure sensor signal cable 108 connects sensor 106 with controller 132. An irrigation valve signal cable 92 connects controller 132 with valve 90. Controller 132 operates a tissue disruptor actuator driver 134. Tissue disruptor driver 134 provides driving signals to tissue disruptor actuator 68 through a cable 146. Aspiration line pressure sensor 140 provides a pressure signal to controller 132 through a cable 148.

Handpiece with Axially Adjustable Rotor and "In-Tube" Valve Portion

FIGS. 2 to 8 illustrate different aspects of a preferred embodiment of the present invention. As seen in FIG. 2A, the cyclic aperture flow regulator system 60 of the present invention is composed by actuator portion 62 and by valve portion 64 with a valve portion body 166. A flow regulator driveshaft 280 transmits mechanical energy from actuator portion 62 to valve portion 64. Actuator portion 62 is composed by a rotary motor 260 having a rotary shaft 262 and by a linear actuator 270 having an axially displacing shaft 272. Rotary motor 260 speed can be adjustable between 5.000 and 30.000 RPM. Linear actuator 270 has a loaded response time of 50 milliseconds when driven using a properly tuned PID controller. Driveshaft 280 receives rotary motion from rotary motor shaft 262 through a coaxial rotary joint 276. Driveshaft 280 also receives axial motion from linear actuator 270 through actuator shaft 272. Bearings 282 and 284 allow driveshaft 280 to freely rotate inside linear actuator shaft 272 while restricting any significant axial play between driveshaft 280 and shaft 272. In this way, precise axial motion can be transferred to driveshaft 280 from linear actuator 270. A rotary position sensor 264 can detect motor shaft 262 angular position and provide an angular position signal to controller 132 through a cable 144. An axial position sensor 274 can detect flow regulator driveshaft 280 axial position and provide a shaft axial position signal to controller 132 through cable 144. Driveshaft 280 mechanically connects actuator portion 62 with valve portion 64. A valve rotor 290 is housed within a valve chamber 292 inside valve body 166 of valve portion 64 both rotor 290 and chamber 292 built with precise matching dimensions to allow axial and rotary displacement of rotor 290 inside chamber 292 without significant friction and at the same time with minimal leakage.

Figure 2A:
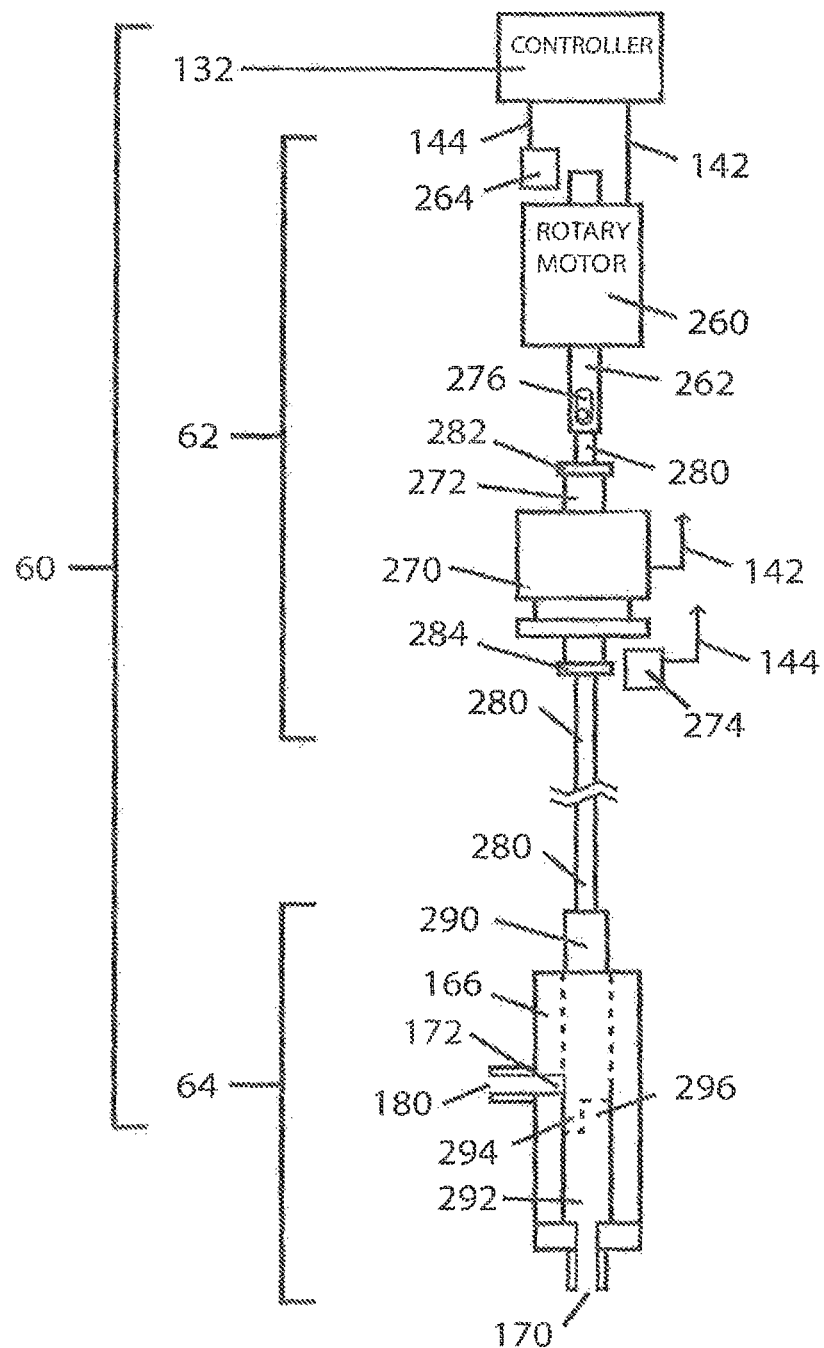
FIG. 2A is a schematic illustration of one preferred rotary-axial embodiment of a flow regulator system of the present invention.
Figures 2B, 2C, 2D:
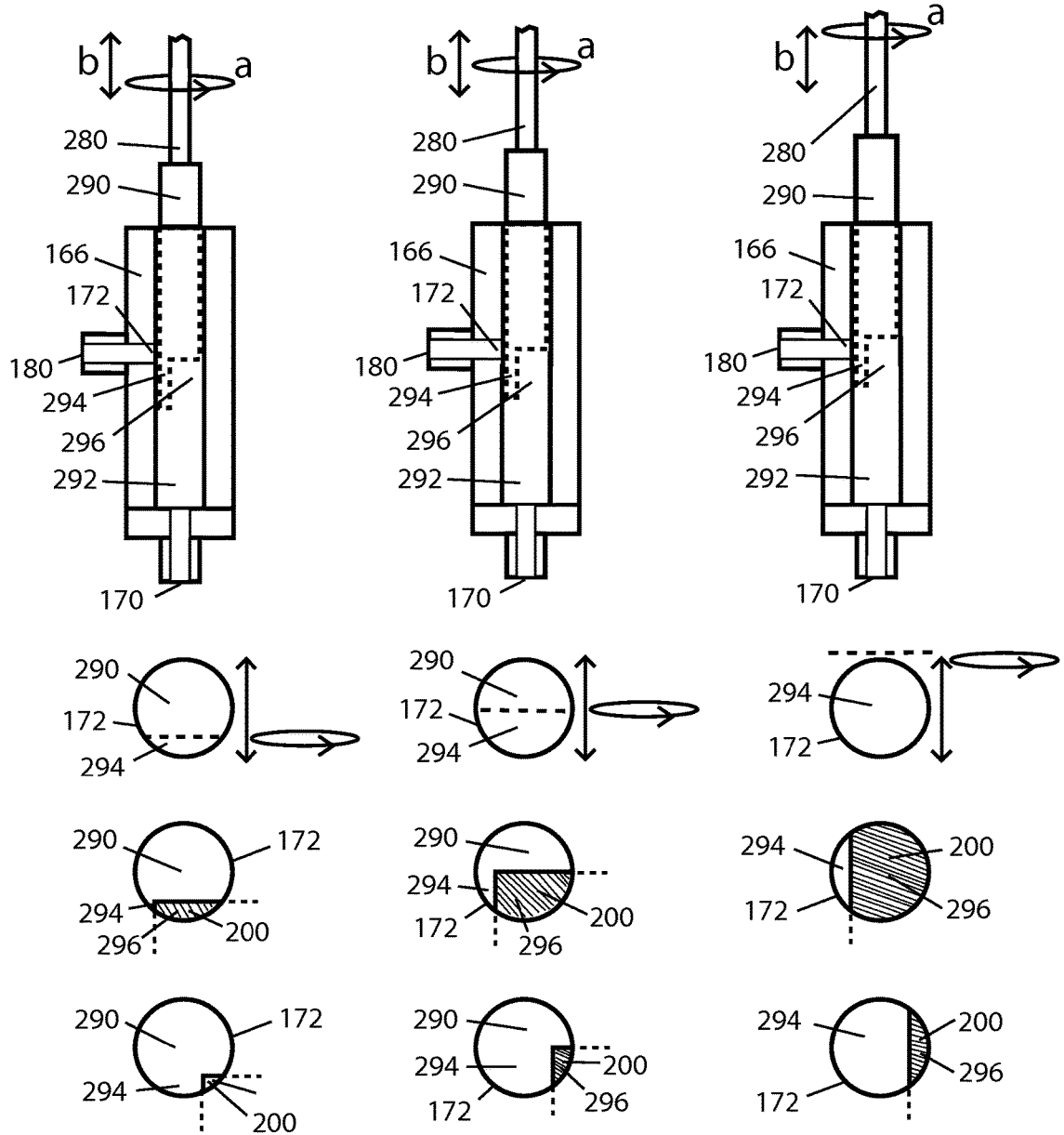
FIGS. 2B to 2D are schematic illustrations of the flow regulator system from FIG. 2A depicting exemplary aperture cross-sections that can occur during operation.

Valve chamber 292 is in fluid connection with valve input port 170. Valve chamber 292 is also in fluid connection with output port 180 through at least one fluid passage 172. Valve rotor 290 can have at least one lid 294 and at least one window 296 slidably in contact with the surface of chamber 292 where the entrance to passage 172 is located. Cross-sectional area of aperture 200 is configured by the overlay between lid 294 and window 296 both integral parts of rotor 290 and the entrance of passage 172. As shown in FIGS. 2B to 2D, depending on the relative axial and rotary position of rotor 290 with respect to body 166, lid 294 can partially or totally occlude fluid passage 172. Circular arrow "a" illustrates the rotary motion of driveshaft 280 and rotor 290. Linear arrow "b" illustrates the axial motion of driveshaft 280 and rotor 290. A fluid aperture 200 is determined by the relative position between lid 294 of rotor 290 and the entrance of fluid passage 172. Cross-sectional area of fluid aperture 200 is maximal when lid 294 does not overlap with any portion of the entrance of fluid passage 172. Cross-sectional area of fluid aperture 200 is minimal when a portion of lid 294 and/or of rotor 290 completely overlaps with the entrance of fluid passage 172 producing a substantial limitation to flow between ports 170 and 180 eventually determining a no-flow condition. A continuous range of intermediate aperture 200 dimensions are possible when partial occlusion of passage 172 occurs by different axial and rotary positions of rotor 290 with lid 294. In FIG. 2B valve rotor 290 is axially displaced into body 166 about ¾ of the full length that would otherwise totally cover fluid passage 172 in any rotary position. Three vertically disposed circles represent three different rotary positions of rotor 290 to exemplify three possible aperture 200 magnitudes along one revolution of rotor 290 in the depicted axial position.

In the top circle, rotor 290 and lid 294 in combination totally obliterate fluid passage 172 with aperture 200 being substantially closed or non-existent. The middle circle from FIG. 2B represents another rotational position of rotor 290 where lid 294 is minimally present in a way that mostly window 296 overlaps with passage 172 determining a moderate cross-sectional area of aperture 200. The lower circle from FIG. 2B shows another exemplary rotational position of rotor 290 that determines a very small aperture 200. Window 296 is the complementary cylinder portion of lid 294 that allows flow into passage 172 contributing to conform aperture 200. In the vertically arranged circles from FIG. 2C are represented similar rotor 290 rotational positions to the counterparts from FIG. 2B in this case with an axial position of rotor 290 that determines a an occlusion of about half the area of passage 172 entrance in any rotary position of rotor 290, leaving the other half of passage 172 entrance to be clear from obstruction or partially or totally occluded by lid 294 depending on the rotary position of rotor 290. The maximum aperture dimensions achievable during one revolution of rotor 290 are larger in FIG. 2C than in FIG. 2B. FIG. 2D is similar to 2B and 2C only that rotor 290 is axially positioned in a way that the only portion of rotor 290 that can overlap with passage 172 entrance during one revolution is lid 294. With rotor 290 in this axial position aperture 200 can reach the maximum possible cross-sectional area during one revolution of rotor 290 equivalent to the full aperture area of fluid passage 172 entrance.

Figure 3A:
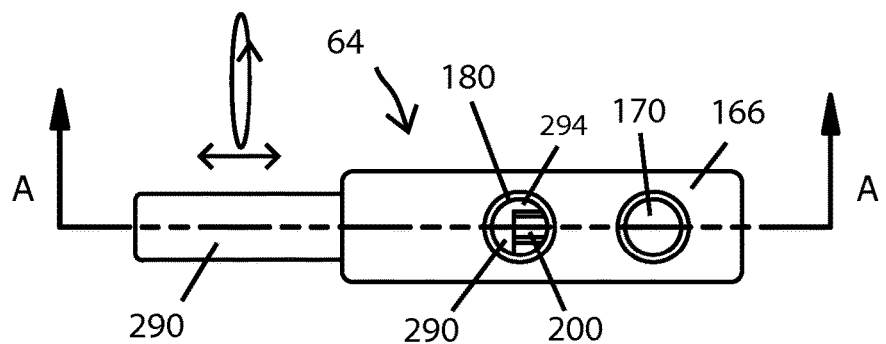
FIGS. 3A to 3D are sectional illustrations of a model of the flow regulator system from FIG. 2.
Figure 3B:
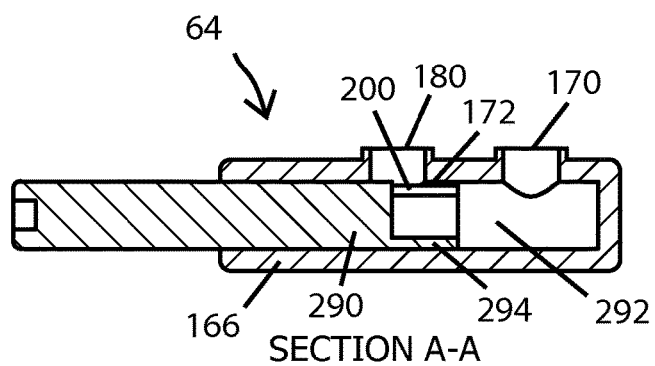
Figures 3C, 3D:
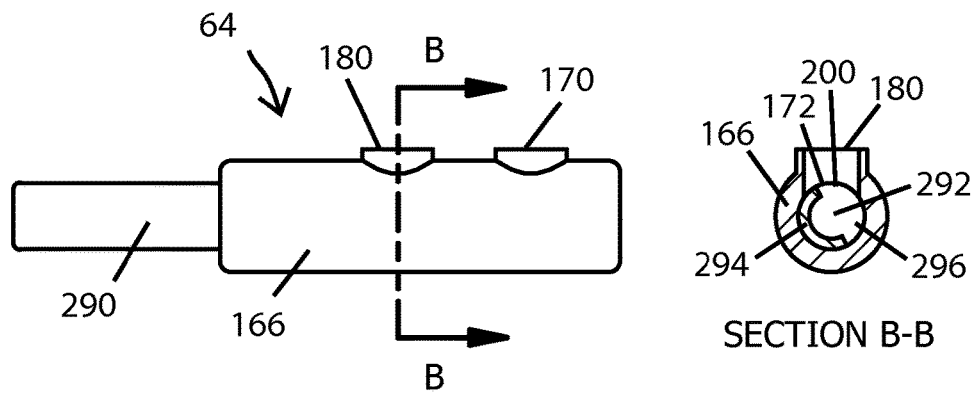
Figure 3E:
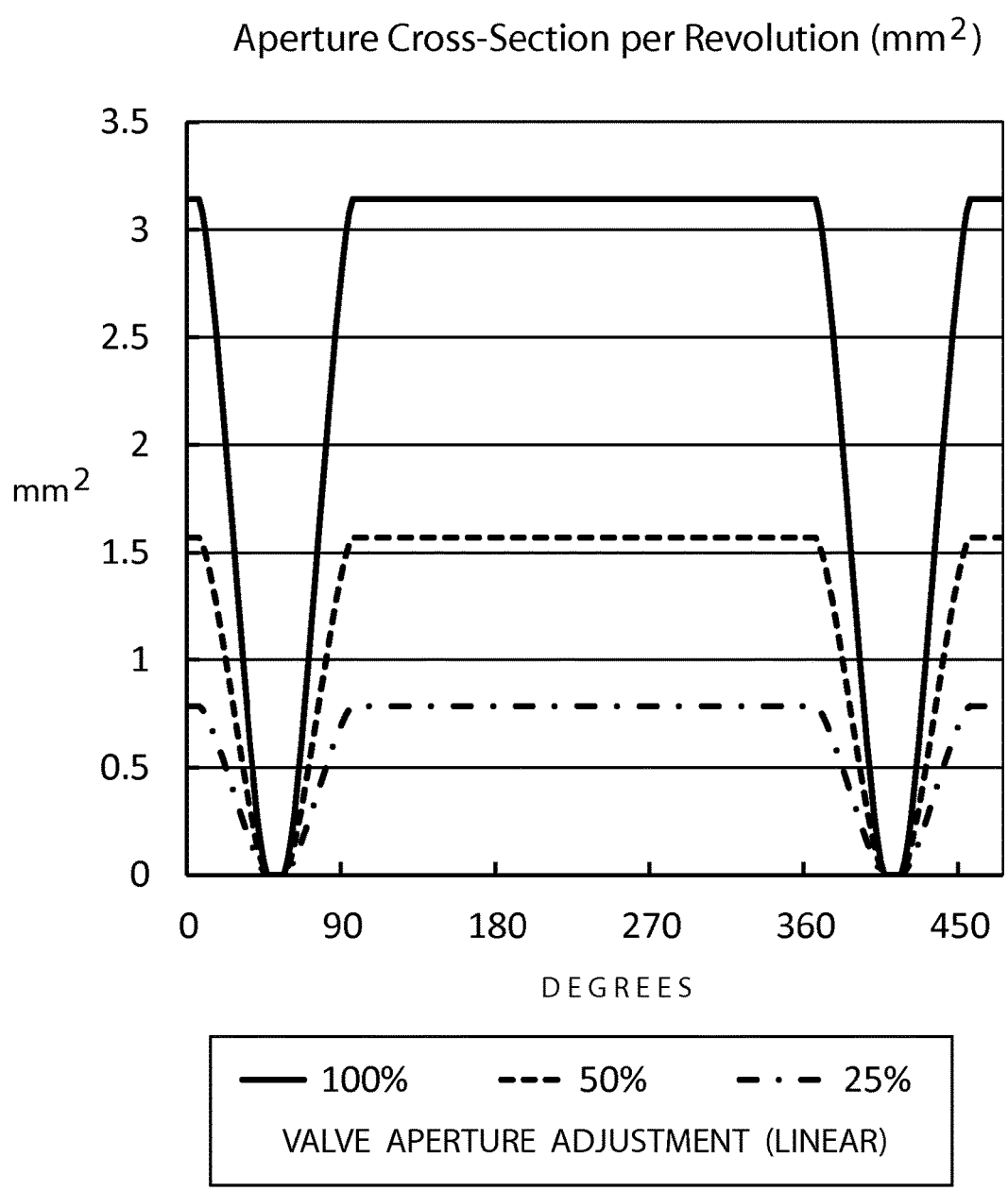
FIG. 3E is a graph illustrating the cross-sectional area of the adjustable fluid aperture along one revolving cycle of the flow regulator system matching with each of the examples shown in FIGS. 2B to 2D.

In FIGS. 3A to 3D are provided sectional views of valve portion 64 with rotor 290 in a particular axial rotary and axial position with respect to body 166 to illustrate how the magnitude of a fluid aperture 200 is determined by a combination of both the an axial and the rotary position of rotor 290. Although not necessarily planar, the narrowest aperture area is measured as the cross sectional area of aperture 200. FIG. 3E is a graph representing the aperture 200 dimensions versus rotor 290 rotary position while axially revolving rotor 290 inside valve chamber 292 along at least one revolution (degrees shown in X axis) in approximate correspondence with the examples provided in FIG. 2B (bottom tracing on the graph), FIG. 2C (middle tracing) and FIG. 2D (top tracing) for a circular fluid passage 172 entrance of radius=1 mm.

FIGS. 4A to 4K are representations of a surgical handpiece 500 for the removal of the crystalline lens from within an eye incorporating the cyclic aperture flow regulator system 60 of the present invention. Enclosure 502 accommodates and provides support for the interior components of handpiece 500. Irrigation line 102 is in fluid communication with an irrigation tube 504 which in turn connects with an irrigation probe 104 in the form of a coaxial irrigation sleeve 508. An aspiration tube 506 is in fluid communication with aspiration tube 111. An ultrasonically operated lensectomy probe 510 is fluidly and mechanically attached to handpiece 500 similar to probe 80 from FIG. 1.

Figure 4A:
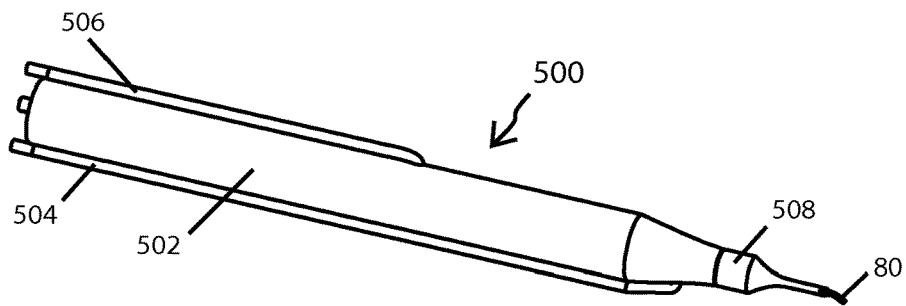
FIGS. 4A to 4K correspond to different perspective, detail and sectional views of one implementation in a surgical handpiece of the rotary-axial embodiment shown in FIG. 2A of the cyclic aperture flow regulator system.
Figure 4B:
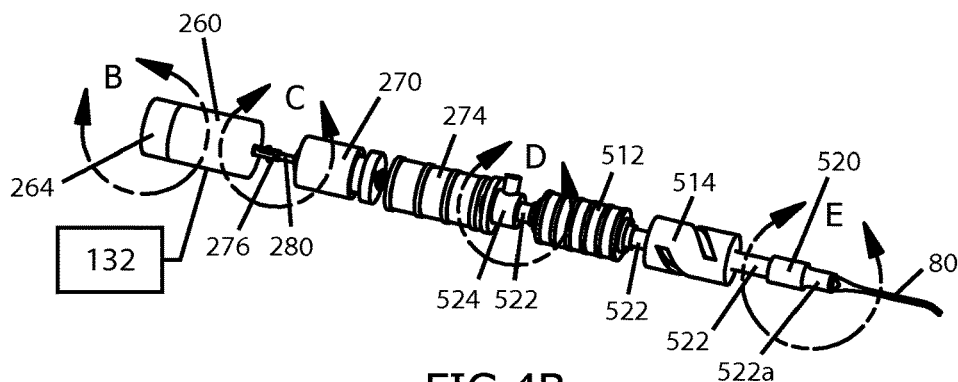
Figure 4C:
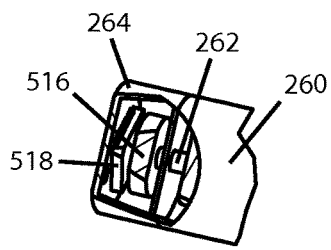
Figure 4D:
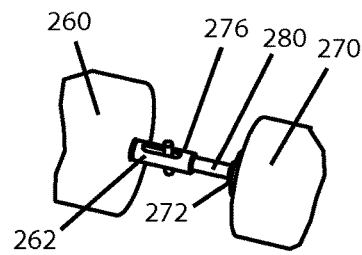

FIG. 4B shows the interior components of handpiece 500 as would be seen with enclosure 502 removed. An axial tube 522 has affixed an ultrasonic actuator 512 and an ultrasonic motion converter 514. A valve portion 520 is installed in tube 522 that corresponds with valve portion 64 from FIG. 1 conformed inside tube 522 ("In-Tube" configuration of valve 64). Lensectomy probe 510 is detachably connected both fluidly and mechanically with the distal end of tube 522 by means of a thread 88. The proximal end of tube 522 is connected with a shaft seal 524. Tube 522 interiorly contains axially disposed driveshaft 280 leaving a circulation space 523 between the outer diameter of driveshaft 280 and the inner diameter of tube 522 sufficient for expedite circulation of fluid and tissue fragments aspirated through probe 510. Driveshaft 280 crosses shaft seal 524 in watertight and gastight conditions to mechanically interconnect with rotary shaft 262 of rotary motor 260 though a coaxial rotary joint 276 (FIG. 4D). The opposite end of shaft 262 has attached rotary position sensor 264. Rotary position sensor 264 is composed by a radially magnetized circular magnet 516 fixated to the opposite end of motor shaft 262 and by a hall-effect rotary position sensor 518 (MELEXIS MLX90316 absolute rotary position sensor IC) (FIG. 4C).

Linear actuator 270 has shaft 272 coaxially mounted over driveshaft 280 providing driveshaft 280 freedom to rotate with respect to shaft 272 with no significant axial play as previously described. Linear motion sensor 274 consists in a linear variable differential transformer or LVDT (Measurement Specialties Series MHR+/−0.64 mm). Axial sensor 274 has a central hollow tube that is coaxially mounted around driveshaft 280 to allow non-contact axial and rotary displacements of driveshaft 280 with respect to sensor 274 while effectively measuring axial displacement of driveshaft 280. Among many alternatives for selecting axial sensor 274 are linear hall-effect sensors such as MELEXIS MLX90292 and linear optical quadrature encoders. Actuators 260 and 270 together with sensors 264 and 274 compose actuator portion 62 of cyclic aperture flow regulator system 60.

Figure 4E:
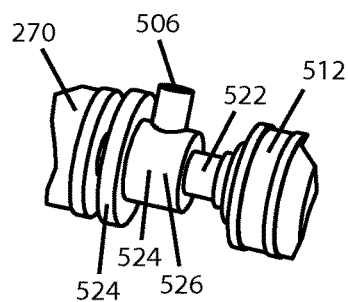
Figure 4F:
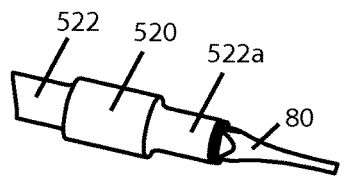
Figure 4G:
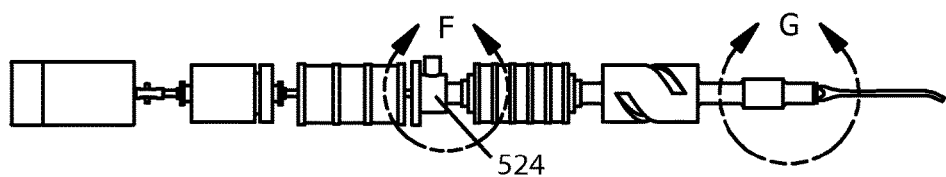
Figure 4H:
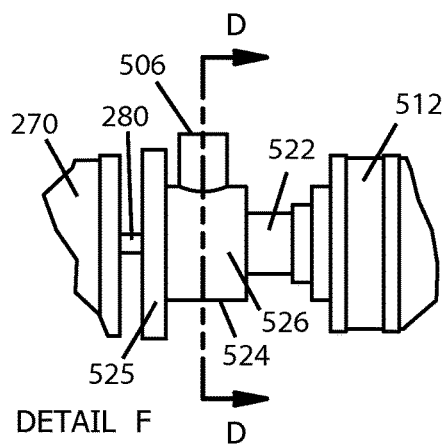
Figure 4I:
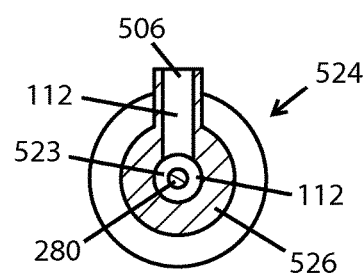

A detail of shaft seal 524 is shown in FIGS. 4E and 4H illustrating a shaft seal body 526 and a shaft seal cover 525 containing an O-ring 527 adjusted around driveshaft 280 (not shown). Shaft seal 524 allows low resistance watertight and airtight rotation and axial displacements of driveshaft 280 with respect to tube 522. Shaft seal 524 also contributes to fluidly connect the interior of tube 522 with aspiration tube 506 contributing to conform second fluid path 112 that fluidly communicates valve portion 520 with vacuum source 114.

Figure 4J:
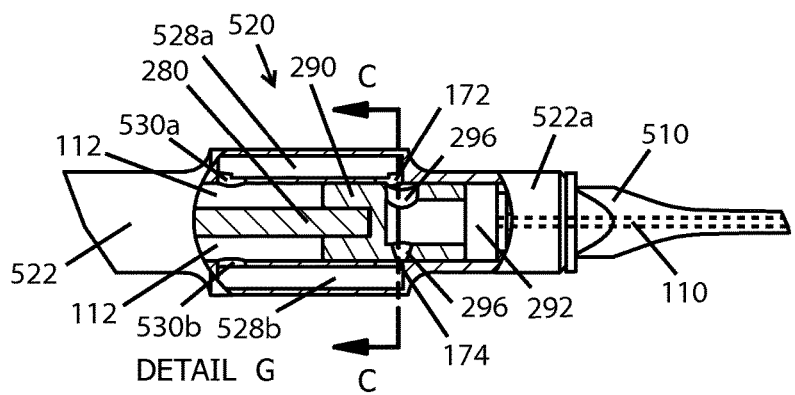
Figure 4K:
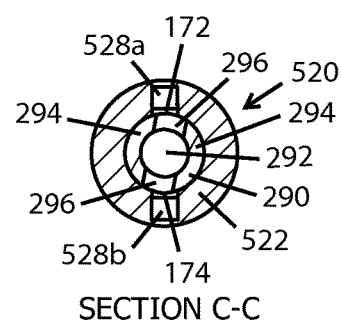

Detail G in FIG. 4G encircles "in-tube" valve portion 520 implemented inside tube 522 and is better illustrated in FIGS. 4J and 4K. FIG. 4J depicts a detail cutaway view of valve portion 520 integrated into a segment of tube 522. The portion of tube 522 that is left distal to valve 520 is labeled 522a and contributes to compose first fluid path 110. Cylindrical valve chamber 292 accommodates matching rotor 290 coupled to shaft 280 and enabled to rotate axially and to displace axially having two degrees of freedom (2 DOF) following driveshaft 280 rotary and axial movements as driven by actuators 260 and 270.

Probe 80 aspiration port 82 is in direct unobstructed fluid communication with valve chamber 292 through probe shaft 84, probe hub 86 and through distal portion 522a of tube 522 composing first fluid path 110. Fluid passage 172 and a symmetrically disposed second fluid passage 174 are in direct unobstructed fluid communication with the proximal interior of tube 522 across bypass channels 528a and 528b and through return ports 530a and 530b being all these fluid channels integral part of second fluid path 112. Channels 528 and return ports 530 can be functionally replaced by one or more channels etched on the inner wall of tube 522 using rotor 290 outer surface to complete the fluidic structure.

Aperture 200 defines the connecting boundary between first fluid path 110 and second fluid path 112. Valve chamber 292 can be fluidly connected with second fluid path 112 only when rotor 290 is disposed by driveshaft 280 in an axial and rotary position that allows a patent aperture 200 as illustrated in FIGS. 2 and 3. A variably sized fluid aperture 200 is determined by the extent of overlay between the entrance of fluid passages 172 and 174 and the fluid passage obstructing parts of rotor 290 including rotor body and lid 294. Non-blocking parts of rotor 290 are signaled as window 296. FIG. 4K is a cross sectional view extracted from FIG. 4J for better visualization of the rotational relationship between rotor 290 and chamber 292. It can be appreciated that during a single revolution of rotor 290 a fluidic aperture 200 can vary between maximum aperture and minimum aperture dimensions (cross-sectional area) producing a substantial variation in potential flow across the device. Aperture 200 dimensions can also vary between maximum aperture and minimum aperture with axial displacement of rotor 290. In this way a combination of axial and rotary displacements of rotor 290 can modify the cross-sectional area of fluidic aperture 200 between minimal and maximal. "In-Tube" valve portion 520 is illustrated in these figures as having a diameter larger than the diameter of tube 522 for better understanding. However, all the descripted fixed fluid channels from valve 520 can be carved or etched inside tube 522 without affecting its external diameter with similar performance. FIG. 8K is an expanded view of handpiece 500 to better illustrate the relationship between components inside valve portion 520, mainly driveshaft 280 and rotor 290.

The cyclic reduction of fluid aperture 200 cross-sectional area stops post-occlusion surges in a similar way an escapement mechanism in a clock avoids the escape wheel from accelerating progressively, also similar to engine braking that can stop a vehicle from running out of control. With valve 64 operating al low frequency, discrete "slices" of fluid are allowed to go through aperture 200 during each cycle. Increasing frequency of operation reduces the volume of these slices as well as the time separation between them. At a high enough frequency of operation of valve 64 aperture cycling the fluid "slices" merge into a continuum flow. When using high vacuum levels, cavitation inside first fluid path 110 together with fluid path resistance conform a fluidic R-C circuit that operates as an integrator of the pressure and flow waves producing a steady level provided the frequency of the aperture reduction cycles is sufficiently high. This is one reason why increasing the frequency of the cycles substantially eliminates ripple from the pressure and flow waveforms. Fluid aperture cross-sectional area cycling that includes a substantial reduction of aperture dimensions during each cycle effectively limits maximum flow and prevents post-occlusion surges. The total volume of the summed cavitation bubbles inside first fluid path 110 is a determinant of the magnitude of post-occlusion surges. The smaller the volume of first fluid path 110, the smaller the magnitude of eventual post-occlusion surges in the system at maximum vacuum levels.

Figure 17:
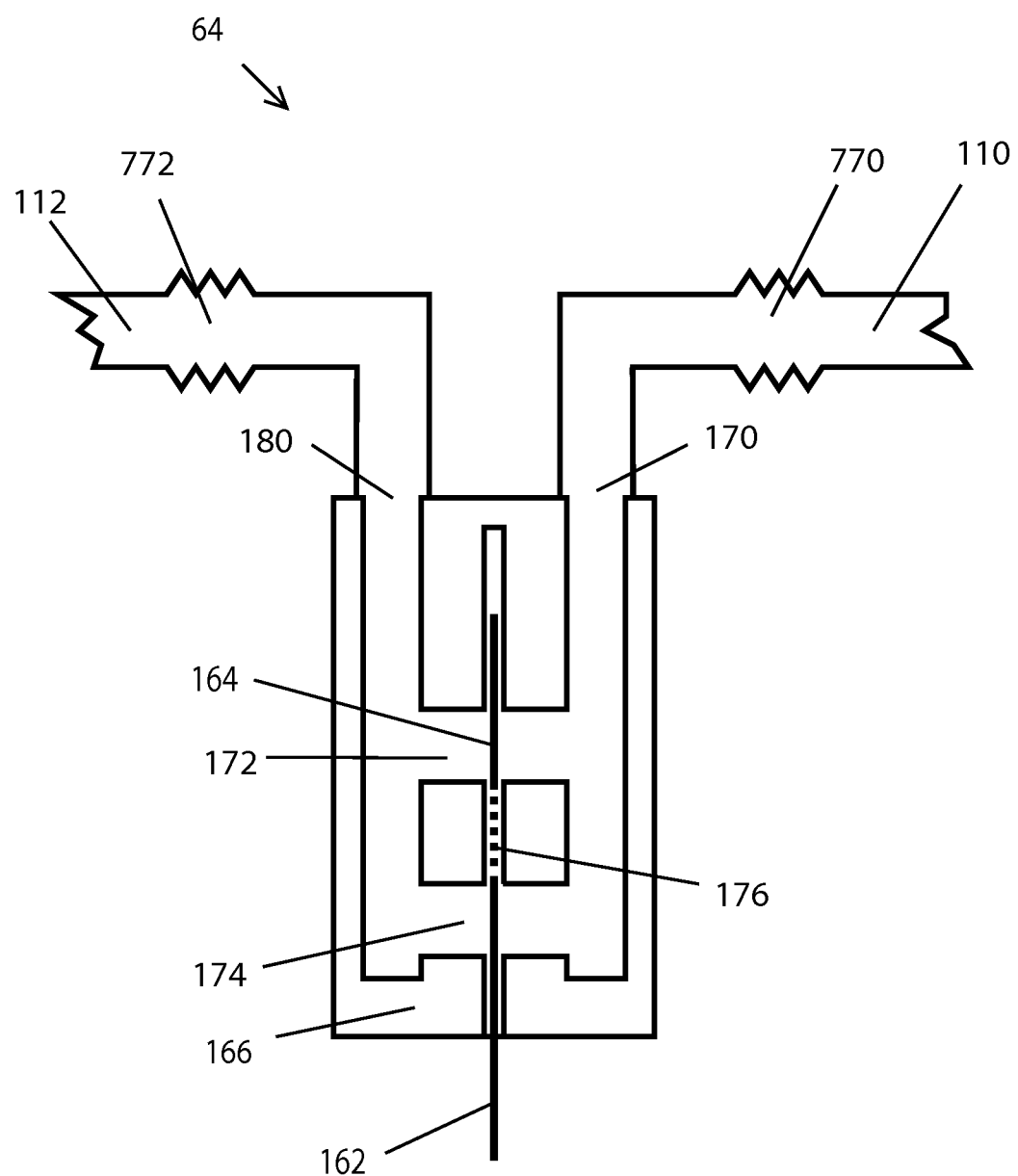
FIG. 17 depicts a front view of the valve portion of flow regulator unit from FIG. 10 further including pressure wave and flow wave integrating components up-stream the valve portion port for pressure ripple and flow ripple control.
Figure 21A:
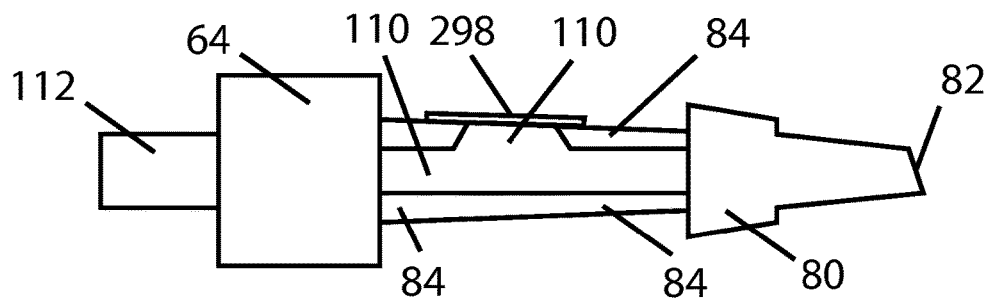
FIGS. 21A, 21B and 21C are schematic illustrations of the implementation of a fluidic integrator including a fluidic capacitor to improve operation of the flow regulator unit of the present invention.
Figure 21B:
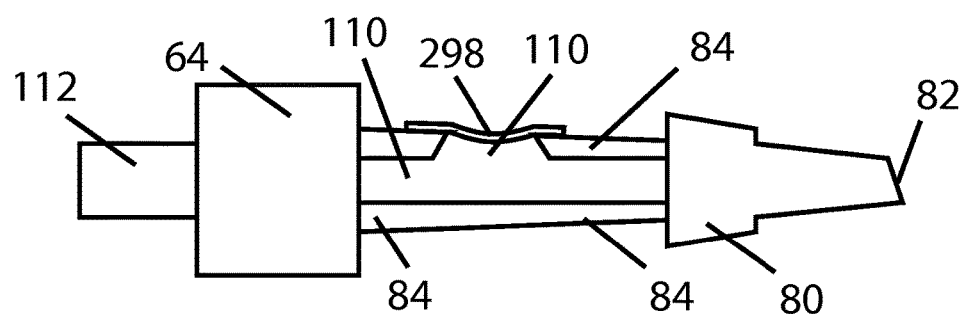
Figure 21C:
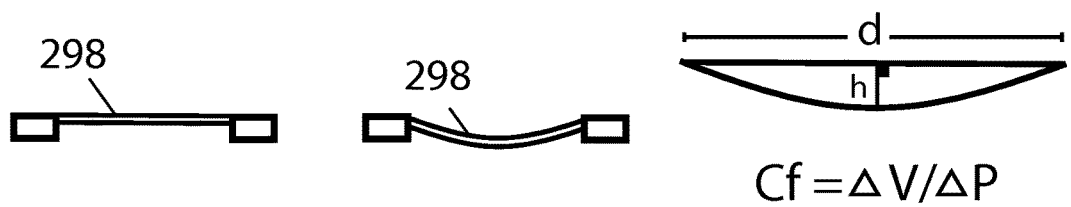
Figure 23:
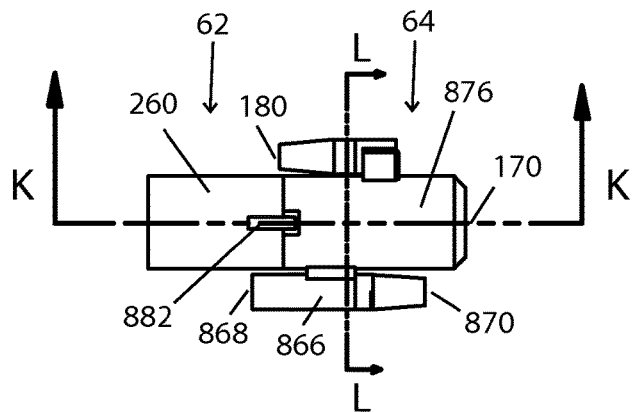
FIGS. 23 to 27 provide sectional and extended views of the actuator and valve portions of an embodiment of the flow regulator system.
Figure 24:
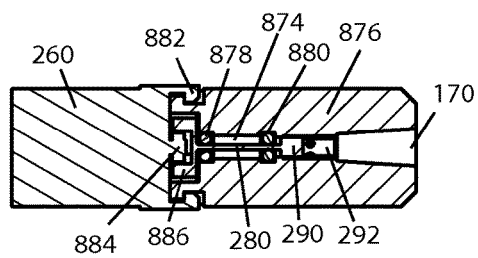
Figure 25:
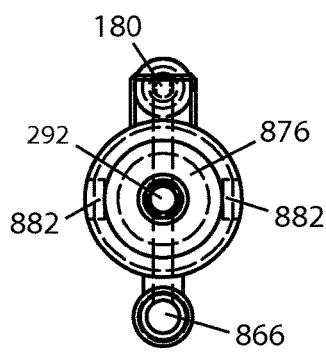
Figure 26:
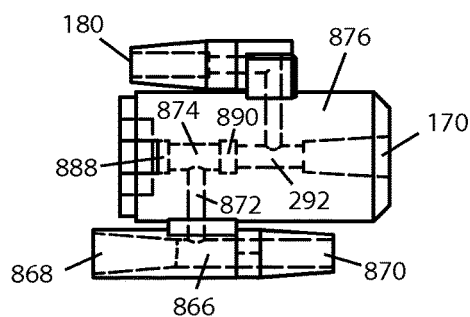
Figure 27:
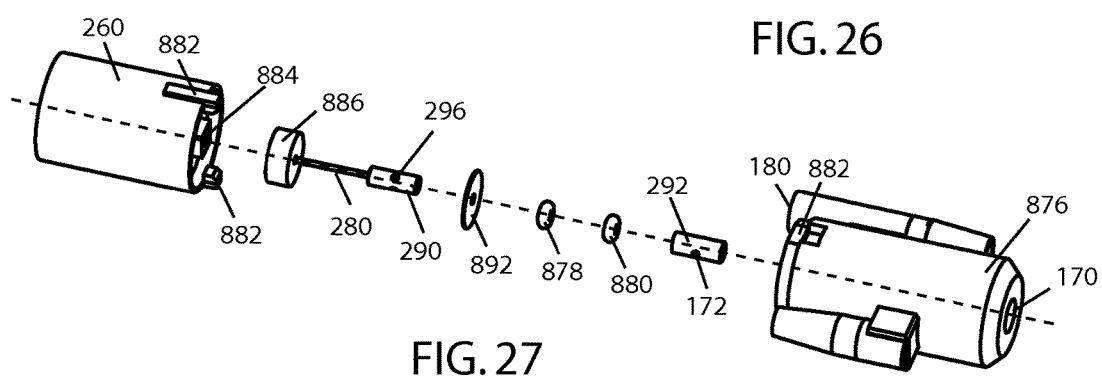

Shown in FIG. 17 is a valve portion 64 of the present invention with window 176 in blade 164 framed in the center or flow blocking region either during standby mode or while window 176 is traversing the center region during blade 164 oscillation. In this figure is illustrated a fluid capacitive component 770 incorporated to conform a flow and pressure wave-integrator and low pass filter in first fluid path 110 together with fluid path fluidic resistance to reduce ripple and acoustic shockwaves at aspiration port 82 that could affect the body cavity being aspirated. A second flow/pressure wave integrator device 772 can also be incorporated in the second fluid path 112. These integrator devices can be incorporated to attenuate flow and pressure waves as well as acoustic shockwaves that can be generated by the cyclic valve opening and closure. These waves can produce disturbing vibrations of handpiece 70 and/or of aspiration tubing and attached devices. Also, fluidic shockwaves produced by valve 64 and transmitted though first fluid path 110 to port 82 may have a negative impact when transmitted to the interior of delicate organs such as the eye where these waves can promote risks of detachments, hemorrhages or damage to endothelial cells and nerve fibers. In its simplest form, integrators 770 and 772 can be composed of inserted segments of elastic tubing of selected dimensions to matching valve speed of operation and aperture dimensions to maximize efficacy. More complex integrators with improved response curves such as elastic membranes, bladders or bellows could also be used for this purpose. As a mode of example of an integrator device 770 in FIGS. 21A, 21B and 21C is shown an implementation of a fluid capacitor installed in first fluid path 110. Handpiece 70 is traversed by first fluid path 110 including aspiration tube 84 between aspiration port 82 and valve portion 64. A circular opening 299 having a diameter "d" connects the inner fluid conduct with the surface in handpiece 70. An elastomer membrane 298 is arranged to cover opening 299 in vacuum-tight conditions the membrane kept in position for example by means of suitable adhesives or tensile force. Membrane 298 is selected with particular characteristics such as material, elasticity, hysteresis, thickness, profile and tension. As a mode of example a condition can exist where circular opening 299 has a diameter "d" of 3 mm where a vacuum inside first fluid path of 600 mmHg produces an inward spherical deformation or "bulging" of membrane 298 that has a height "h" of 1.0 mm. This condition is illustrated in FIG. 20B. Calculating the volume of a spherical cap Vc=(Pi*h*h*(3*r−h))/3 allows to determine that in this particular configuration a pressure difference across membrane of 600 mmHg produces a volume fluctuation of 4 µL in the region of opening 299. Fluid capacitance can be calculated for this exemplary fluid capacitor Cf=4 µL/600 mmHg=0.0674/mmHg. The fluid capacitor here described operating in combination with the fluidic resistance of first fluid path conforms integrator 770 acting as a fluidic low pass filter and integrator, capable of attenuating high frequency pressure and flow fluctuations derived from the repetitive opening and closure of valve 64 during operation of flow regulator 60. The values chosen for the present example of a fluidic capacitor are for illustration purposes and the components configuring device 770 should be calculated or empirically constructed according to the characteristics of any particular configuration for a flow regulator system 60. Cut-off frequency of the low pass filter is generally related to the formula f=1/(2*PI*R*C) and can be represented in a corresponding Bode plot. This cutoff frequency can be selected taking in consideration operating frequency of the cyclic valve mechanism of flow regulator system 60. Values between 0.01 µL/mmHg and 1.0 µL/mmHg can be selected for wave-integrator/fluid capacitor elements for ripple compensation below 10% for most embodiments of the flow regulator system of the present invention. Similarly to the described integrator device 770 located in first fluid path 110, a second integrator device 772 could be located downstream in second fluid path 112 to improve flow regulator system 60 performance. Although it is preferable for the practice of this invention that watertight and vacuum tight conditions are met during flow regulator system 60 operation, the presence of some degrees of static leakage and dynamic leakage as well as some degree of non-vacuum-tight conditions can be tolerable and do not depart from the scope of the present invention. In applications where incorporation of a fluidic capacitor 770 in fluid path 110 could result impracticable, or as a complement to capacitor 770, a bubble generator 773 is shown in FIG. 30A that can be incorporated to produce or deliver gas bubbles 780 into the fluidic volume corresponding to fluid path 110 for ripple attenuation. Bubbles produced by bubble generator 773 in fluid path 110 act as transient fluid capacitors storing energy during expansion and releasing energy during contraction. The total volume of gas produced by generator 773 mixed with the circulating liquid at any given time provides an alternative or complementary system to introduce a fluidic capacitive component into fluid path 110 to conform a flow wave and pressure wave R-C low pass filter/integrator to minimize ripple at port 82. The size distribution of the bubbles can impact R-C filter performance due to the variation in surface tension with bubble diameter hence the capacitive properties. Gas generator 773 can be implemented by disposing at least two non-reacting electrodes 774a and 774b in electrical contact with the fluid inside fluid path 110 and circulating an electric current between them across the electrolytic solution. Electrodes 774a and 774b are isolated from surrounding conducting parts by an isolator plate 775 and receive electric current through conductor cables 784a and 784b from a bubble generator driver 776. A low DC voltage, adjustable up to 80 volts will produce an electric current that produces gas bubbles mainly by electrolysis. Alternatively, a high AC voltage will produce bubbles by heating of the electrolyte solution near the electrodes up to the boiling temperature for an existing pressure. Typical AC voltage frequencies are in the range of 250 KHz to 16 MHz and can be delivered in bursts at an adjustable voltage up to 500 volts. This mode of bubble generation operates under the principle of bipolar diathermy. Controller 132 can regulate the production of gas in fluid path 110 by commanding bubble generator driver 776 to produce bubbles of characteristics suitable to obtain a desired integrating/filtering effect without compromising performance. In this way flow ripple and pressure ripple as well as acoustic waves in aspiration port 82, all produced as a consequence of valve 64 operation, are minimized. Controller 132 can modulate bubble generation to effectively counteract aspiration port 82 ripple by using system parameters such as aspiration line vacuum, rotary speed and rotor position using pressure sensor 118 and driveshaft position sensors 264 and 274. Controller 132 and electrode arrangement can command to deliver bubbles at a determined location, amount, size and timing within fluid path 110 volume according to preset operation conditions using a formula or a table stored in ROM. Particles contained in the fluid can be segmented by the cycling mechanism without impact in operation as shown in the sequence depicting snapshots during a single cycle of aperture 200 opening and closure from FIG. 16A to 16E. Rotating rim 294 has an edge 295 that can be sharp to expedite tissue fragmentation. A tissue fragment 204 going with the flow across aperture 200 can be engaged by edge 205 in a way that fragment 204 is segmented. A portion 208 of tissue fragment 204 can be retained inside chamber 292 while another portion 206 of tissue fragment 204 can pass through aperture 200 into fluid passage 172. Repeated cycles of opening and closure of aperture 200 inside valve portion 64 at fast pace allow the clearance of all tissue fragments suspended in the fluid without compromise of the operation of the cyclic aperture flow regulator 60 of the present invention.

In operation the present invention is used with advantage to remove fluid and tissue fragments from a body cavity such as cataract fragments from within the anterior chamber of an eye. Surgical probe 80 is inserted inside the anterior chamber of the eye where the crystalline lens is to be removed. An operator first commands processor 132 from console 150 through user interface 154 and foot pedal 152 to open irrigation valve 90 to allow irrigation of fluid into the eye through irrigation probe 104. With irrigation enabled the operator can command to aspirate fluid and particles from inside the eye through distal opening 82 from surgical probe 80.

For operation of the flow regulator system of the present invention, the cyclic aperture modulation feature of flow regulator system 60 is enabled by powering rotary motor 260 to produce continuous rotation of rotor 290 inside valve 520 at a speed preferably above 12.000 RPM. Rotary speeds above 15.000 RPM produce a pressure ripple of amplitude below 10% being considered to produce a substantially steady flow. Rotation of rotor 290 produces at least one substantial reduction of the cross-sectional area of fluid passage 200 per rotor revolution, as determined by the axial position of rotor 290 inside chamber 292. In embodiments incorporating a bubble generator 773 as described in FIGS. 28A and 28B, the rotary speed required to produce levels of pressure ripple below 10% is reduced when the bubble generator system is activated during operation. In this way, rotary speeds of 8.000 RPM can produce pressure ripple levels below 10% when the bubble generator 773 is operated simultaneously with aspiration. These values are provided as reference only as different dimensions of fluid path 110 as well as valve 64 distance from port 82 have impact on minimum rotary speed to achieve a ripple level below 10% producing a substantially steady flow.

Ripple reduction is of interest only when aspiration port 82 is in the un-occluded condition. When aspiration port 82 becomes significantly occluded ripple disappears as in this situation vacuum inside path 110 becomes equal to vacuum inside path 112 regardless of the cyclical open or closed condition of valve 64. This occurs because environmental pressure cannot reach path 110 interior in the occluded condition with the consequence that ripple becomes extinguished.

With rotor 290 continuously rotating inside valve chamber 292 flow can be adjusted by commanding linear actuator 270 to axially displace the rotating rotor 290 inside valve chamber 292 into a position that will produce a desired flow rate according to a calibration protocol. There is an operating range regarding the axial position of rotor 290 inside chamber 292 where opening and also substantial closure of aperture 200 both exist within a single revolution of rotor 290. Excessive advancement of rotor 290 inside chamber 292 will produce permanent occlusion of aperture 200 regardless of the rotary position of rotor 290 by permanent overlay of the fluid passage 172 entrance with the body of rotating rotor 290, the valve remaining permanently in a substantially closed condition. Too little displacement of rotor 290 inside chamber 292 will determine too little exposure of lid 294 over fluid passage 172 entrance without significant reduction of aperture 200 dimensions during any portion of one revolution of rotor 290. In this condition transient substantial occlusions of aperture 200 will not occur during each cycle of revolution of rotor 290 the valve remaining in a permanently open position and losing the enhanced flow regulating attributes. As a mode of reference only, an aperture 200 of maximum size 0.3 mm$^2$ and minimum size 0.003 mm$^2$ operated at 680 mmHg vacuum produces a substantially steady unobstructed flow of 30 cc/min and effectively cancels post-occlusion surge with minimum ripple (below 10%) when operated at a rotary speed of 12.000 RPM. Increasing aperture 200 maximum dimensions to 0.45 mm$^2$ and minimum size 0.003 mm$^2$ operated at 680 mmHg vacuum produces a substantially steady unobstructed flow of 60 cc/min. A sub-ambient pressure or vacuum must be provided into second fluid path 112 by activation of vacuum source 114 and by the opening of vacuum control valve 118 while venting valve 120 remains in closed position.

It is relevant to describe two important relationships to better understand cyclic aperture flow regulator system operation:

a) Un-obstructed flow circulating into first fluid path 110 through probe port 82 and across valve 520 into second fluid path 112 for a given rotor 290 axial position is a function of the vacuum level inside second fluid path 112.

b) Un-obstructed flow circulating into first fluid path 110 through probe port 82 and across valve 520 into second fluid path 112 is a function of the axial position of rotor 290 inside chamber 292. For given form factors for rotor 290 and for valve chamber 292 including fluid passage entrance 172, different axial positions of rotor 290 determine different root mean square (RMS) computations of the cyclically varying dimensions (cross-sectional area) of aperture 200 along each revolution of rotor 290. Flow across valve 520 for a given vacuum level at second fluid path 110 is a function of the RMS aperture value.

In this way unobstructed flow rate across the cyclic aperture flow regulator system of the present invention can be adjusted in two main ways: 1) by determining the vacuum level inside second fluid path 112 and 2) by determining the axial position of rotor 290. A plurality of combinations of vacuum levels inside second fluid path 112 and rotor 290 axial positions can produce similar flow rates into unobstructed port 82. However the operator will notice differences in performance of surgical probe 510 when using low vacuum and high vacuum to obtain a similar aspiration flow rates. When using high vacuum tissue fragments will be aspirated forcefully even at low flow rate. When using low vacuum there will be less chance to damage surrounding tissues during complicated surgical maneuvers.

Flow rate can be adjusted by an operator by providing an input signal for example using foot pedal 152 to processor 132. Progressive foot pedal depression can instruct processor 132 to command linear actuator 270 to vary the axial position of rotor 290 to increase or decrease flow rate. Vacuum provided by vacuum source 114 into second fluid path 112 can also be varied by providing a command to processor 132. Both parameters, axial position of rotor 290 and vacuum level inside second fluid path 112 can be adjusted simultaneously to obtain a determined performance profile. The possibility of selecting a determined flow rate using different vacuum levels as enabled by the cyclic flow regulator system of the present invention is novel and valuable.

With irrigation enabled and aspiration enabled the operator can grasp tissue fragments and remove them from the eye by aspiration only eventually using the force of vacuum as the only lens disrupting energy. Alternatively, when cataract fragments are too hard for simple aspiration, a complementary source of lens disrupting energy such as ultrasound can be applied. Hub 86 couples surgical probe 80 with tissue disruption actuator 68 composed by an axial ultrasonic actuator 512 and an ultrasonic motion converter 514. In combination actuator 512 and converter 514 can transmit ultrasonic motion to surgical probe 80 providing an effective method to emulsify lens material. Depending on the driving frequency provided by tissue disruption driver 134 to actuator 68 the pattern of mechanical oscillation of probe 80 can be programmed to be parallel to the shaft axis (longitudinal) or alternatively, rotatory along the shaft axis (torsional). A noticeable feature of the cyclic aperture flow regulator system of the present invention is that motion of rotor 290 inside chamber 292 has rotary and axial component that are in coincidence with the eventual axis of displacement that can be transmitted to surgical probe 80 by tissue disruption actuator 68. This feature is of primordial importance because it allows simultaneous operation of the cyclic flow regulator system 60 and of tissue disruption actuator 68.

It is desirable to operate linear actuator 270 using a position feedback signal from linear displacement sensor 274. In this configuration actuator controller 132 receives driveshaft 280 axial position information and commands operation of linear actuator to locate rotor 290 at a desired axial set point to produce a desired unobstructed flow rate according to data from a calibration procedure stored in memory. The position feedback signal provided by sensor 274 allows to incorporate a control loop into actuator controller 132 using for example a proportional-integral-derivative filter (PID) to accurately and rapidly adjust the axial position of rotor 290 relative to valve chamber 292 according to the desired unobstructed flow rate set point commanded by an operator.

In a basic mode of operation of the cyclic flow regulator of the present invention flow rate for a given vacuum level is set by determining the axial position of rotor 290, while providing steady rotation to rotor 290 to produce cyclic fluctuation of aperture 200 cross-sectional area including at least one portion of substantial reduction of the cross-sectional area of aperture 200 during each cycle.

In some situations it can be of advantage to have control of the rotary position of rotor 290 for example when a determined axial alignment is desired between rotary lid 294 and fluid passage channels 172 and 174. This action can be of interest for example during a reflux operation or to ensure a permanently open aperture 200 if some malfunction is detected by controller 132 or processor 132. Rotary sensor 264 can provide a precise angular position signal to controller 132. Controller 132 can command rotary motor 260 to actively stop rotary shaft 262 at a selected angular position when using for example a brush-less DC motor that allows this operation.

Figure 29:
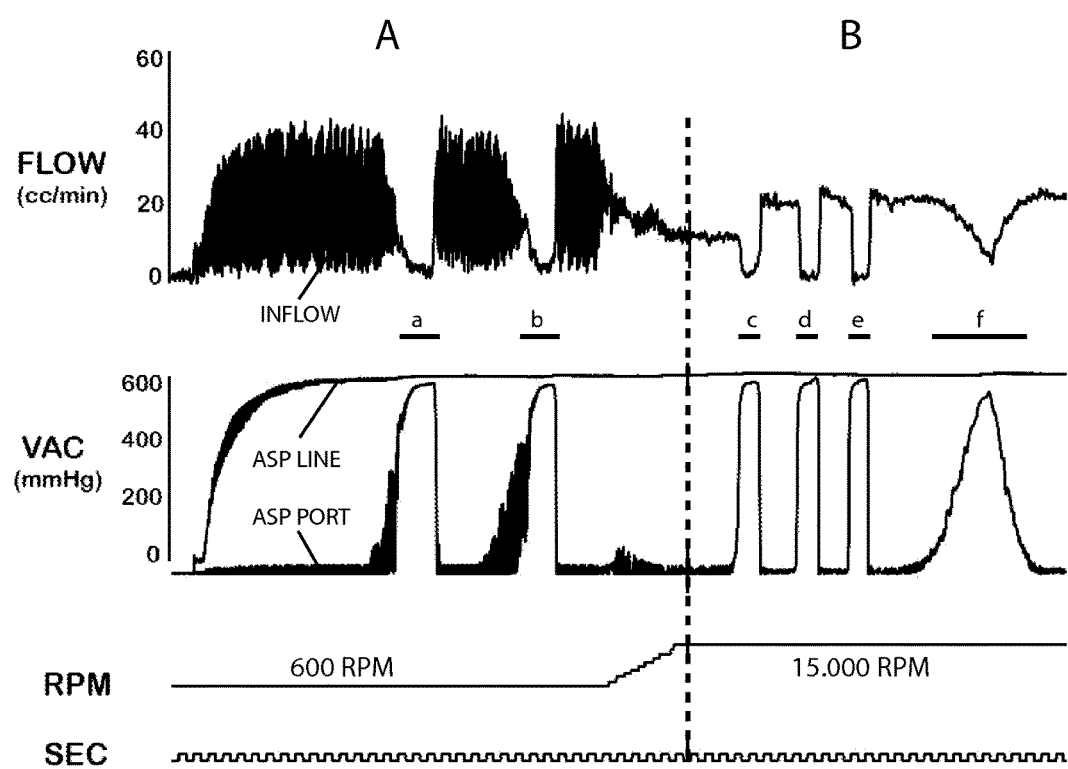
FIG. 29 is a graph illustrating cancellation of flow and pressure fluctuations by operation of a valve of the present invention at a high speed. Aspiration port pressure response to occlusions is also illustrated.
Figure 30:
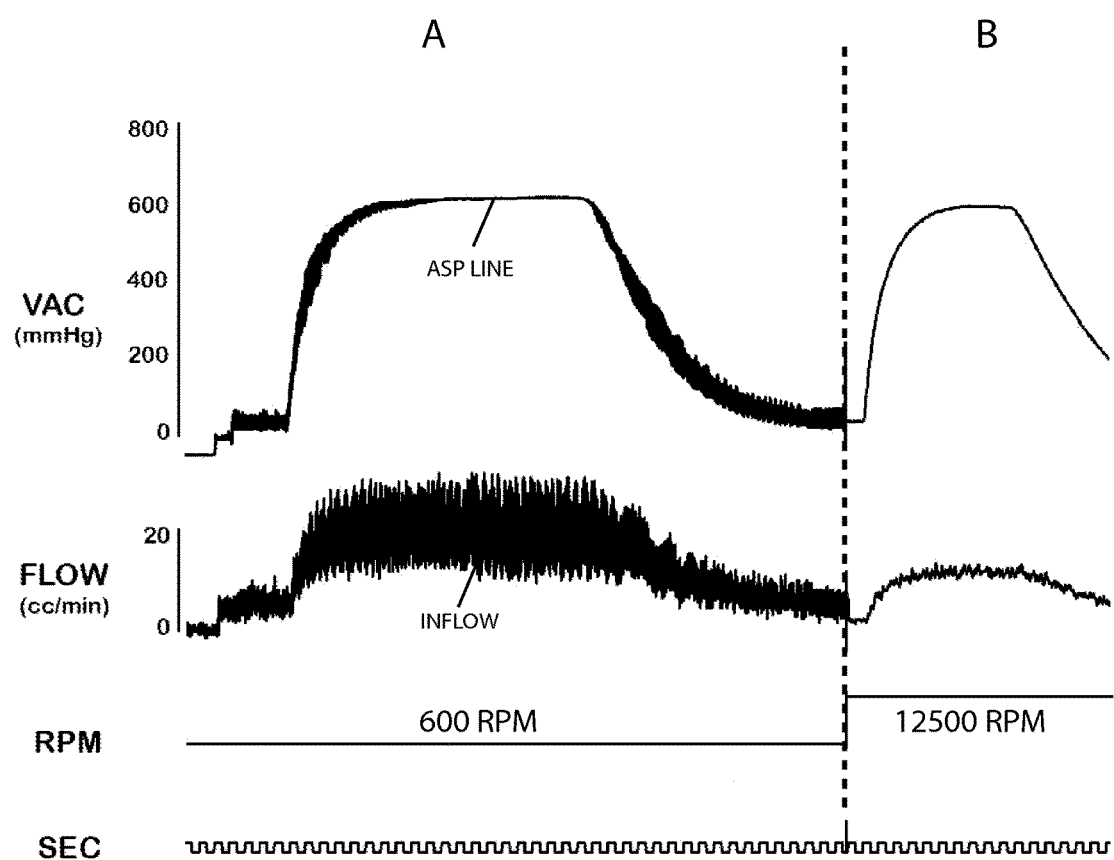
FIG. 30 is a graph illustrating cancellation of flow and pressure fluctuations by operation of a valve of the present invention at a high speed.
Figure 31:
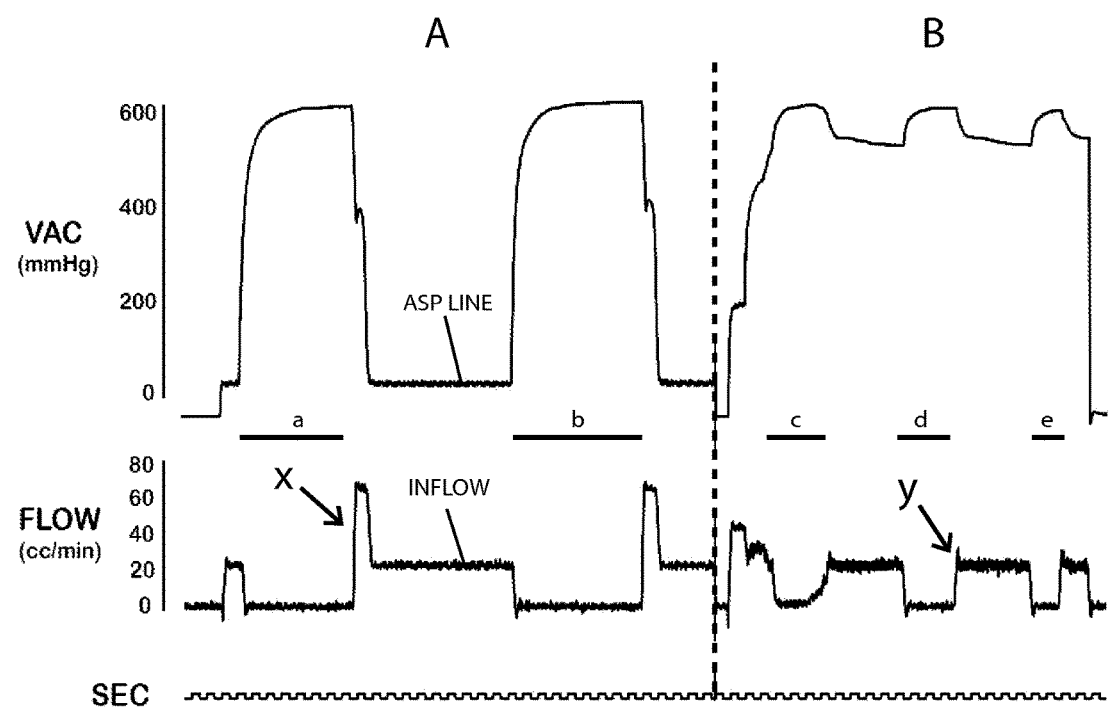
FIG. 31 is a comparative graph illustrating suppression of post-occlusion surge measured in the flow domain.

Charts in FIGS. 29 to 31 are provided with recordings to better explain rationale of operation as well as performance of flow regulator system. FIG. 29 is a chart illustration with upper tracing corresponding to fluid flowing into aspiration port 82. Lower tracings correspond to vacuum recordings at aspiration line (path 112) and at aspiration port 82. Horizontal bars under letters "a" to "e" signal periods of full occlusion of port 82. Horizontal bar under letter "1" illustrates a slowly incrementing and decrementing occlusion. The left side marked "A" corresponds to recordings with valve rotor 290 rotating at a speed of 600 RPM and the right side marked "B" at a speed of 15.000 RPM. It can be clearly appreciated that ripple is substantially reduced when the rotary speed is set at the higher level. It can also be appreciated during occlusions "c", "d" and "e" that vacuum rise at the aspiration port in response to full occlusions is very fast.

FIG. 30 is a chart illustration with upper tracing corresponding to vacuum recordings at aspiration line (path 112). Lower tracings correspond to fluid flow into aspiration port 82. Left side "A" corresponds to vacuum rise and decay with valve 64 operating rotor 290 at 600 RPM and right side "B" with rotor 290 at 12.500 RPM. It can be seen that flow pulsations (ripple) are substantially reduced at the higher rotary speed "B".

FIG. 31 is a chart illustration with upper tracing corresponding to vacuum recordings at aspiration line (second fluid path 112). Lower tracing corresponds to fluid flow entering into aspiration port 82. Horizontal bars under letters "a" to "e" indicate periods of full occlusion of aspiration port 82 with high vacuum levels. At the left side "A" are displayed recordings from a state of the art phacoemulsification console Infiniti®, Alcon, USA. At the right side "B" are displayed recordings from a rotary embodiment of the flow regulator system of the present invention operating at a speed of 10.000 RPM. Arrow "x" signals an illustrative post-occlusion surge event characterized by a transient increase in flow occurring immediately after cessation of a period of occlusion in the Infiniti® console. Arrow "y" signals a corresponding inflow recording segment occurring immediately after cessation of occlusion when using the flow regulator system of the present invention. It can be appreciated that there is no perceptible transient increase in flow.

A calibration routine can be performed at the beginning of each procedure during system priming. An example for a calibration routine can consist in: a) installation of a test chamber of the prior art to fluidly connect irrigation probe 104 with aspiration port 82, b) detection of a static irrigation pressure in the pressurized fluid source 100 using pressure sensor 106 with valve 90 closed, c) opening of valve 90 to allow flow from the pressurized fluid source 100 into fluid paths 110 and 112. d) provision of a determined vacuum level by activation of vacuum source 114, e) activation of rotary motor 260 to steadily rotate rotor 290 at the desired RPM, f) performing a data acquisition sequence along a series of step adjustments of the axial position of rotor 290 followed by storing in memory of the axial position of rotor 290, of the irrigation pressure reading from sensor 106 and of the vacuum reading from sensor 140 for each step, g) Calculation of the unobstructed flow rate for the measured steps of axial position of rotor 290 incorporating for this purpose irrigation line 102 resistance and the pressure drop measured between static pressure and steady state pressure, h) building of a transfer function to be used by controller 132 to adjust flow rate to a set point commanded by an operator by adjusting the axial position of rotating rotor 290 and the vacuum level from vacuum source 114. The calibration routine can also incorporate stepped measurements at different rotary motor speeds. Reducing rotary speed of rotor 290 can result advantageous in some situation where for example, more ripple in port 82 could help to disrupt lens fragments. The calibration routine of flow regulator system 60 can also include determinations of flow rate with tissue disruption actuator 68 active at different power settings to adjust for flow drifts that can occur when both systems are operated simultaneously during surgery.

Reflux Operation: An operator can request a reflux operation by depressing a foot pedal switch when for example an unwanted portion of tissue is captured by distal opening 82 from probe 80. Reflux can be provided by providing a transient increase in pressure inside second fluid path 112 by transitorily closing valve 118 and opening valve 120 with valve 64 rotary motor 260 kept operating. The flow rate of the reflux operation (reflux speed) can be adjusted by simultaneously positioning rotor 290 in a desired axial position during the reflux. An alternative method for a reflux operation can consider stopping rotor 290 in such way that aperture 200 is kept continuously open during the duration of the reflux.

Operation of the cyclic aperture flow regulator system of the present invention provides several advantages over the prior art systems. Among the most relevant is that post-occlusion surge is virtually eliminated reducing the risk for complications. Maximally high vacuum levels can be used without post-occlusion surges increasing the efficiency to aspirate lens tissue fragments and reducing the need for complementary lens disrupting energies such as ultrasonic emulsification.

Another relevant advantage is the fact that this system operates in a way that unobstructed flow rate can be adjusted independently of the aspiration line vacuum level. This allows to set a low flow rate with a high vacuum for a slow but efficient removal of the crystalline lens material improving patient recovery time and operating room patient turnover.

Figure 15:
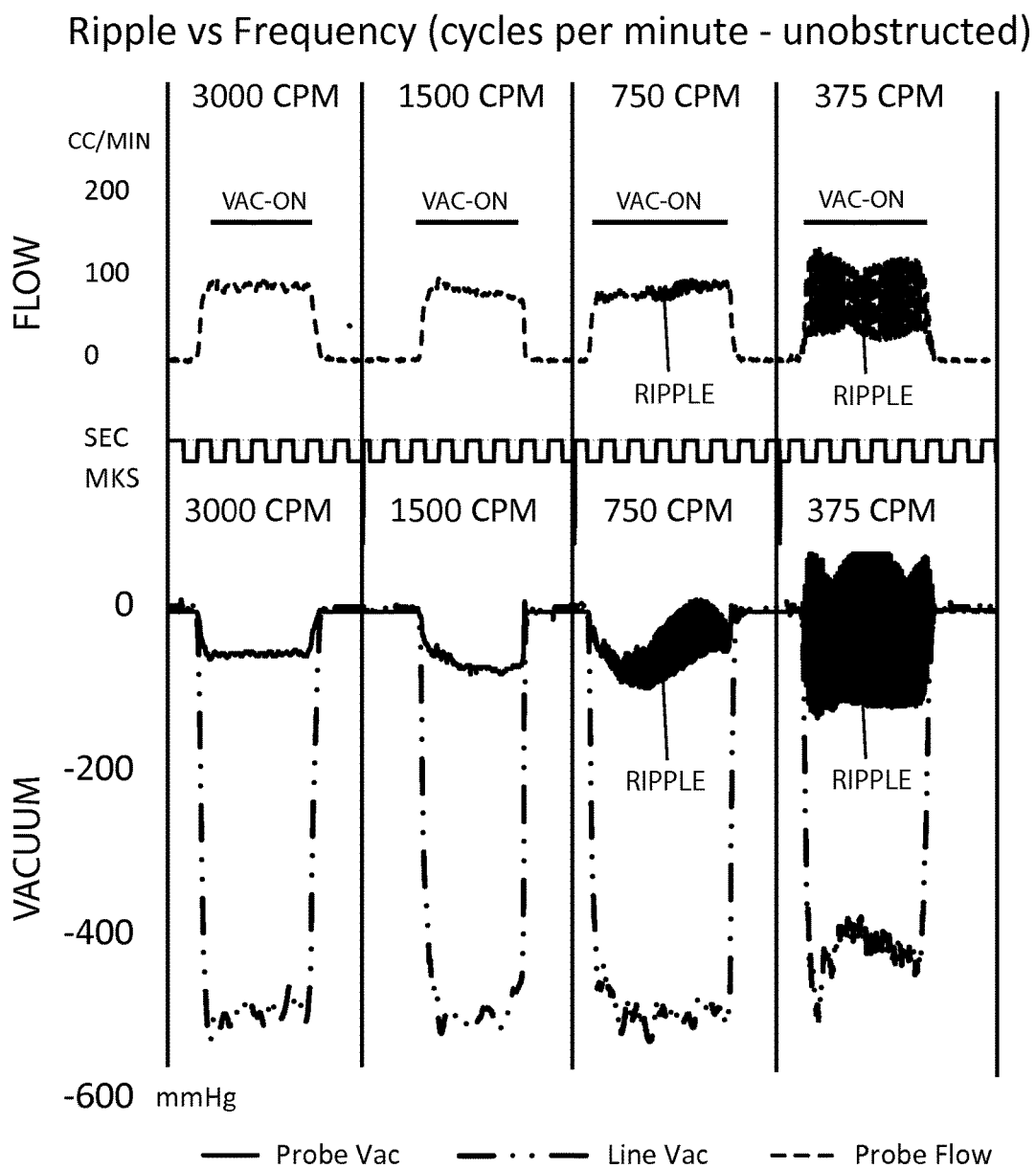
FIG. 15 is a graph depicting flow and pressure measurements at the aspiration opening of a surgical probe with a cyclic aperture flow regulator system of the present invention operating at different frequencies and illustrating that flow and pressure ripple diminishes above 750 CPM and transforms into a substantially steady flow at operation frequencies above 1500 cycles per minute.
Figure 16:
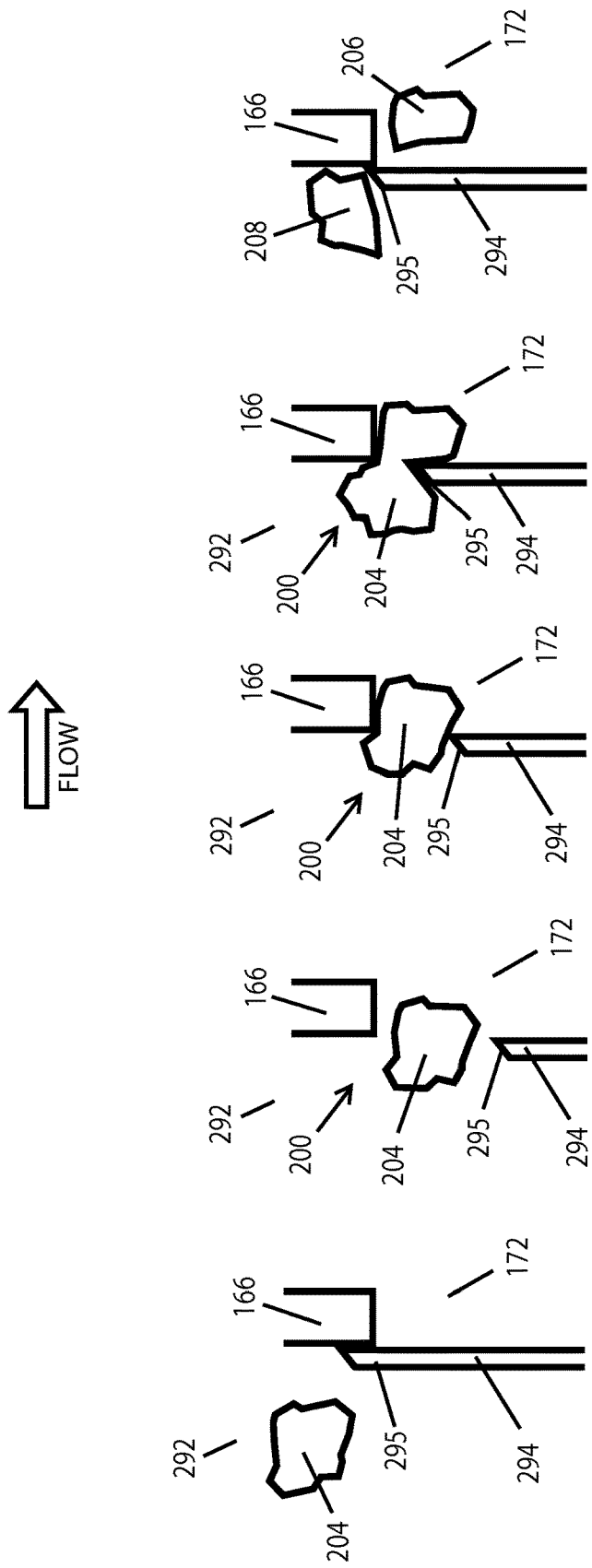
FIGS. 16A to 16E corresponds to a sequence of snapshots illustrating how tissue fragments traverse the fluid aperture without clogging.

Different combinations of aspiration line vacuum settings and unobstructed flow rate settings can be programmed and adjusted using the user interface 154 panels or foot pedal 152. These adjustments can be set fixed at the user interface or can vary continuously responding for example to levels of foot pedal depression. As can be seen in the graph in FIG. 15, the pressure and flow ripple effects detected at aspiration port 82 produced by the cyclic aperture flow regulator system of the present invention is progressively reduced by increasing the frequency of the cycles of aperture cross-sectional area fluctuation to an extent where in becomes insignificant (above 2000 cycles per minute in this example).

Valve 520 can be located in a more proximal position of tube 522 as long as the volume of first fluid path 110 is kept low by design. Also a more proximal location of valve can be considered in application with less demanding specifications or when planning to use relatively low vacuum levels. An illustration of a more proximal location of valve 520 is provided in FIG. 8L.

Safety Considerations: During operation the cyclic aperture flow regulator system 60 of the present invention produces intermittent substantial reductions of the dimensions of a fluid aperture 200 at high frequency. This mode of operation produces a substantially steady flow through surgical probe 80 into an aspiration line that can be adjustable between about no flow and a maximum flow. Safety measures must be implemented when operating flow regulator system 60 in combination with a tissue disruptor actuator that can generate heat such as with ultrasonic phacoemulsification. Low flow is a known risk factor for corneal burns (also known as incisional thermal injuries) produced by surgical probes during ultrasonic phacoemulsification. It is desirable that controller 132 from regulator 60 communicates with processor 132 from console 150 to avoid operational conditions that can be considered of risk of promoting a surgical complication such as a corneal burn. For example a minimum steady flow rate can be determined by regulator 60 aperture settings and by vacuum source 114 settings before activation of tissue disruptor actuator 68 if this operation involves potentially harmful heat generation. Also, a malfunction could occur that produced an unexpected continuous significant restriction to flow inside valve 64. This condition could occur for example if one actuator ceased to operate leaving rotor 290 permanently in a fluid passage blocking position. Controller 132 can detect such condition from the signals from sensors 264 and 274 and transmit a failure alarm signal to processor 132 or to an operator to take measures to take preventive measures to avoid a complication such as cutting ultrasound energy off. Failsafe actuators can also contribute to reduce the risk of permanent fluid passage blockage. For example, motor 260 can incorporate a centrifugal mechanism that produces axial retraction of shaft 262 when the rotary speed of the motor is below a safety limit. In this condition retraction of shaft 262 displaces rotor 290 through driveshaft 280 into a "safe mode" position inside chamber 292 in which no part of rotor 290 can block the entrance of fluid passages 174 or 174 the flow regulator valve remaining in an open status.

In this way the cyclic aperture flow regulator system described is operative to prevent post-occlusion instability of a body cavity during surgical aspiration of fluid and tissue fragments through an aspiration opening of a surgical probe. The fluid and tissue fragments can be aspirated from said body cavity using said surgical probe along a fluid path without the occurrence of instability of said body cavity caused by fluid surges into said fluid path caused by occlusion breaks of said aspiration opening of said surgical probe.

The method described prevents instability of a body cavity during surgical aspiration by disposing an adjustable fluid aperture in the aspiration fluid path connecting a surgical probe with a vacuum source. Actuator means are then provided that are operable to vary the cross-sectional area of said adjustable fluid aperture. Control means are also provided to command said actuator means to vary in cycles the cross-sectional area of said adjustable fluid aperture including at least one segment within each of said cycles where said cross-sectional area is substantially reduced or closed. These cycles are commanded to occur at a frequency sufficiently high to produce a flow through said surgical probe that is substantially steady. In this way fluid and tissue fragments can be aspirated from said body cavity through said surgical probe without instability caused by fluid surges into said surgical probe caused by occlusion breaks.

Handpiece with Axially Adjustable Rotor and "In-Probe" Valve Portion: Surgical Probe Includes Part of Valve Portion 64.

Figure 5A:
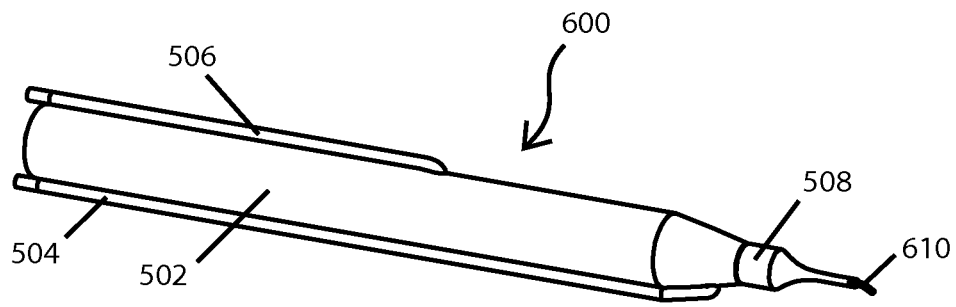
FIGS. 5A to 5C details the internal arrangement of parts in a surgical handpiece incorporating an additional rotary embodiment of the flow regulator system with the valve portion disposed inside a surgical probe.
Figure 5B:
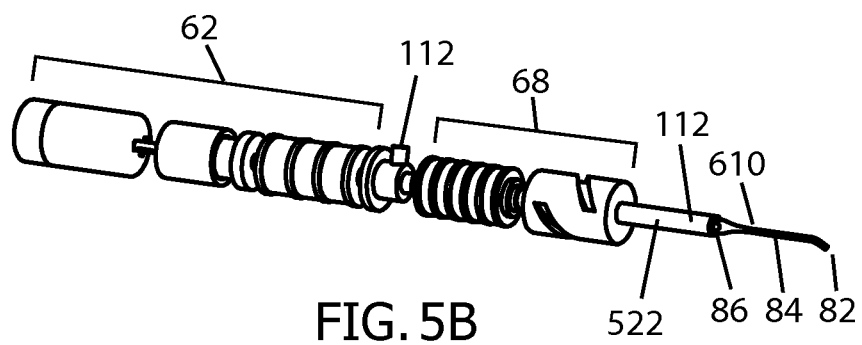
Figure 5C:
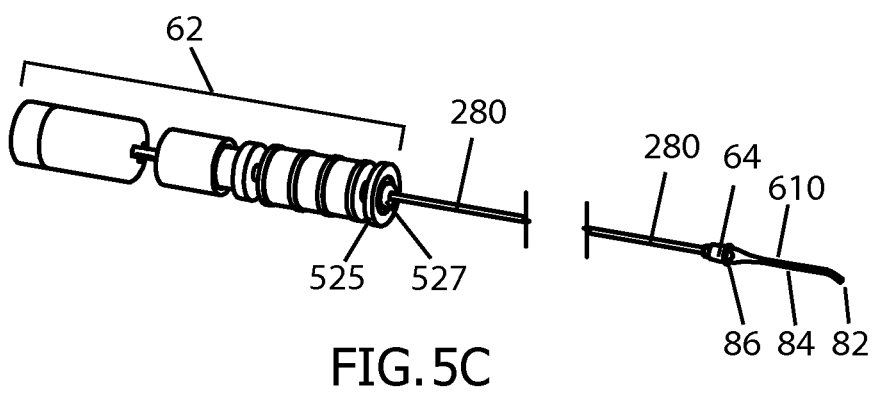
Figure 5D:
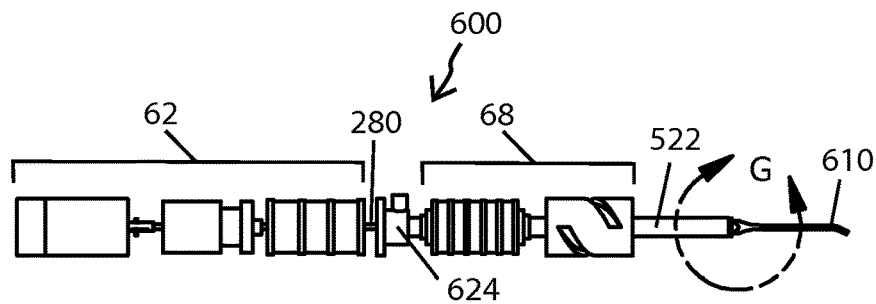
FIGS. 5D to 5G shows detail sectional views of the valve portion from FIG. 5A.
Figure 5E:
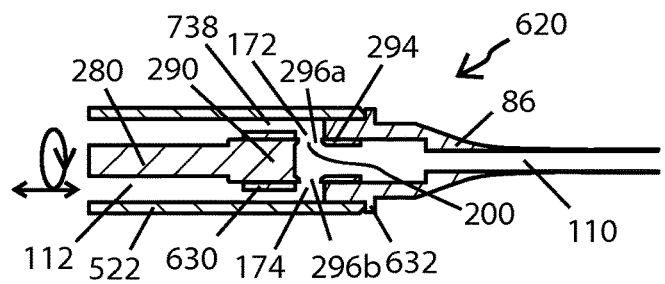
Figure 5F:
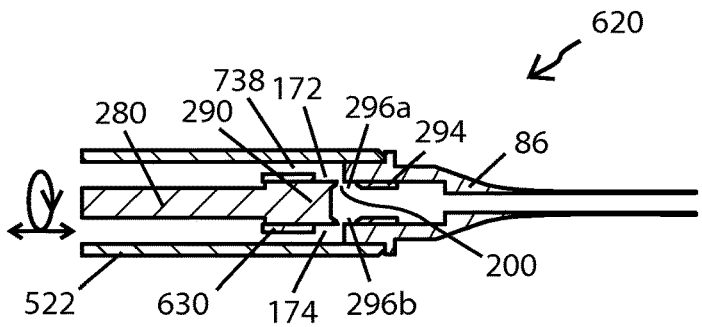
Figure 5G:
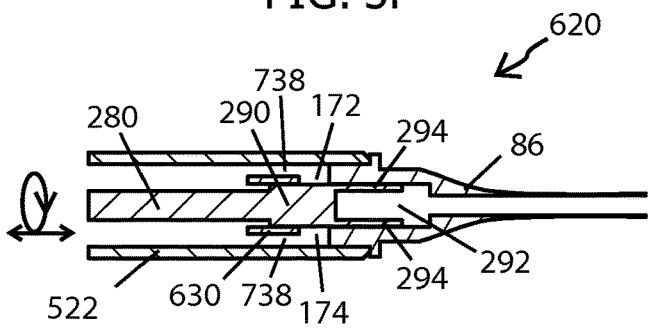
Figure 6A:
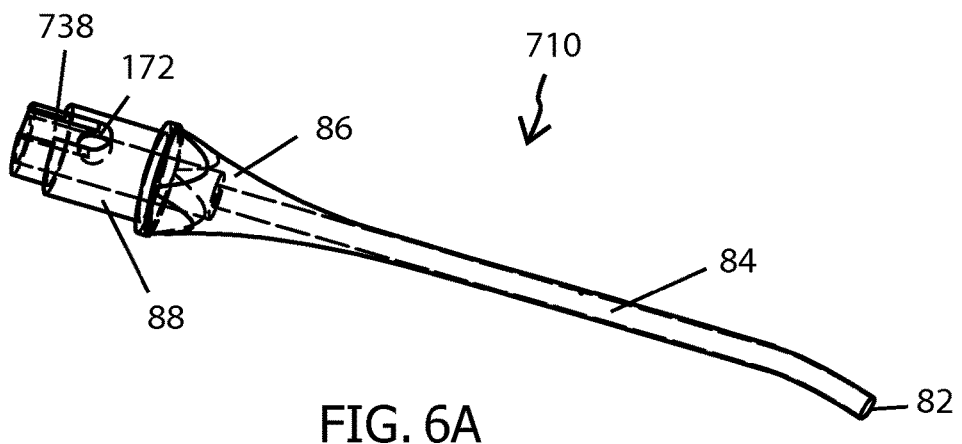
FIGS. 6A to 6C depict perspective and sectional views of a surgical probe that provides in part the composing elements of the valve portion of the flow regulator system of the present invention.
Figure 6B:
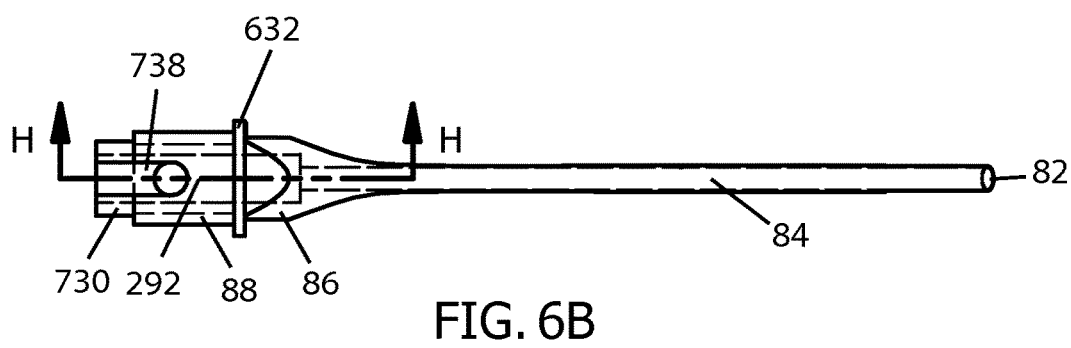
Figure 6C:
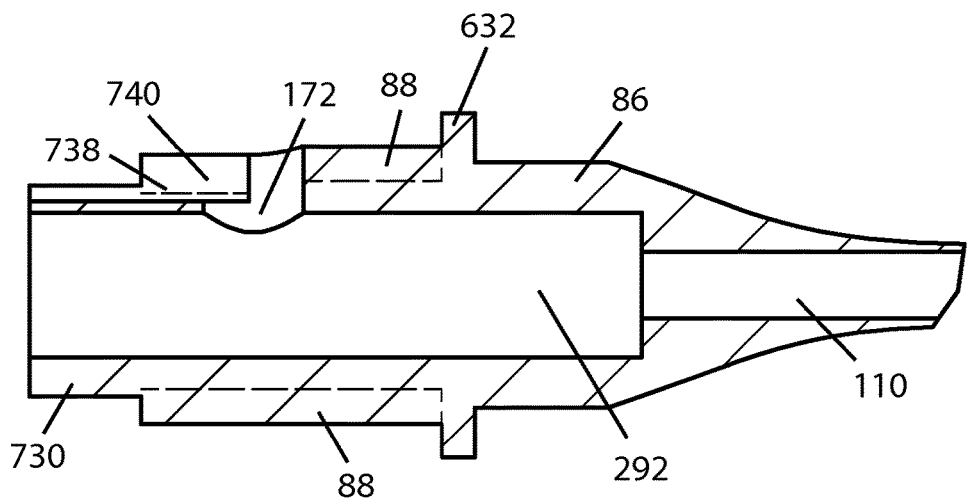
Figure 7A:
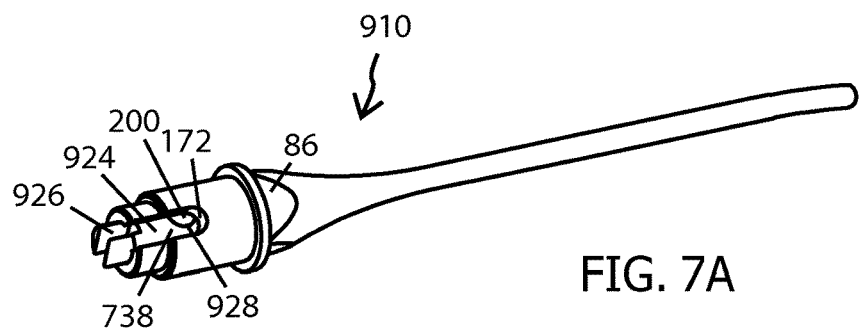
FIGS. 7A to 7E depict perspective and sectional views of a surgical probe that provides all the composing elements of the valve portion of the flow regulator system of the present invention.
Figure 7B:
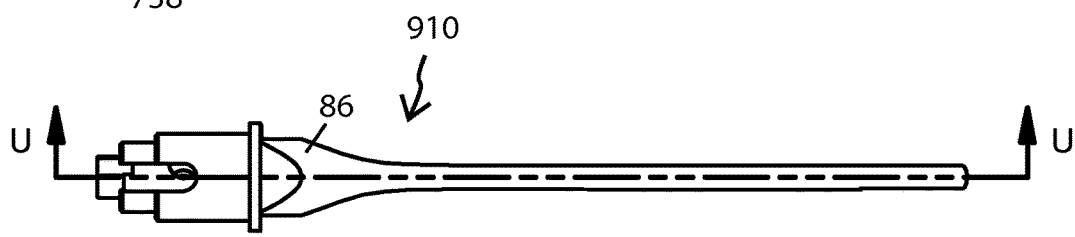
Figure 7C:
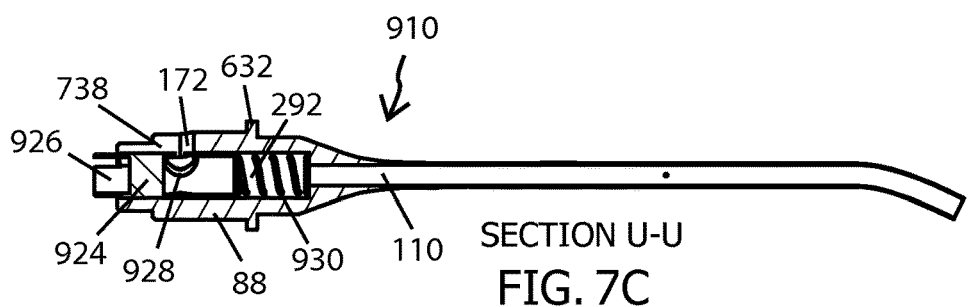
Figure 7D:
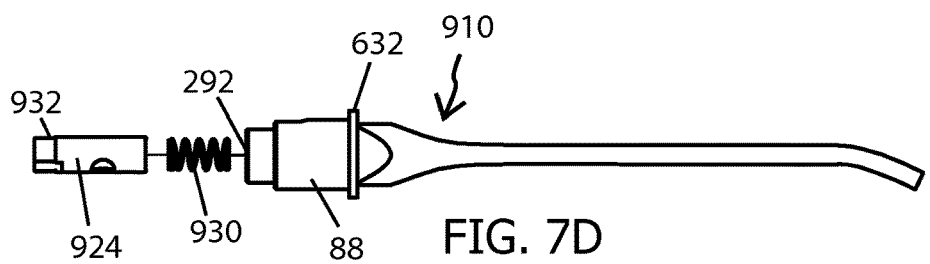
Figure 7E:
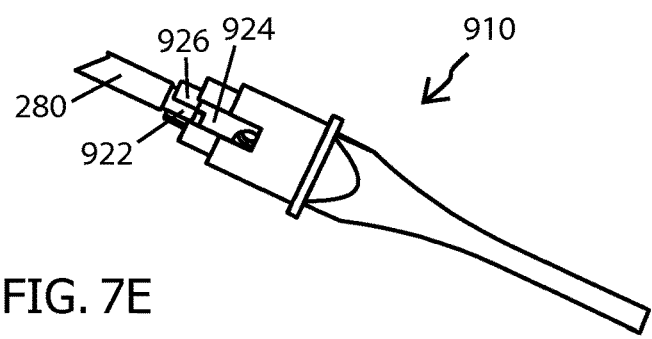

FIGS. 5A to 5G illustrate aspects of an additional embodiment with valve portion 64 of the cyclic aperture flow regulator system 60 of the present invention incorporated into a surgical probe 610 as an alternative approach to reduce the volume of first fluid path 110 to a minimum for use with maximum vacuum levels and still provide high flow stability. A handpiece 600 is shown in FIG. 5A with attached surgical probe 610. Handpiece 600 is shown in FIG. 5B with enclosure 502 removed showing actuator portion 62 of flow regulator system 60 disposed similarly as previously detailed in FIG. 4. In FIG. 5C is seen handpiece 600 with tissue disruption actuator portion 68 and with tube 522 both removed to expose underlying driveshaft 280 and surgical probe 610. In this embodiment driveshaft 280 is extended in a way that driveshaft 280 distal end is operatively in contact with the hub region 86 of surgical probe 610 which contains valve portion 64. FIG. 5D shows surgical probe 610 operationally coupled with tube 522. FIGS. 5E to 5G show slice views of detail region G from FIG. 5D. Rotor 290 is incorporated at the distal end of driveshaft 280 and with attachment of probe 610 to tube 522 becomes functionally disposed within valve chamber 292 enclosed by a chamber wall 630 to conform a complete valve portion 64. In this embodiment rotor 290 has a lid 294 of tubular shape with two circular openings that conform two windows 296a and 296b (also seen in FIG. 8F). Probe 610 incorporates to fluid passages 172 and 174. The extension of the overlay between the entrance of passages 172 and 174 with windows 296a and 296b in lid 294 determines the cross-sectional area of aperture 200. In FIG. 5E rotor 290 is shown positioned in such axial and rotary manner that windows 296a and 296b substantially coincide with the entrance of fluid passage channels 172 and 174 determining an aperture 200 of near maximum dimensions. In FIG. 5F rotor 290 is shown positioned in such axial and rotary manner that windows 296a and 296b partially coincide with the entrance of fluid passage channels 172 and 174 determining an aperture 200 of intermediate dimensions. In FIG. 5F rotor 290 is shown positioned in such axial and rotary manner that windows 296a and 296b do not coincide with the entrance of fluid passage channels 172 and 174 determining a substantial reduction of aperture 200. FIGS. 6A to 6C illustrates with further detail perspective, top and sectional views of a surgical probe 710 incorporating a valve portion 64 including chamber 292 with a single fluid passage 172. Surgical probe 710 provides the fixed constituent parts of valve portion 64 within hub region 86. These parts are essentially valve chamber 292 confined by a chamber wall 730 with one fluid passage 172. As seen in FIG. 6C a valve discharge channel 738 is usually conformed by a cutout volume 740 from hub 86 in combination with the internal wall of tube 522 (FIG. 5E). Valve discharge channel 738 fluidly connects fluid passage 172 with circulation space 523 inside tube 522 all being contributing parts to second fluid channel 112. A hub rim 632 is disposed to provide a hermetical seal between tube 522 distal end and hub 86 during operation both compressed by the tight fit of thread 88. Rotor 290 is an integral part of handpiece 600 and is functionally disposed inside chamber 292 when probe 710 is operationally attached to handpiece 600. This embodiment allows to frequently replace the fixed portion of valve 64 by replacing surgical probe 710 before degradation of system 60 performance by wear of valve chamber 292 of valve portion 64. Rotor 290 can be manufactured of materials resistant to wear such as ceramics, stainless steel or titanium in a way that it can resist wear over more extended use. FIG. 8M is an expanded view of handpiece 600 and surgical probe 610 to better illustrate the complementary action of parts from: 1) handpiece 600 at least providing actuator portion 62, driveshaft 280 and rotor 290, and 2) surgical probe 610 providing valve chamber 292 of valve portion 64 all parts cooperating to conform the cyclic aperture flow regulator system 60 of the present invention.

Handpiece with Axially Adjustable Rotor and "In-Probe" Valve Portion: Surgical Probe Includes Complete Valve Portion 64.

Another additional embodiment is illustrated in FIGS. 7A to 7E where a flow regulating lensectomy probe 910 is provided with a complete valve portion 64 including a matching rotor 924 with rotor windows 928. Rotor 924 is supplied already inserted inside chamber 292. Rotor 924 has a circular stricture 932 that operates as a rotor retainer in combination with a lid provided by probe 910 to maintain the rotor in position. A spring 930 is axially disposed partially compressed inside valve chamber 292 to push rotor 924 toward the exterior end of the usable axial displacement range. Spring 930 can slide frictionless within chamber 292 and also with rotor 290 during rotation and compression. A driveshaft 280 incorporated into handpiece 600 has a distal end feature 922 designed to match a complementary feature 926 of rotor 924 producing a rotary interlock effective to coaxially transmit rotary motion to rotor 924 for valve operation. Driveshaft 280 can exert a controlled pushing action across rotor 924 against spring 930. In this way rotor 924 can be rotated and axially located with precision by the action of driveshaft 280 transmitting rotary and axial power as commanded by controller 132. Flow regulation operation is similar to the previously described embodiments. It can be advantageous to provide the cyclic flow regulator system of the present invention with this embodiment where the complete valve portion 64 of flow regulator system 60 is renovated with each probe 910 exchange avoiding degradation caused by repeated use.

"In-Probe" Valve Portion with Enhanced Tissue Fragmentation Feature

Figure 8A:
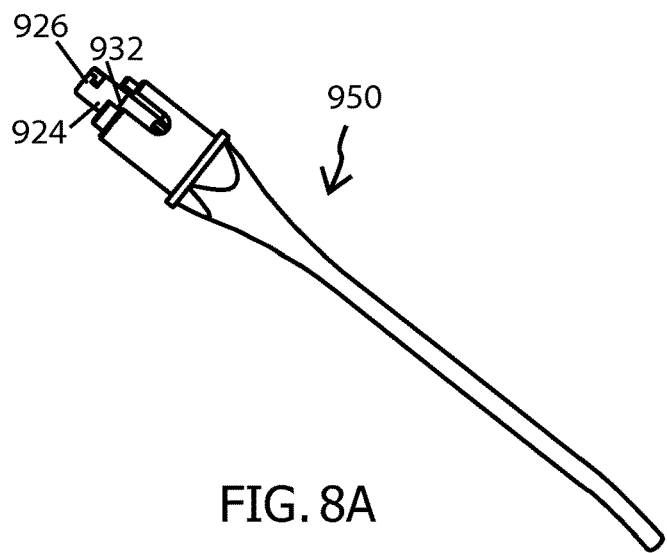
FIGS. 8A to 8J depict perspective and sectional views of another surgical probe that incorporates a complete valve portion of the flow regulator system of the present invention.
Figure 8B:
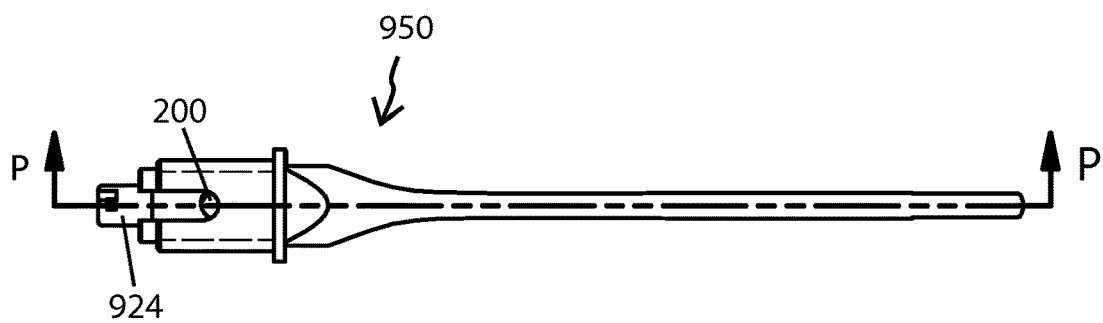
Figure 8C:
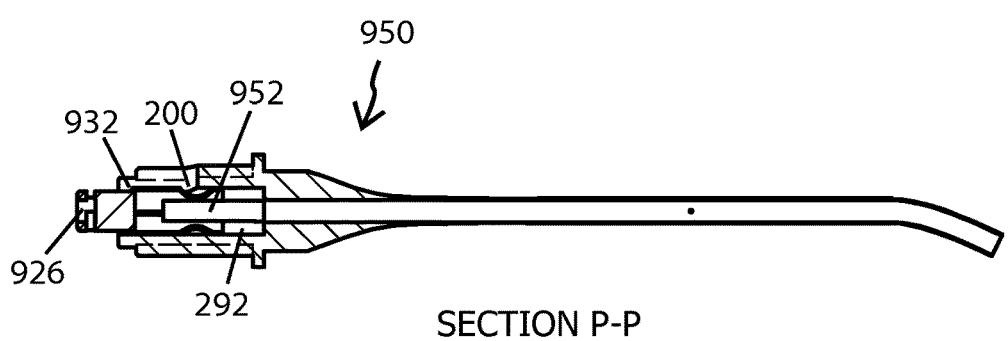
Figure 8D:
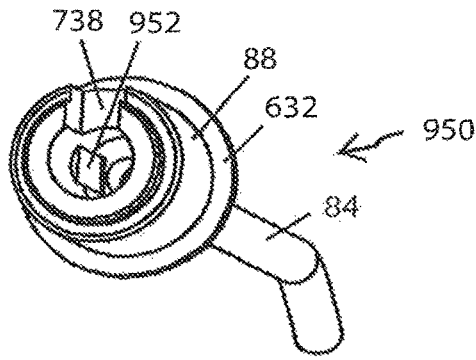
Figure 8E:
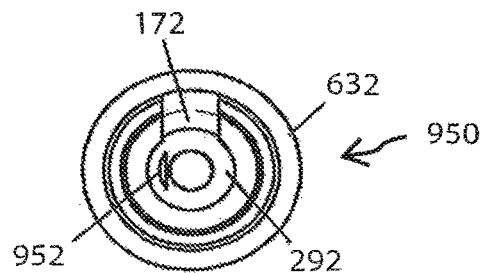
Figure 8F:
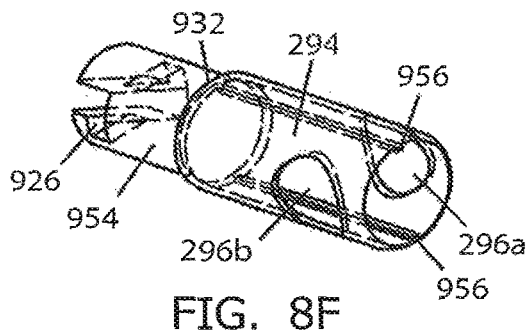
Figure 8G:
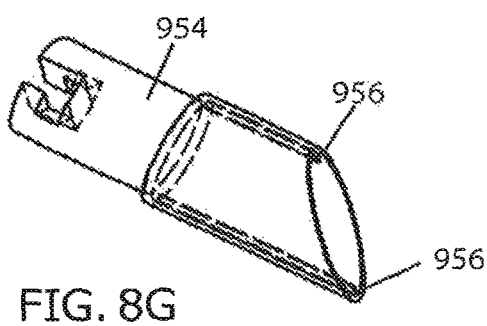
Figure 8H:
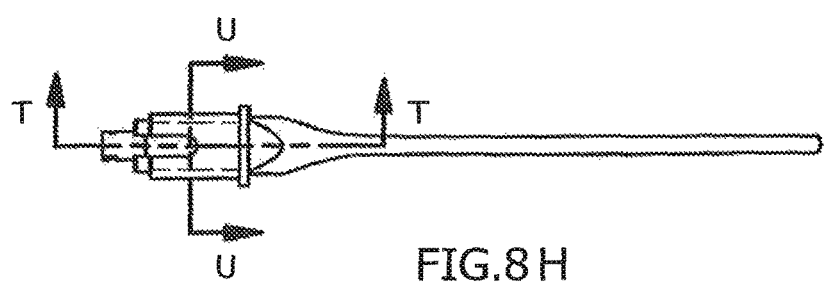
Figure 8I:
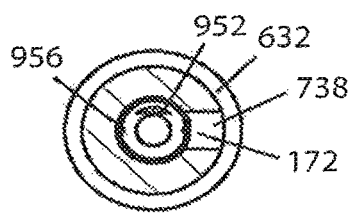
Figure 8J:
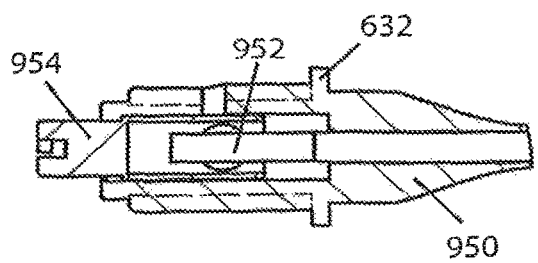
Figure 8K:
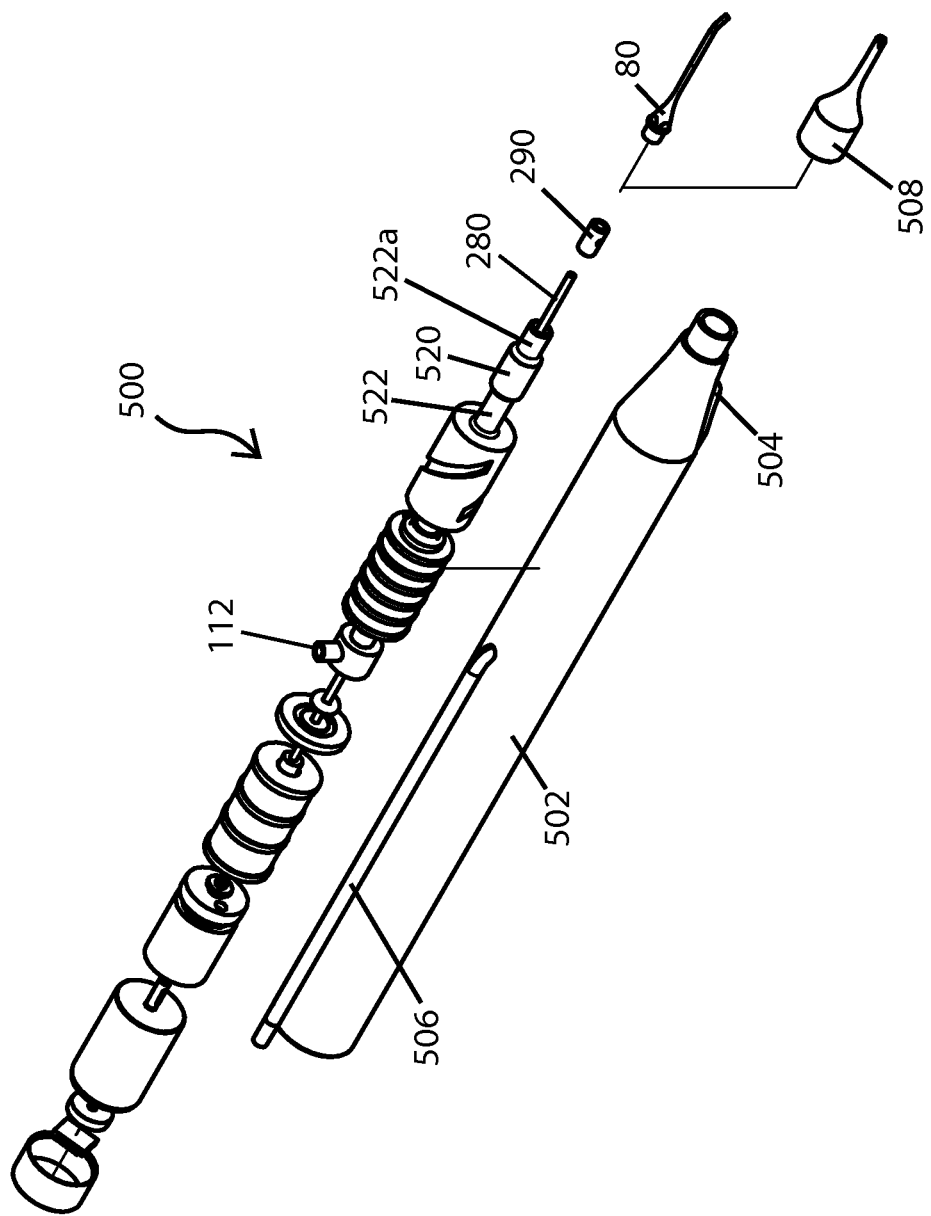
FIG. 8K is an expanded view of a surgical handpiece incorporating an "in-tube" valve portion of the flow regulator system of the present invention.
Figure 8L:
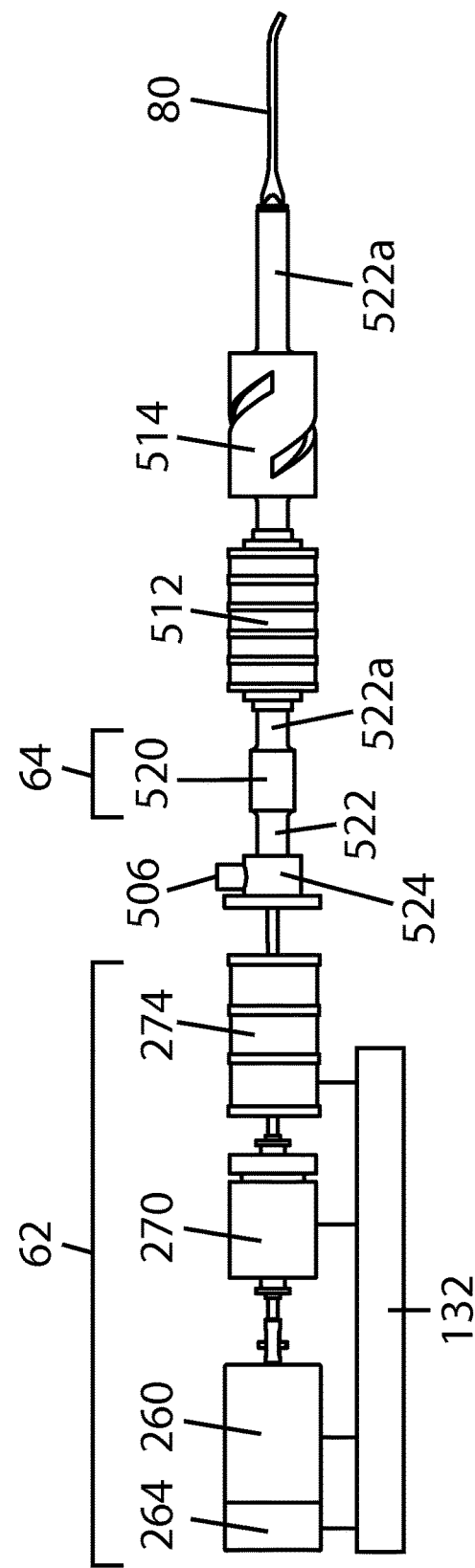
FIG. 8L is a side view of the interior components of a handpiece incorporating the valve portion of the present invention in a location more distant to the surgical probe than the tissue disrupting actuators.
Figure 8M:
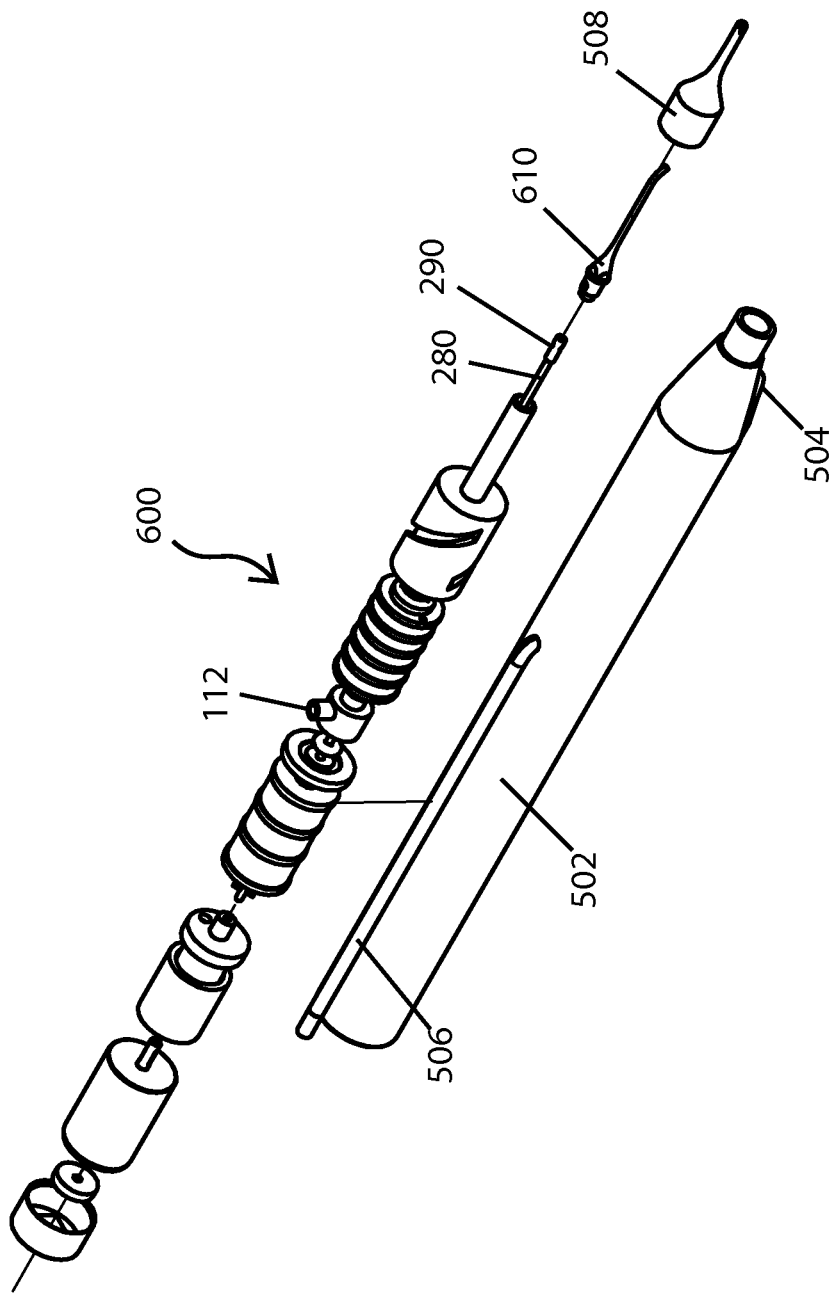
FIG. 8M is an expanded view of a surgical handpiece incorporating an "in-probe" valve portion of the flow regulator system of the present invention.

A variant of the embodiment from FIG. 7 is illustrated in FIGS. 8A to 8J where a surgical probe 950 has a complete valve portion 64 further including an internal spur 952 integral with the bottom of valve chamber 292. A retained valve rotor 954 can additionally incorporate tissue fragmenting features such as sharp ribs operating in combination with spur 952 from probe 950 to compress and fragment tissue during rotation of rotor 954 inside chamber 292 attracted to the periphery by centrifugal force. A conventional rotor further incorporating sharp ribs 956 is shown in FIG. 8F. Incorporation of a spur inside valve chamber 292 leaves little space for spring 930. Therefore a more elaborate rotary-axial interlock between driveshaft 280 and rotor 954 is provided with this embodiment. This alternative interlock allows rotary and axial driving of rotor 954 by driveshaft 280 permitting an axial pulling and pushing action together with rotation without the need of a spring. Use of this embodiment with enhanced tissue fragmenting capabilities can enhance flow stability by further reducing the size of suspended tissue fragments enhancing valve operation and flow stability, particularly when fragments could be extremely hard.

Irrigation-Aspiration (I/A) Handpiece with Cyclic Aperture Flow Regulator System:

FIGS. 13A to 13D illustrate an embodiment of the present invention for use in an irrigation-aspiration surgical handpiece 970 equipped with a cyclic aperture flow regulator system of the present invention. A proximal enclosure 976 contains at least the rotary and linear actuators that conform the actuator portion 62 required for flow control operation and can also contain controller 132 (not shown). A smaller diameter distal enclosure 974 contains the distal portion of irrigation line 102 in fluid communication with irrigation probe 104. Enclosure 974 also contains axial tube 522 with an included "in-tube" flow regulator valve portion 520. An aspiration probe 972 having an aspiration port is coupled to the distal end of tube 522. First fluid path 110 is conformed between aspiration port of probe 972 and aperture 200 inside valve portion 520. This embodiment can be used with advantage to replace conventional irrigation/aspiration hand pieces with the advantage of enabling the use of very high vacuum with controlled flow. Handpiece 970 can allow to aspirate lens fragments through port of soft to medium density with a significant reduction in the use of additional lens disrupting energy. Similarly it can be used to remove more efficiently lens fragments from softened crystalline lenses for example after the use of a femtosecond LASER to soften the lens.

Figure 9A:
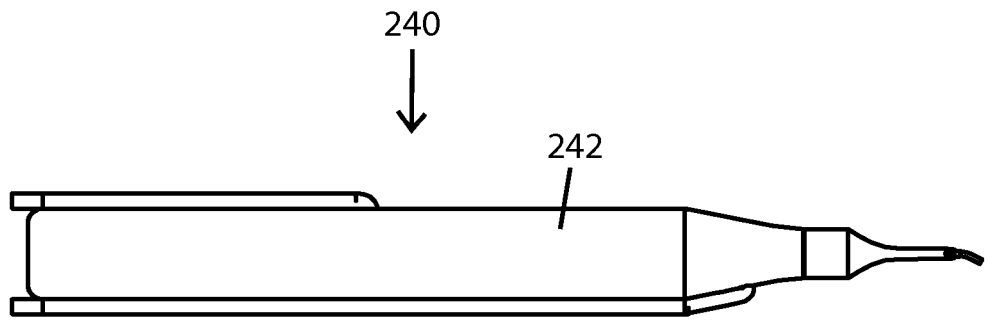
FIGS. 9A and 9B are side views of a handpiece incorporating an embodiment of the present invention with the adjustable fluid path operating with a fixed RMS value of the cross-sectional area.
Figure 9B:
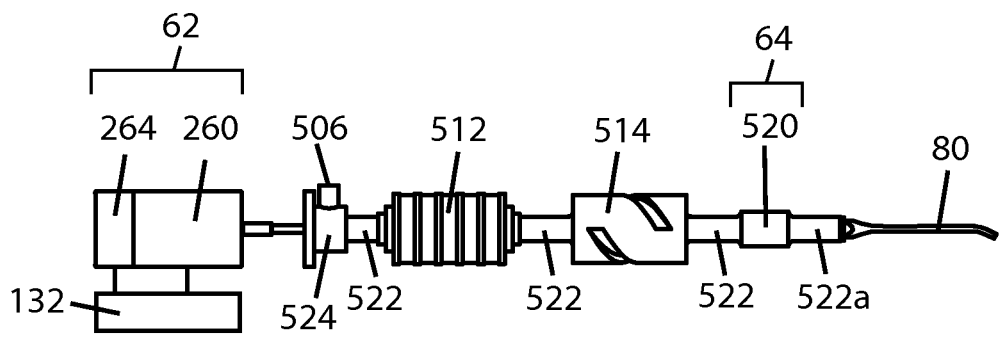
Figure 19:
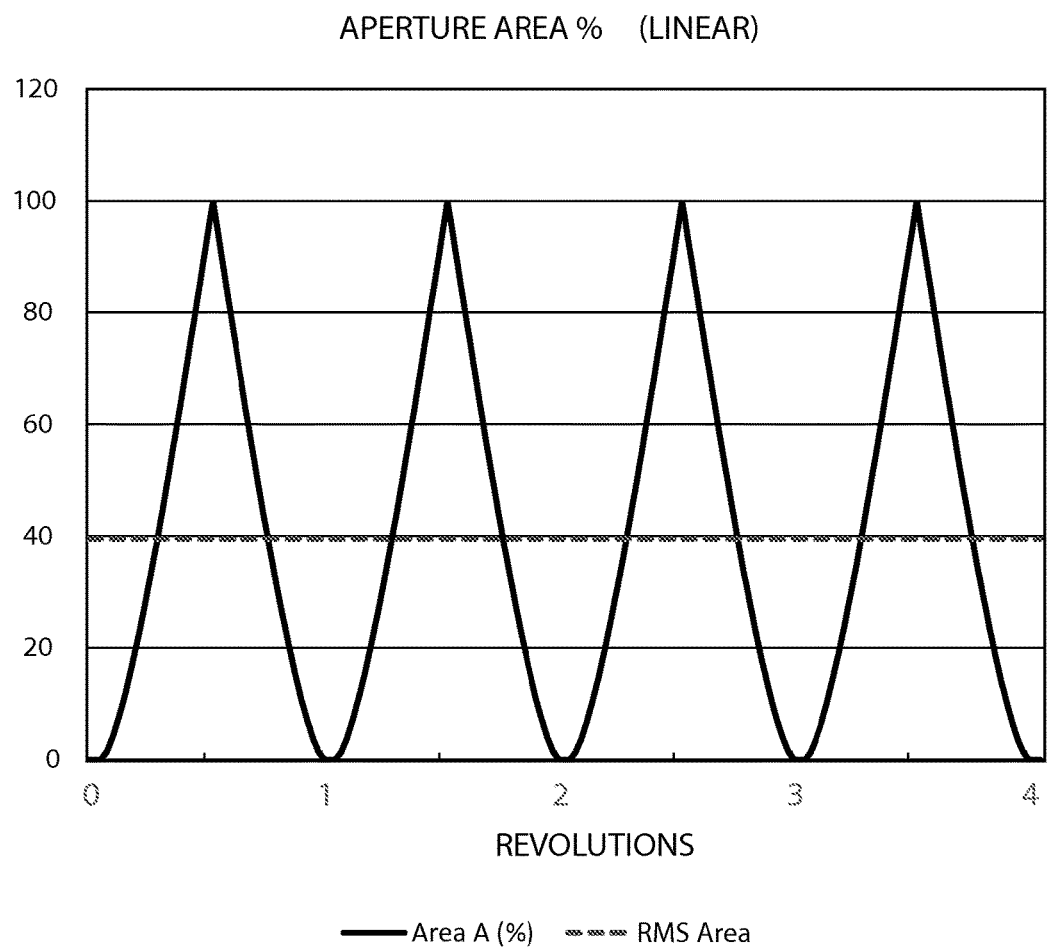
FIG. 19 is a graph depicting the aperture area v/s relative position occurring when tubular opposing surfaces each with one circular opening of equal dimensions slide relative to each other producing a transient aperture of fixed peak dimensions between closed states. This graph can apply to a rotating perforated plunger inside a housing with an equal matching perforation to conform a variable aperture in combination.

Handpiece Having Flow Regulator System with Fixed Cross-Sectional Area RMS:

Illustrated in FIG. 9A is a side view of a surgical handpiece 240 having an enclosure 242. FIG. 9B depicts the interior parts of handpiece 240 with enclosure 242 removed. A rotary motor 260 is operable to rotate driveshaft 280 around its axis. This embodiment has no structure to support the adjustment of the axial position of driveshaft 280 and rotor 290 relative to chamber 292. During operation this embodiment produces rotation of rotor 290 inside chamber 292 in a fixed axial position producing cycles of variation of the cross-sectional area of aperture 200. During each rotary cycle of rotor 290 there is at least one portion of the cycle where the cross-sectional area of aperture 200 is substantially reduced or closed. In this embodiment the RMS value of the cross-sectional area of aperture 200 is fixed as provided and nonadjustable. When using this embodiment aspiration flow can be adjusted by varying the vacuum level provided by vacuum source 114. Higher vacuum levels will produce higher flow rates and no vacuum will produce no flow. As a mode of example FIG. 19 is a graph illustrating the percentage fluid aperture 200 area fluctuation along 4 revolutions of driveshaft 280. An operator could choose a valve with determined vacuum-flow curve specifications from a plurality of valve configuration options.

Figure 9C:
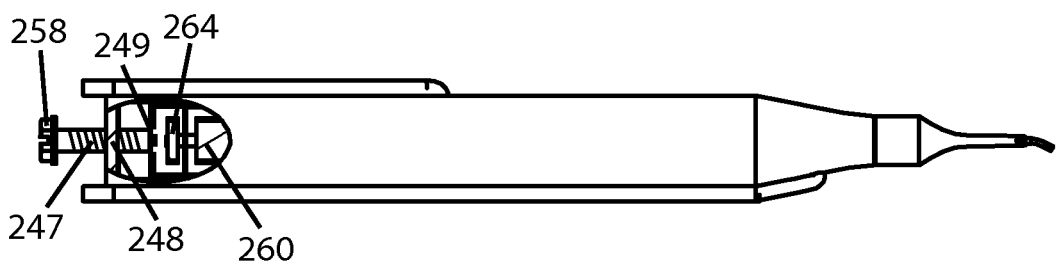
FIG. 9C is a side view of a handpiece similar to that shown in FIGS. 9A and 9B further incorporating a mechanism that allows an operator to manually adjust the RMS value of the cross-sectional area.

A variation of the embodiment shown in FIGS. 9A and 9B is shown in FIG. 9C where a screw 258 with a male thread 247 is provided passing through a female thread 248 in handpiece enclosure 242. Screw 258 is interiorly attached to an enclosure 249 of actuator portion 62 including sensor 264 and motor 260. Rotation of screw 258 produces an axial displacement of motor 260 and indirectly an axial displacement of driveshaft 280 and of rotor 290. An operator can manually adjust the axial position of rotor 290 inside chamber 292 by turning screw 258 and in this way modify the cross-sectional area RMS value of aperture 200. This action modifies the vacuum-flow relation of the flow regulator unit changing performance. Shown in FIGS. 20A and 20B is an embodiment designed to manually regulate flow by depression of a lever 326 anchored in a pivot 328. Depression of lever 326 by an operator finger progressively increments flow rate and vice versa. Rotary power is delivered to rotary member 330 by rotary motor 260 while axial position of member 330 is determined by the degree of depression of lever 326. No depression has member 330 in fully extended position having no aperture and no flow. Lever 326 depression compresses spring 314 by washer 316 and produces axial displacement of member 330 progressively increasing peak aperture 200 area between periods of total closure during each member 328 revolution. By applying a steady vacuum to second fluid path 112 and depressing lever 326 while motor 260 is rotating, an operator can precisely manually control flow rate of aspiration from a surgical site.

Parts or all portions of a rotary valve 64 can be disposable or designed for frequent replacement. Shown in FIGS. 22A to 22C is a valve portion 64 with a detachably coupled motor 62 that can be operatively installed at the rear portion of a handpiece 400 of the prior art to regulate flow and cancel post-occlusion surges. As seen in FIGS. 22 to 27 a rotary motor 260 is attached to a valve body 876 by a detachable interlocking mechanism 882. Valve body 876 includes aspiration line input port 170 and output port 180. Optionally body 876 can also incorporate an irrigation line bypass tube 866 with an input port 868 and an output port 870 for insertion in the irrigation line 102. Irrigation fluid can be derived from bypass 866 through an irrigation fluid channel 872 to fill an irrigation fluid chamber 874. O-ring seats 888 and 890 can accommodate O-rings 878 and 880. A low friction washer 882 is disposed to receive driveshaft 280 connecting a rotary key 886 with rotor 290 including rotor window 296. Motor 260 has a rotor key 884 that can engage with rotor key 886 to transmit rotary motion. A hollow valve tube 894 with interior diameter precisely matching the exterior diameter of tubular rotor 290 is disposed inside valve body 876 to receive rotor 290. Tube 894 has a fluid passage 170 operatively matching rotor window 172 to produce a fluid aperture of variable dimensions during rotation. Motor 62 can be independent or incorporated into handpiece 500 as seen in FIG. 22D. Motor 62, valve 64 and handpiece 500 can be held in operative position by interlocking mechanisms 882. Rotary valve body 876 containing fluid channels that form part of fluid paths 110 and 112. Valve body 876 has a double seal mechanism for driveshaft 280 that incorporates intermediate seal chamber 874. First seal bed 888 incorporates O-ring or lip seal 878 and dynamically isolates ambient air at atmospheric pressure from intermediate chamber 874 that can be filled with saline derived from the irrigation line 102 typically at a pressure higher than atmospheric pressure. Second seal bed 890 also receives an O-ring or lip seal 880 and dynamically isolates fluid filled intermediate chamber 874 from valve chamber 292 potentially operating at high vacuum. This valve configuration allows for improved seal life and reduced driveshaft 280 loading by relieving second sealing element 880 from performing as a dry vacuum-tight seal. Instead cooling and lubricating fluid is provided at the higher pressure side of second sealing element 880. In this way driveshaft 280 sealing elements 878 and 880 can be designed for reduced driveshaft compression load allowing higher RPM with extended seal life. In FIGS. 23 to 27 several sectional views as well as an expanded view are shown of this valve portion embodiment of the present invention. Variations of this embodiment can be used with advantage in existing surgical probes. Also, hand pieces can be designed to operate the valve portion here illustrated by including a motor portion 62 that operatively couples with valve driveshaft 280 inserted in a valve body 876. A controller 132 can be provided by a driving console or independent.

Figure 12:
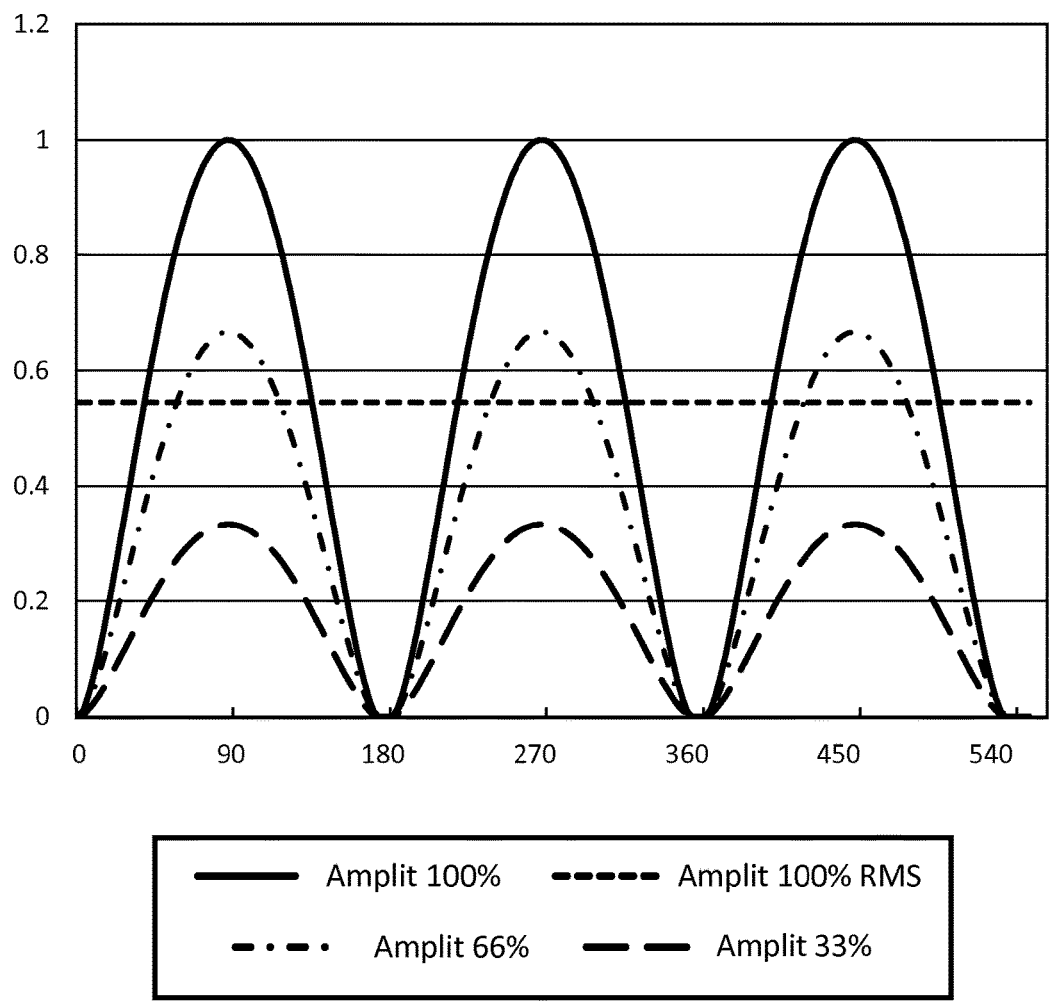
FIG. 12 is a graph illustrating the aperture cross-sectional area variation along one full cycle of oscillation from the examples from FIGS. 10A to 10J represented for three different linear oscillation amplitudes.
Figure 28A:
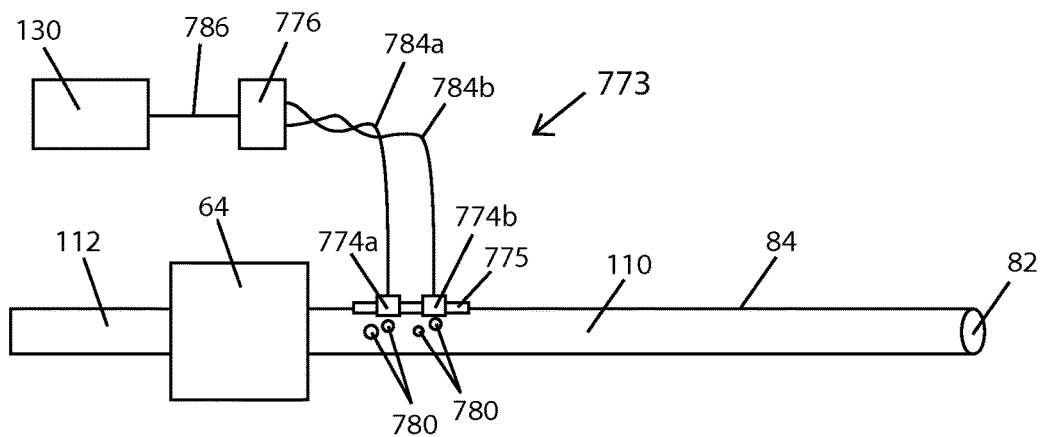
FIG. 28A is a schematic illustration of the valve portion of the flow regulator system further incorporating a bubble generator in the first fluid path producing bubbles by circulating an electric current through an electrolyte solution.
Figure 28B:
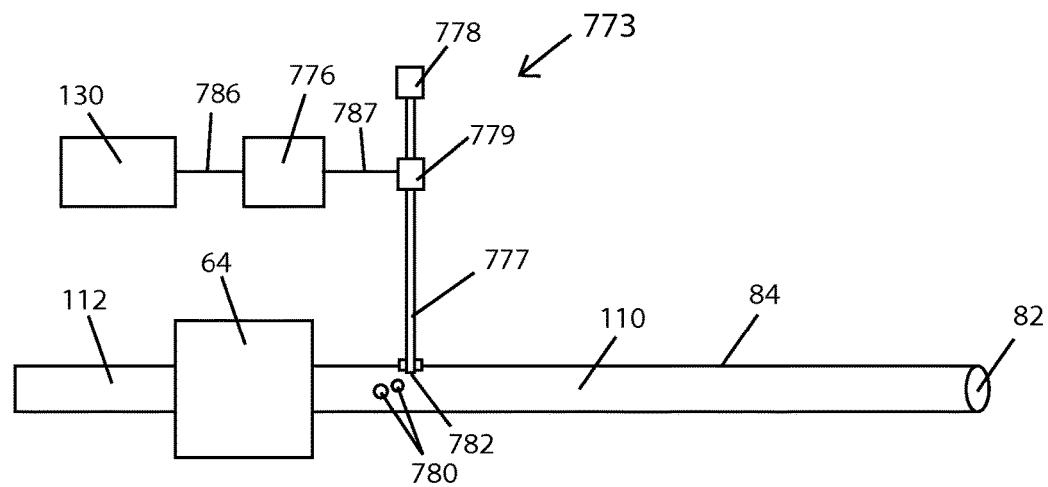
FIG. 28B is a schematic illustration of the valve portion of the flow regulator system further incorporating a bubble generator in the first fluid path producing bubbles by injection of gas through a nozzle.

Cyclic Aperture Flow Regulator System Driven by Oscillatory Actuator:

FIG. 10A is a perspective view of a flow regulator system 60 having valve portion 64 and actuator portion interconnected by a shaft 162. In this embodiment valve portion 64 is mechanically actuated by a single oscillatory actuator 160 through shaft 162 that transmits vibratory motion. FIGS. 10C to 10D are cross sectional slice views from FIG. 10B. A valve body 166 has an input port 170 and an output port 180. Input port 170 and output port 180 are fluidly connected inside body 166 through two fluid passages 172 and 174. A slit 178 perpendicularly traverses both fluid passages. Slit 178 internally receives an oscillatory blade 164 having a window 176. Blade 164 is mechanically connected with shaft 162 to receive axial displacement from actuator 160. Shaft 162 has a watertight and airtight seal 163. Window 176 in blade 164 is positioned in a way that when actuator 160, shaft 162 and blade 164 are in a centered position, blade 164 totally obliterates both fluid passages 172 and 174 (FIG. 10C). Actuation of actuator 160 over shaft 162 to produce a proximal displacement of blade 164 locates window 176 over fluid passage 174 creating a first fluid aperture 200a (FIG. 10D). Actuation over shaft 162 by actuator 160 to produce a distal displacement of blade 164 locates window 176 over fluid passage 172 creating a second fluid aperture 200b (FIG. 10E). A "brake before make" concept can be considered in the design of valve 64 this meaning that a substantial reduction of the cross-sectional area of one fluid aperture must occur before the opposite fluid aperture begins to open. As illustrated in FIGS. 11A to 11J, blade 164 with window 176 oscillating around the centered position from FIG. 10C alternates between a first and a second fluid aperture 200a and 200b passing over the centered position two times during each cycle of oscillation. Operation of this embodiment occurs with actuator 160 energizing blade 164 to oscillate at a frequency fast enough to produce steady flow and minimal ripple, similar to the rotary embodiment. A typical frequency of oscillation is above 200 Hertz to produce levels of ripple below 10%. The frequency of oscillation required to produce levels of ripple below 10% is reduced when a bubble generator 773 as described in FIGS. 28A and 28B is activated during operation. In this way, frequencies of oscillation of 100 Hertz can produce pressure ripple levels below 10% when the bubble generator is operated simultaneously with aspiration. In this embodiment flow rate can be adjusted by varying the amplitude of oscillations of blade 164 in a way that increasing the amplitude of oscillation will increase aperture dimensions subsequently increasing flow. Flow is a function of the RMS value of the sum of apertures 200a and 200b cross sectional-areas. As with the main embodiment, flow rate is also a function of the vacuum level at second fluid path 112. Thus a second modality to regulate unobstructed flow into a surgical probe is to increase vacuum to increase flow. The graph in FIG. 12 displays the total aperture (summed cross-sectional areas of apertures 200*a*+200*b*) along phase during 1.5 sine wave oscillations. The example corresponds to a prototype valve designed with equally sized circular openings for fluid passages 172, 174 and for window 176. Three tracings are provided. Top tracing corresponds to maximum oscillatory amplitude. Middle tracing corresponds to ⅔ of maximum amplitude and bottom tracing corresponds to ⅓ of maximum amplitude. The horizontal dotted line represents the RMS value for the cross-sectional area of the waveform in the top tracing. As a mode of reference only, apertures 200*a* and 200*b* of maximum summed dimensions of 0.65 mm² and minimum dimensions of 0.001 mm² operated at 680 mmHg vacuum produces a substantially steady unobstructed flow of 24 cc/min and effectively cancels post-occlusion surge with minimum ripple (below 10%) when operated at an oscillation frequency of 200 Hertz.

Figure 13A:
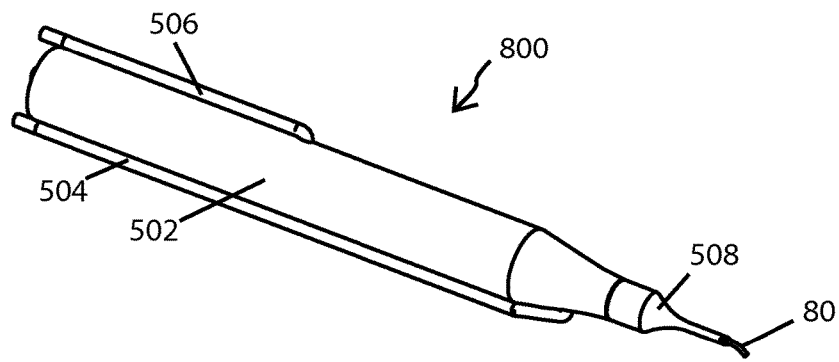
FIGS. 13A to 13H correspond to different perspective, detail and sectional views of one implementation in a surgical handpiece of the oscillatory embodiment shown in FIG. 10 of the cyclic aperture flow regulator system.
Figure 13B:
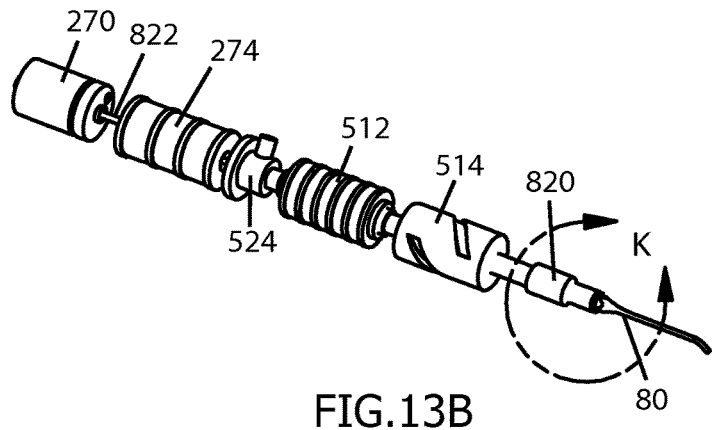
Figure 13C:
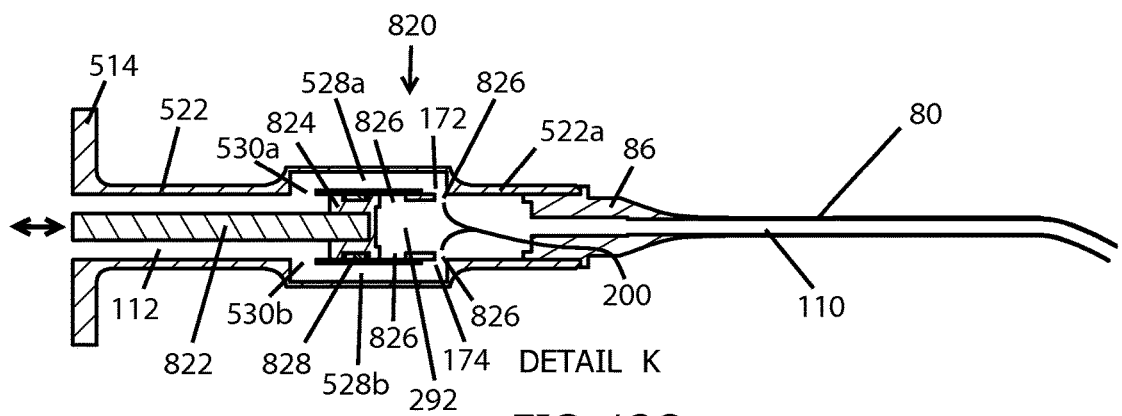
Figure 13D:
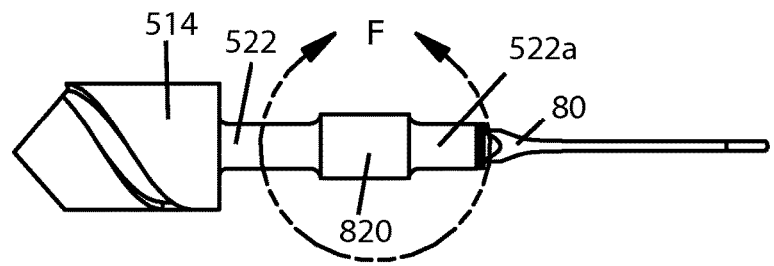
Figure 13E:
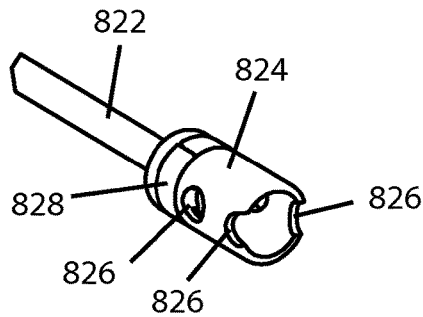
Figure 13F:
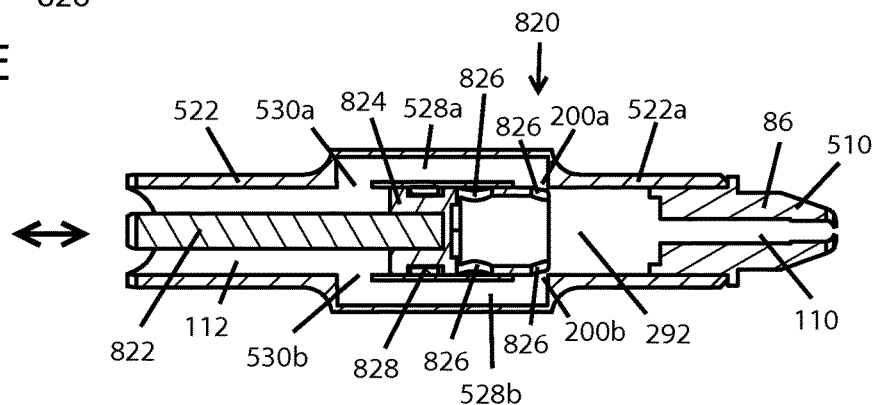
Figure 13G:
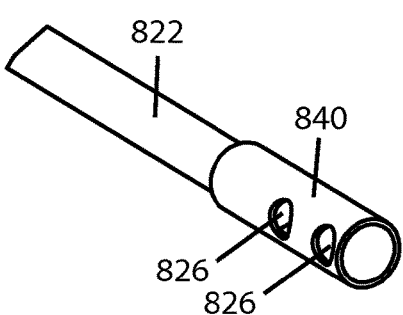
Figure 13H:
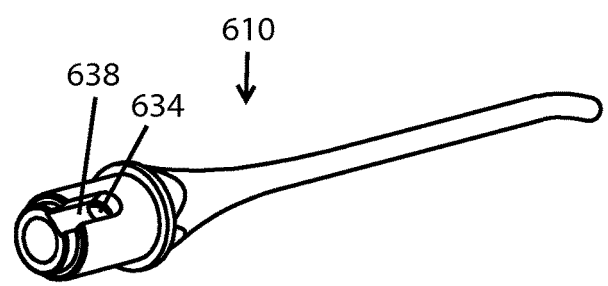
Figure 14A:
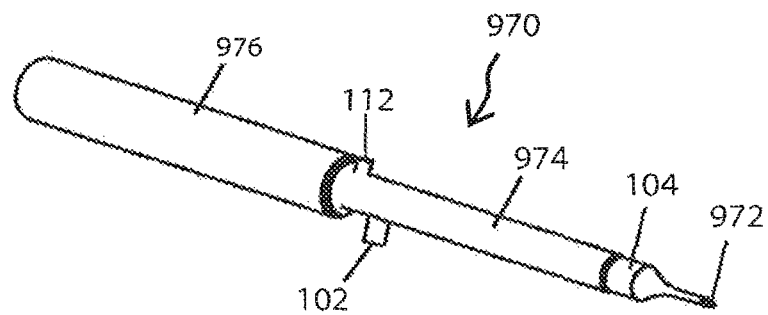
FIGS. 14A to 14D correspond to different perspective, detail and sectional views of one implementation of the flow regulator system of the present invention in an irrigation/aspiration surgical handpiece.
Figure 14B:
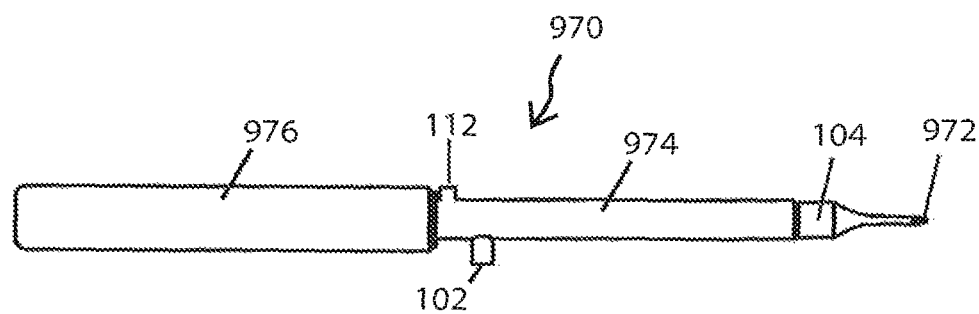
Figure 14C:
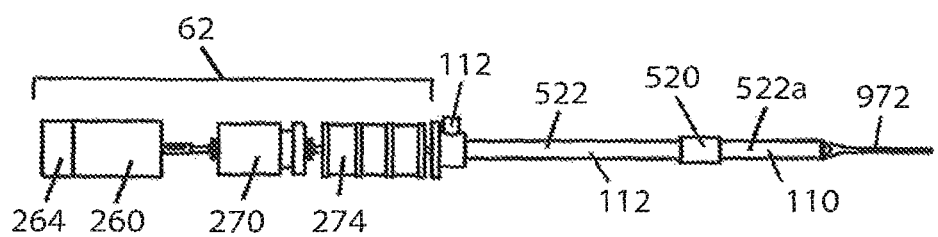
Figure 14D:
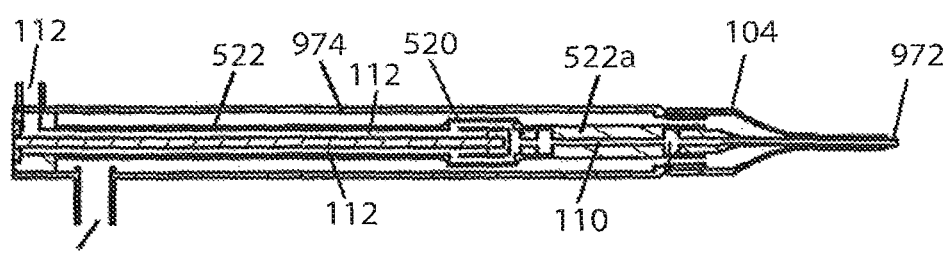

Depicted in FIGS. 13A to 13F is a handpiece 800 with an embodiment of the cyclic aperture flow regulator system 60 of the present invention that has an actuator portion 62 composed by an oscillatory linear actuator. Handpiece 800 shown in FIG. 13B with enclosure 502 removed exposes linear actuator 270 as the single flow regulator actuator mechanism. An "in-tube" valve portion 820 accommodates an oscillating valve in-tube piston 824 inside valve chamber 292. Shaft 822 can be configured to be rotationally stable having a single degree of freedom to coaxially displace inside tube 522 without rotation. Rotational stability of shaft 822 with attached in-tube piston 824 can contribute to the alignment between in-tube piston 824 and chamber 292. In-tube piston 824 can further incorporate a piston ring 828 for improved minimize leakage. At least one piston window 826 is arranged in a way that when shaft 822 is in an axial centered position no overlap exists between window 826 and the entrance of fluid passages 172 and 174. In this position the cross sectional area of aperture 200 is substantially reduced limiting or eventually cancelling flow. Operation of actuator 270 produces oscillation of the shaft of linear actuator 270 that transmits axial vibratory motion to in-tube piston 824 in a way that window 826 overlaps with the entrance of passages 172 and 174 in an alternating manner. This action produces cycles of variation of the cross-sectional area of aperture 200 (200*a*+200*b*) including a transition through the center position where the cross-sectional area of fluid aperture 200 is substantially reduced or closed. The frequency of the cycles of oscillation of in-tube piston 824 is determined by controller 132 driving actuator 270 to operate at a frequency sufficiently high to produce a substantially steady flow through surgical probe 80. Shown in FIG. 13C is a slice detail view from FIG. 13B showing a snapshot representation of in-tube piston 824 with windows 826 located in such position that a partial aperture 200 is conformed. Increasing the vibratory amplitude of in-tube piston 824 increases the RMS value of the cross-sectional area of aperture 200 increasing flow for a given vacuum in fluid path 112. Amplitude of vibration can be monitored using linear motion sensor 274 connected to controller 132. As with the preferred embodiment, this oscillatory version of the cyclic aperture flow regulator 60 can be implemented both with an "in-tube" valve portion 64 as depicted in FIGS. 13A to 13F or with an "in-probe" valve portion. FIG. 13G illustrates an in-valve piston 840 designed to match with a surgical probe 610 shown in FIG. 13H for "in probe" oscillatory operation. Surgical probe 610 is designed with a matching valve chamber to operatively receive in-valve piston 840. Fluid passages 634 and outflow channels 638 from probe 610 work in cooperation with windows 826 of in-valve piston 840 from FIG. 13G to complete the valve portion 64.

In FIG. 18A is depicted an alternative embodiment where actuator portion 62 with oscillatory actuator 160 and oscillatory shaft 162 further includes a single degree of freedom spring-mass system governed by the laws of driven harmonic oscillators. Shaft 162 of oscillatory actuator 160 is mechanically coupled to the proximal end of a spring 210 characterized by the equation F=−k*x. The distal end of spring 210 is in turn mechanically connected to a mass 212 of weight W physically integral with blade 164.

The spring-mass configuration of this embodiment allows for a larger amplitude of oscillation of blade 164 with regard to the amplitude of oscillation of shaft 162 when actuator 160 is operated at or near a harmonic frequency. Actuator 1160 can operate at subsonic, sonic or ultrasonic frequency. In the case of ultrasonic actuators, the spring-mass system can be replaced by a nosecone configuration to amplify actuator stroke without departing from the present invention.

Spring 210 and mass 212 characteristics are selected to vibrate in resonant mode when driven by actuator 160 at the desired frequency of operation. This embodiment allows to generate the required peak-to-peak amplitude of oscillation of blade 164 with actuator 160 oscillating shaft 162 at lower amplitudes that are amplified by the spring-mass system. In this way oscillator 160 can have a smaller footprint and consume less power to activate blade 164 compared to the configuration where shaft 162 directly couples with blade 164.

When a spring-mass configuration is used, a second modality to control amplitude of oscillation of blade 164 becomes available consisting in controllably shifting the driving frequency of actuator 160 around at least one of the harmonic frequencies. A first modality of flow control could then consist in adjusting the amplitude of oscillation of shaft 162 at a constant harmonic or near harmonic frequency.

A second modality of flow control could consist in adjusting the amplitude of oscillation of shaft 162 at a constant amplitude around a harmonic frequency to regulate the amplitude of blade 162 peak-to-peak displacement. Also a combination of amplitude modulation and frequency modulation could be used for this embodiment of flow regulator system 60. Flow regulator system 60 incorporating the spring-mass system of FIG. 18A can be desirable where the present invention is to be installed in a small handpiece.

In FIG. 18B is depicted another alternative embodiment that incorporates a linear actuator 214 operated by processor 132. When activated, actuator 214 is operative to transitorily axially displace actuator 160 and blade 162 relative to valve body 166 from a centered closed position to an open flow-enabling position where window 176 overlaps with one admission channel 164 or 174 to produce a steady aperture of selectable area. Actuator 214 can be a step displacement linear actuator or a proportional linear actuator. Incorporation of actuator 214 is depicted in an embodiment with a spring-mass system but can also be included in the basic embodiment from FIG. 10.

An enhanced anti-clogging feature can be incorporated to operate when valve 64 is operating at low amplitude, low flow, near closed conditions. Processor 132 can be programmed to command operation of actuator 62 in a way that amplitude of oscillation of blade 164 is intermittently set at high amplitude for a short period to then return to a baseline low amplitude vibration level. This transitory large aperture dimensions can allow large tissue fragments to traverse the regulator mechanism and be eventually fragmented to get cleared to prevent valve clogging.

The duration and repetition rate of this high amplitude bursts can be programmed or adjusted to have minimal impact on the overall flow conditions being commanded by the operator, also correcting for the overall increase in aspiration flow. An optional linear actuator 214 can operate to axially displace motor assembly 160 including blade 164 in a way that a permanent non-cyclic aperture 200 is established between inflow port 170 and outflow port 180. This action commanded by processor 132 can be useful during reflux operations and during priming operations, as well as an alternative means to unclog an eventually clogged flow regulator system 60 mechanism by tissue fragments or other solid materials.

Stand-Alone Flow Regulator System Embodiment:

The cyclic aperture flow regulator system described in the preferred embodiment has an actuator portion 62 with sensors and actuators driven by a flow regulator controller 132 disposed in surgical console 150. Although this mode of operation allows the integration of multiple variables to improve system operation it is not a strict requirement for the implementation of this invention. Controller 132 including a processor and data storage memory can be incorporated in the same unit containing actuator portion 62 eventually requiring only external power such as a DC supply to operate in standalone mode. A user interface such as a foot pedal 152 can directly connect to this standalone flow regulator system unit for an operator to command operation. The unit can further incorporate a vacuum sensor 140 in fluid connection with second fluid path 112 and disposed for example in the valve portion 64 of the flow regulator system 60 and connected to controller 132 for improved control of operation. The flow regulator system 60 can operate independent of a surgical handpiece and can be disposed in-line in the aspiration path between a surgical handpiece and a vacuum source.

Embodiment Incorporating an Alternative Bubble Generator in the Fluid Path:

Shown in FIG. 30B is a schematic illustration of an alternative implementation of a gas generator 773 for fluid path 110 consisting in a bubble injector tube 777. Tube 777 can have a diameter in the range of 1 to 50 microns and a length L. Tube 777 can be connected to a source of gas 778 at a selected pressure. The selected pressure can be atmospheric pressure or a different pressure. A gas valve 779 can be installed in the path between tube 777 and gas source 778. A gas generator driver 776 operates gas valve 779 through a signal cable 787. Controller 132 can be programmed to command operation of controller 776 through signal cable 786 to adjust the amount of gas injected into fluid path 110 at any given time according to console parameters. The normalized flow rate of gas injected into path 110 can range between zero liters per minute (NLPM) and 0.00001 NLPM. In In its simplest form gas source 778 can be filtered ambient air but other sources of gas can be considered such as water vapor.

The cyclic flow regulator system of the present invention allows stable aspiration of fluid and tissue fragments from a body cavity such as the interior of an eye using high vacuum with adjustable flow rate. In this way surgical procedures can be performed faster, safer and require less auxiliary lens disrupting energy such as ultrasound or LASER.

The reader will see that the Cyclic Aperture Modulation Flow Regulator System here described allows to perform more efficient and safer surgical procedures by controlling flow and increasing the range of safe use of vacuum inside surgical aspiration lines. While the provided description contains many specificities, these should not be construed as limitations on the scope, but rather as an exemplification of several embodiments thereof. Many other variations are possible. The system has been primarily conceived for ocular surgery, and more particularly for lens removing surgeries such as cataract and refractive lensectomy procedures. Other surgical procedures where fluid and tissue fragments need to be removed through a surgical probe can benefit from the practice of the present invention such as for example, endoscopic joint surgeries. Design can widely vary. For example single or multiple apertures inside the valve chamber can be used. A diversity of shapes can be used for the entrance of the fluid passages that participate to conform the variable fluid apertures. Different numbers and shapes for fluid windows, ports and lids can be incorporated. Fluidic channels that participate in valve configuration can be closed or open and in such case being completed by neighboring parts. Different kinds of linear and rotary motors can be used. Different kinds of motion sensors can be used, all this without departing from the scope of the present invention. Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A cyclic aperture flow regulator system comprising:
    a cyclic aperture flow regulator valve portion having a valve output defining a first fluid passage with an adjustable cross-sectional area, the first fluid passage of the valve output located in a fluid path connecting an aspiration opening of a surgical probe with a vacuum source, the cyclic aperture flow regulator valve portion comprising a valve rotor disposed in a valve chamber, the valve rotor capable of 360 degree rotation about an axis of rotation, the valve rotor disposed in the valve chamber such that the valve rotor is capable of translation in a direction parallel to the axis of rotation;
    a linear actuator associated with the cyclic aperture flow regulator valve portion, the linear actuator operable to adjust the cross-sectional area of the first fluid passage;
    a cyclic aperture flow regulator controller providing a command signal to a rotary motor to cause the valve rotor to continuously rotate through 360 degrees at a speed of greater than 2000 revolutions per minute so as to produce cycles of variation of the cross-sectional area of the first fluid passage, each of said cycles including at least one time segment where said cross-sectional area of the first fluid passage is substantially reduced, said cycles occurring at a frequency sufficiently high to produce a substantially steady aspiration flow; and
    a bubble generator located adjacent to the cyclic aperture flow regulator valve portion.

2. The system of claim 1, wherein a root mean square value of said cross-sectional area of the first fluid passage during said cycles is adjustable by an operator.

3. The system of claim 1, wherein the cyclic aperture flow regulator valve portion includes a rotor lid slidably disposed inside the valve chamber.

4. The system of claim 1, wherein the cyclic aperture flow regulator valve portion is incorporated into a surgical handpiece.

5. The system of claim 1, wherein the cyclic aperture flow regulator valve portion is incorporated into the surgical probe and operated by a lever located on a surgical handpiece.

6. The system of claim 1, wherein the cyclic aperture flow regulator valve portion is detachably coupled to a surgical handpiece.

7. The system of claim 1, further comprising a position sensor configured to provide a feedback signal to said cyclic aperture flow regulator controller.

8. The system of claim 1, further comprising a tissue fragmentation feature to enhance tissue fragment clearance through the fluid path.

9. The system of claim 1, wherein the first fluid passage has a maximum cross-sectional area from 0.3 mm$^2$ to 0.65 mm$^2$ and a minimum cross-sectional area from 0.001 mm$^2$ to 0.003 mm$^2$.

10. The system of claim 1, wherein a frequency of said variation in the cross-sectional area of the first fluid passage is greater than 130 Hz.

11. The system of claim 1 further comprising a fluid capacitor located between the aspiration opening of the surgical probe and the first fluid passage.

12. The system of claim 11 wherein the fluid capacitor has a fluid capacitance value between 0.01 μL/mmHg and 1.0 μL/mmHg.

13. The system of claim 1, wherein the bubble generator produces gas bubbles in the fluid path at a location between the aspiration opening of the surgical probe and the first fluid passage.

14. The system of claim 13 wherein gas bubbles are produced in said fluid path by injection through a nozzle.

* * * * *